(12) United States Patent
McGilligan

(10) Patent No.: US 12,264,201 B2
(45) Date of Patent: *Apr. 1, 2025

(54) BISPECIFIC ANTIBODY TARGETING IL-1R1 AND NLPR3

(71) Applicant: University of Ulster, Coleraine (GB)

(72) Inventor: Victoria McGilligan, Londonderry (GB)

(73) Assignee: UNIVERSITY OF ULSTER, Coleraine (GB)

( * ) Notice: Subject to any disclaimer, the term of this patent is extended or adjusted under 35 U.S.C. 154(b) by 995 days.

This patent is subject to a terminal disclaimer.

(21) Appl. No.: 17/275,986

(22) PCT Filed: Sep. 16, 2019

(86) PCT No.: PCT/EP2019/074745
§ 371 (c)(1),
(2) Date: Mar. 12, 2021

(87) PCT Pub. No.: WO2020/053447
PCT Pub. Date: Mar. 19, 2020

(65) Prior Publication Data
US 2022/0033507 A1  Feb. 3, 2022

(30) Foreign Application Priority Data
Sep. 14, 2018 (GB) ..................... 1815045

(51) Int. Cl.
*C07K 16/28* (2006.01)
*A61K 39/00* (2006.01)
*A61P 27/06* (2006.01)
*A61P 29/00* (2006.01)

(52) U.S. Cl.
CPC .......... *C07K 16/2866* (2013.01); *A61P 27/06* (2018.01); *A61P 29/00* (2018.01); *C07K 16/28* (2013.01); *A61K 2039/505* (2013.01); *C07K 2317/31* (2013.01); *C07K 2317/34* (2013.01); *C07K 2317/622* (2013.01); *C07K 2317/77* (2013.01)

(58) Field of Classification Search
None
See application file for complete search history.

(56) References Cited

U.S. PATENT DOCUMENTS 9,200,074 B2 * 12/2015 Campbell ............... A61P 11/00

FOREIGN PATENT DOCUMENTS

WO  2010052505 A1  5/2010
WO  2015123493 A2  8/2015

OTHER PUBLICATIONS

Iannitti et al. IL-1 receptor antagonist ameliorates inflammasome-dependent inflammation in murine and human cystic fibrosis. Nature Communications. 7: 10791; Published: Mar. 14, 2016 (Year: 2016).*
UniProt Reference P14778 (Year: 1990).*
Brinkmann and Kontermann. The making of bispecific antibodies. MAbs. 9(2): 182-212; Published: Jan. 10, 2017 (Year: 2017).*
Goel et al. Plasticity within the Antigen-Combining Site May Manifest as Molecular Mimicry in the Humoral Immune Response. Journal of Immunology. 173(12): 7358-7367; Published: Dec. 15, 2004 (Year: 2004).*
Lloyd et al. Modelling the human immune response: performance of a 1011 human antibody repertoire against a broad panel of therapeutically relevant antigens. Protein Engineering, Design & Selection. 22(3): 159-168; Published: Oct. 29, 2008 (Year: 2008).*
Edwards et al. The Remarkable Flexibility of the Human Antibody Repertoire; Isolation of Over One Thousand Different Antibodies to a Single Protein, BLyS. Journal of Molecular Biology. 334: 103-118; Nov. 14, 2003 (Year: 2003).*
Calverley et al., "A Randomised, Placebo-Controlled Trial of Anti-Interleukin-1 Receptor 1 Monoclonal Antibody MEDI8968 in Chronic Obstructive Pulmonary Disease," Respir Res., 18(1):153, Aug. 2017.
International Search Report and Written Opinion of the ISA/EP in PCT/EP2019/074745, dated Dec. 13, 2019; 14pgs.
Jeru et al., "Inflammasome and Interleukin 1," La Revue de Medecine Interne, 32(4):218-224, Jun. 2010.
McGilligan et al., "InflaMab: A Novel Inhibitor of Inflammation Targeting the NLRP3 Inflammasome," Ulster University Research Output, accessed on the internet at https://pure.ulster.ac.uk/en/publications/inflamab-a-novel-inhibitor-of-inflammation-targeting-the-nlrp3-in, retrieved Nov. 22, 2019, 2pgs., Aug. 2019.
Swanson et al., "The NLRP3 Inflammasome: Molecular Activation and Regulation to Therapeutics," Nat Rev Immunol., 19(8):477-489, Aug. 2019.

* cited by examiner

*Primary Examiner* — Juliet C Switzer
*Assistant Examiner* — Katherine Ann Holtzman
(74) *Attorney, Agent, or Firm* — Haukaas Fortius PLLC; Michael Haukaas

(57) ABSTRACT

The present disclosure concerns modulators of the NLRP3 inflammasome pathway, in particular an NLRP3 inflammasome modulator which is capable of binding to both of IL-1R1 and NLRP3.

13 Claims, 22 Drawing Sheets

Specification includes a Sequence Listing.

Figure 11:
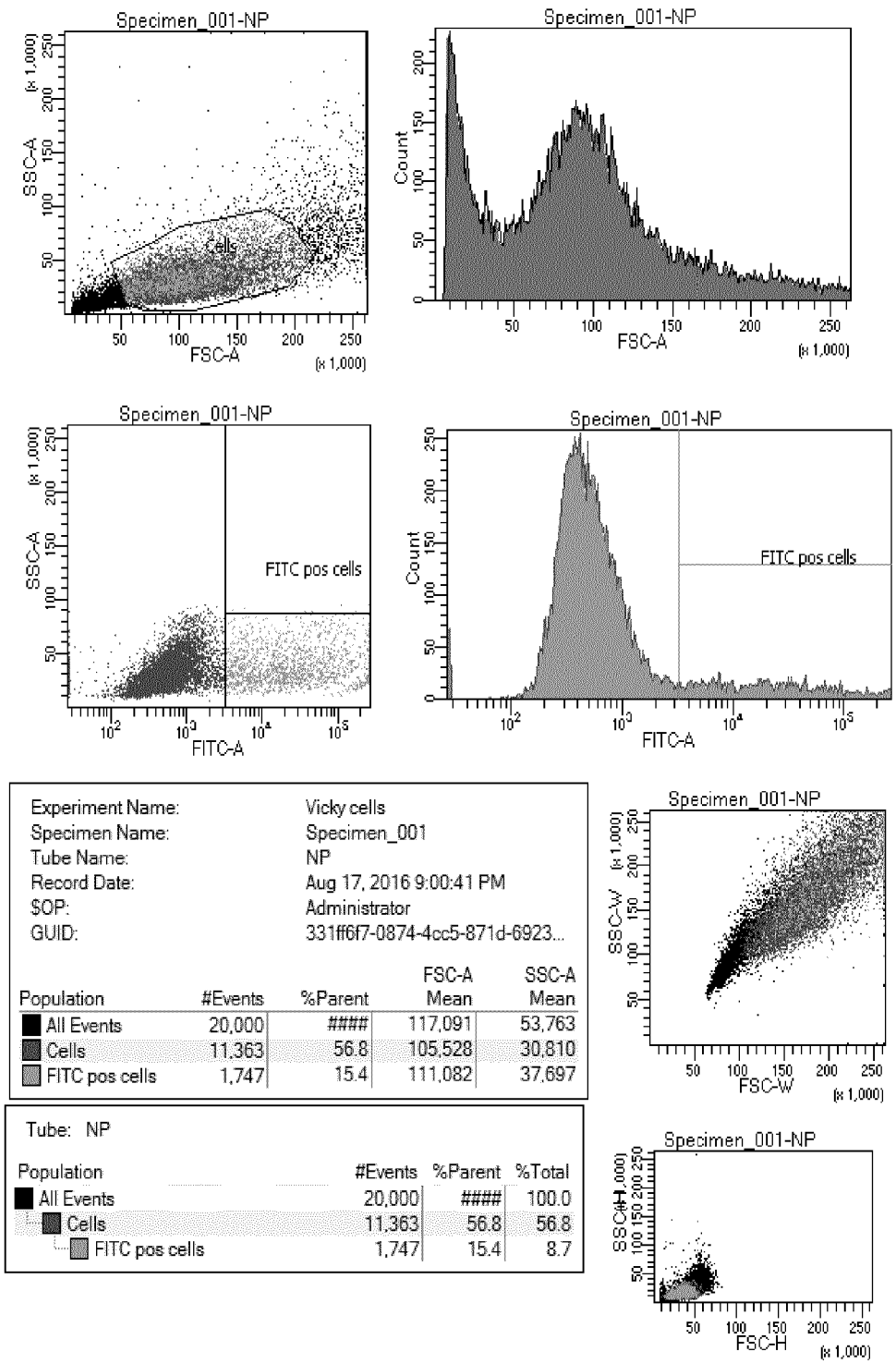

Figure 11 (ii)
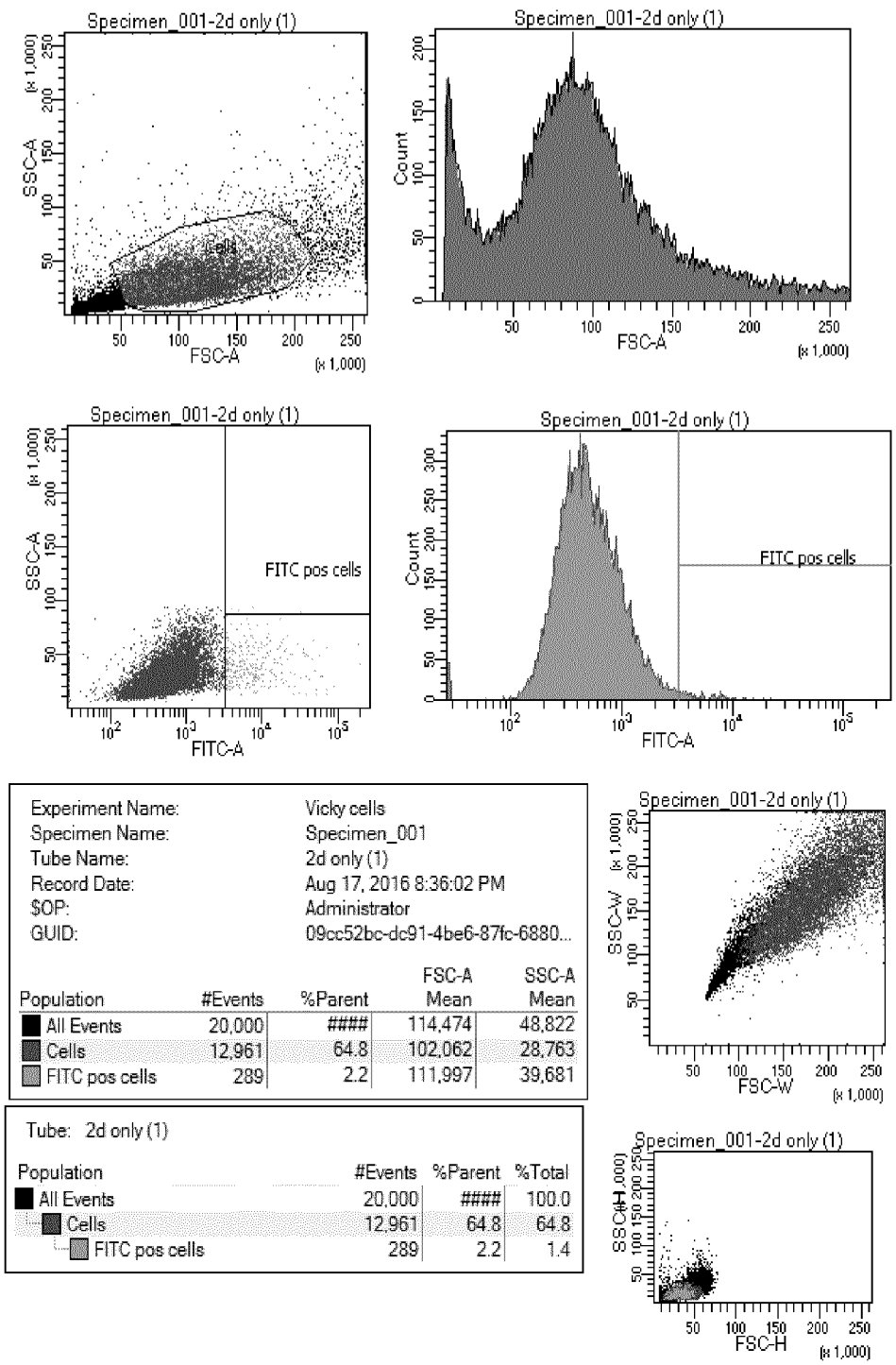

Figure 15:

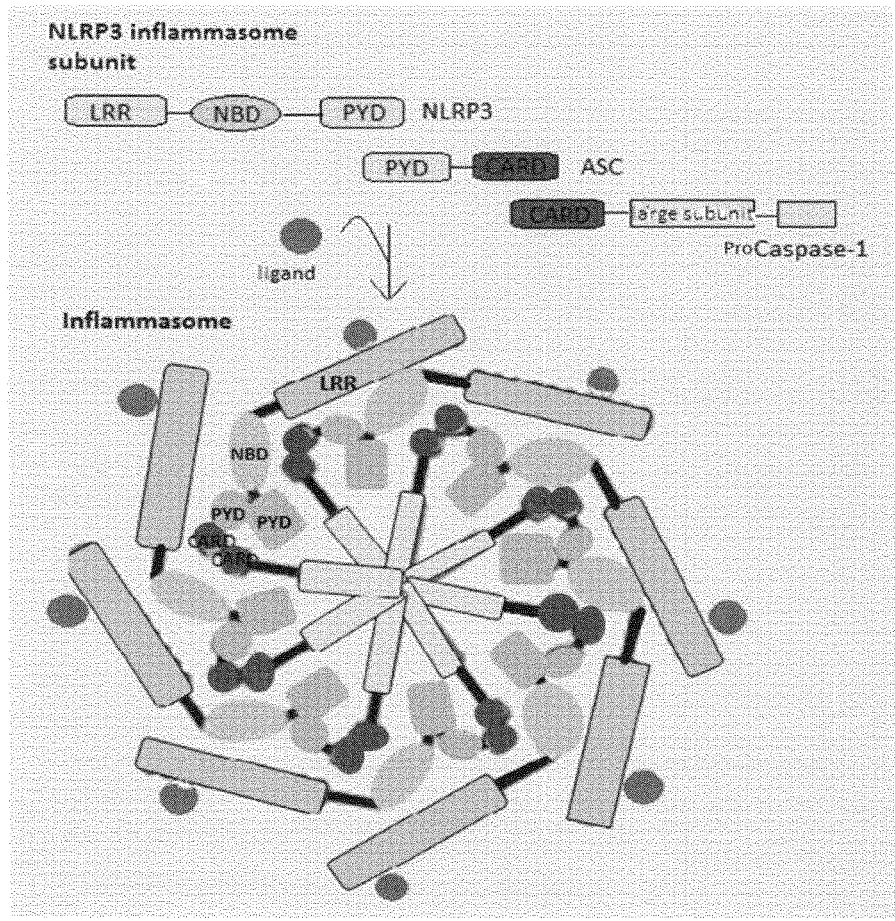

Figure 16:

Sequence Analysis

```
SP|Q96P20|NALP3_HUMAN  KMASTRCKLARYLEDLEDVDLKKFKMHLEDYPPQKGCIPLPRGQTEKADHVDLATLMIDF  61
SP|Q8R4B8|NALP3_MOUSE  -MTSVRCKLAQYLEDLEDVDLKKFKMHLEDYPPEKGCIPVPRGQMEKADHLDLATLMIDF  59
SP|Q9C000|NALP1_HUMAN  MAGGAWGRLACYLEFLKKEELKEFQLLLANKAHSRSSSGETPAQPEKTSGMEVASYLVAQ  60
SP|Q9NX02|NALP2_HUMAN  SSAQMGFNLQALLEQLSQDELSKFKYLITTFSLAHELQKIPHKEVDKADGKQLVEILTTH  62
SP|Q8WX94|NALP7_HUMAN  TSPQLEWTLQTLLEQLNEDELKSFKSLLWAFPLEDVLQKTPWSEVEEADGKKLAEILVNT  61
SP|Q96MN2|NALP4_HUMAN  ASFFSDFGLMWYLEELKKEEFRKFKEHLKQMTLQLELKQIPWTEVKKASREELANLLIKH  62
SP|P59047|NALP5_HUMAN  SLTFSSYGLQWCLYELDKEEFQTFKELLKKKSSESTTCSIPQFEIENANVECLALLLHEY  116
SP|P59046|NAL12_HUMAN  AGRDGLCRLSTYLEELEAVELKKFKLYLGTA-TELGEGKIPWGSMEKAGPLEMAQLLITH  63
SP|Q86W24|NAL14_HUMAN  SSFFPDFGLLLYLEELNKEELNTFKLFLKETM-EPEHGLTPWNEVKKARREDLANLMKKY  65
SP|Q86W28|NALP8_HUMAN  PGSPCENGVMLYMRNVSHEELQRFKQLLLTEL-STGTMPITWDQVETASWAEVVHLLIER  91
SP|Q7RTR0|NALP9_HUMAN  ESFFSDFGLLWYLKELRKEEFWKFKELLKQPLEKFELKPIPWAELKKASKEDVAKLLDKH  62
SP|P59044|NALP6_HUMAN  RLAVARELLLAALEELSQEQLKRFRHKLRDVGPDG--RSIPWGRLERADAVDLAEQLAQF  71
SP|Q86W26|NAL10_HUMAN  KARKPREALLWALSDLEENDFKKLKFYLRDMTLSEGQPPLARGELEGLIPVDLAELLISK  64
SP|P59045|NAL11_HUMAN  ESDSTDFDLLWYLENLSDKEFQSFKKYLARKILDFKL---PQFPLIQMTKEELANVLPIS  59
```

Figure 22:
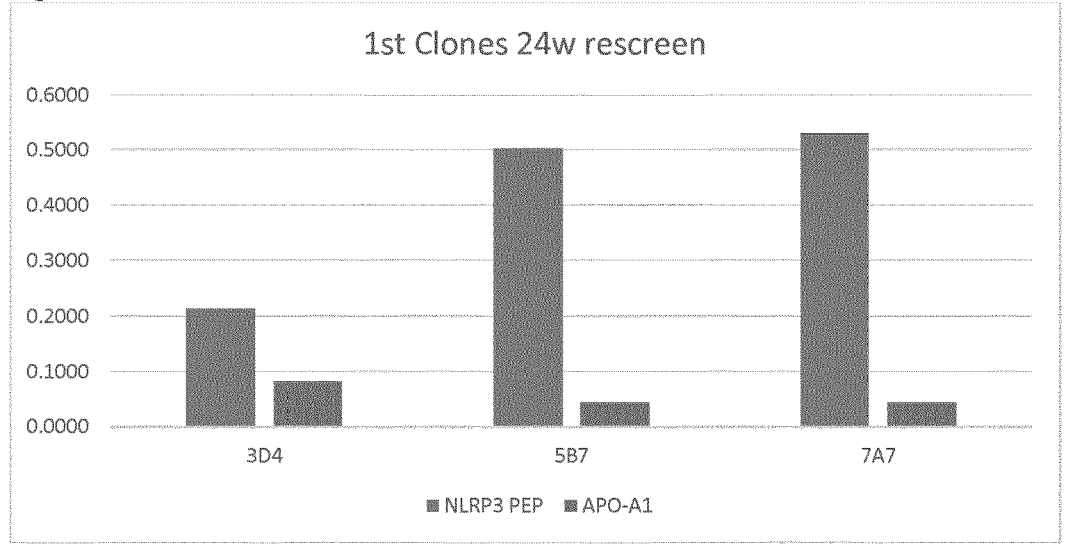
Figure 23:
Figure 24:
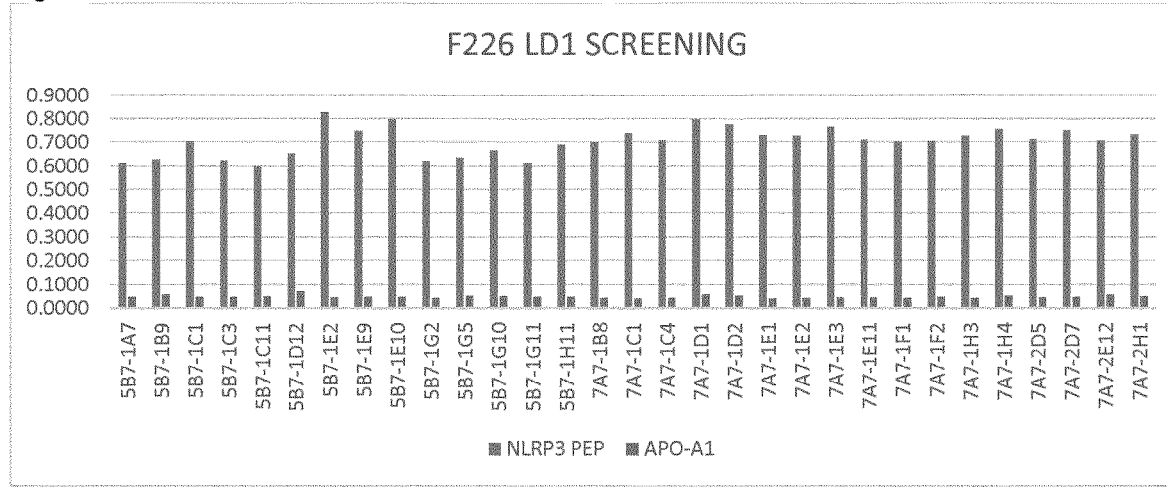

NLRP3
110kDa

βActin
42kDa -

BISPECIFIC ANTIBODY TARGETING IL-1R1 AND NLPR3

CROSS-REFERENCE TO RELATED APPLICATIONS

This application is a National Stage filing under 35 U.S.C. § 371 of International Application No. PCT/EP2019/074745, filed Sep. 16, 2019, which claims the benefit of United Kingdom Patent Application No. 1815045.8 filed Sep. 14, 2018, which applications are incorporated herein by reference.

TECHNICAL FIELD

The present invention relates to modulators of the NLRP3 inflammasome pathway, particularly antibodies and fragments thereof as well as aptamer molecules (small RNA/DNA molecules that can form secondary and tertiary structures capable of specifically binding proteins or other cellular targets), each of which have binding specificity for members of the NLRP3 inflammasome. The invention further extends to use of such antibodies and aptamers, and their fragments, for the treatment and prevention of inflammatory diseases mediated by NLRP3 inflammasome signalling and activation.

BACKGROUND ART

Inflammasomes are a group of protein complexes that recognize a large variety of inflammation inducing stimuli that include pathogen-associated molecular patterns (PAMPs) and danger associated molecular patterns (DAMPs). Different inflammasome complexes are known; among these, NLRP3 is the most studied inflammasome due to the large variety of signals that activate it, including LPS, bacterial toxins, dust, stress signals such as ATP, crystallized and particulate materials, cholesterol crystals, oxidised LDL, amyloid beta, prion protein fibrils and fibrillar alpha synuclein, shear stress, pressure.

The NLRP3 (nucleotide-binding oligomerization domain (NACHT)), leucine rich repeat (LRR) domain, and pyrin domain-containing protein 3 inflammasome is implicated in a number of infectious diseases and a plethora of degenerative inflammatory type diseases including Atherosclerosis, Diabetes, Inflammatory eye disease, other eye diseases such as dry eye syndrome, Glaucoma, Age related macular degeneration, Depression, Alzheimer's Disease, Parkinson's Disease, Inflammatory Bowel Diseases, Arthritic conditions such as Rheumatoid Arthritis, Ageing, Dermatological conditions and Cancer.

The main role of the NLRP3 protein is to sense danger signals or foreign material, and relay the signal to caspase 1 in turn activating the secretion of the pro-inflammatory cytokine IL-1β, which then initiates inflammation in an attempt to protect the body. IL-1β is the most studied of all cytokines because of its central role in the inflammatory process. Although it is useful for the body to activate IL-1β, in many diseases this inflammation can get out of control and be responsible for the pathogenesis of the disease. Most therapeutic strategies to date have concentrated on developing therapies against IL-1β to dampen the inflammation, but as we propose here, there are number of advantages of targeting the upstream controllers of this cytokine, namely the NLRP3 inflammasome.

The mechanism of activation is not yet fully understood, but the processing of IL-1β via the inflammasome has been demonstrated to involve two pathways. First, the NFκB pathway is activated by a DAMP or PAMP via Toll-like receptors (TLRs) and or CD36 receptors. This leads to the transcription and expression of the pro form of IL-1β and NLRP3.

A second signal is also thought to be required whereby purinergic receptor stimulation by a DAMP such as ATP leads to increases in intracellular calcium and cell swelling that results in potassium efflux from the cell, lysosomal destabilisation, membrane permeabillisation, mitochondrial damage and subsequent generation of reactive oxygen species, leading to NLRP3 activation. Other work has demonstrated that oxidized LDL cholesterol can indeed itself act as the two signals required for NLRP3 activation. In all studies, potassium efflux appears to be the sole common denominator for NLRP3 activation.

The NLRP3 protein subsequently interacts with ASC (apoptosis-associated speck-like protein) through homotypic interactions of the pyrin domain. ASC then interacts with pro caspase 1 resulting in cleavage and activation of caspase 1, which in turn cleaves pro IL-1β to its active form. IL-1β is then cleaved to produce the biologically active and secreted form.

The current best treatments for inflammasome-related disorders target the main product of inflammasome activity, IL-1β. In the past 20 years, a number of anti-IL-1β therapies have been developed. However, there are several disadvantages of anti-IL-1β therapies. Host defence against opportunistic organisms as well as routine bacterial infections have become a major concern for all anti-cytokine agents because of the indolent and dangerous nature of these infections. Anti-IL-1β therapies have other side effects such as nausea, neutrophilia and adverse allergic responses.

Some advantages of an anti-NLRP3 therapy over the IL-1β therapies are as follows:

NLRP3 is a nod like receptor so dampening the recognition of the root cause of a disease, i.e. recognition of the foreign/danger material may be advantageous over dampening the response. This would mean that no IL-1β would be secreted via the NLRP3 pathway activated by disease specific stimuli, e.g. oxidized LDL, 1 amyloid or alpha synuclein or a particular pathogen. However, IL-1β could still be activated via other pathways in response to other non-disease-related stimuli as needed in extreme circumstances (such as large scale or opportunistic infections), since there are other pathways responsible for IL-1β activation.

The inflammasome has been associated with specialized forms of cell death, pyronecrosis (caspase1 independent) and pyroptosis, which may occur in cases of exacerbated inflammation. Therefore, an anti-NLRP3 therapy will also decrease such death pathways, which have been evidenced to be involved in the pathogenesis of certain diseases such as atherosclerosis. Pyroptosis is a risk factor for plaque disruption in this disease in response to oxidized LDL.

Several previously characterized small molecule inhibitors have more recently also been shown to affect NLRP3 inflammasome function. Glyburide, a sulfonylurea drug, is an example of such an inhibitor. MCC950 (illustrated below) is another example of a specific small molecule inhibitor of NLRP3 inflammasome:

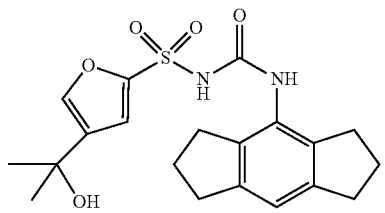 [SMILES: CC(C)(O)c1coc(S(=O)(=O)NC(=O)Nc2c3c(cc4c2CCC4)CCC3)c1]

However, there are several problems with currently available inhibitors. Indeed many of these currently available inhibitors of inflammasome function have either not been clinically successful, are nonspecific and importantly have very short half lives.

The development of humanized antibody type therapy could prove more advantageous than small molecule inhibitors for the NLRP3 inflammasome.

Some advantages of humanized antibodies over small molecule inhibitors are as follows:
  Non-recognition by the human immune system.
  A longer half-life in the circulation than non-human antibodies.
  Higher specificity than small-molecule inhibitors.
  Interact with challenging targets which have thus far eluded small molecule drugs. The best examples of this are protein-protein interactions which are characterised by large and often flat surfaces with few charged pockets.
  Chimeric and humanized mAbs, which have been the predominant mAbs entering clinical studies, have higher approval success rates (18% and 24%, respectively) than new chemical entities (NCEs) including small-molecule agents (5%), especially in the field of oncology.
  The commercial potential of biologics is very promising. The share of biologics in total sales of prescription and over-the-counter medicines grew from 12% in 2004 to 19% in 2011. More interestingly biologic products accounted for 17% of sales of the top 100 pharma products in 2004; 34% in 2011. The global biologics market is estimated to reach nearly $4 bn by 2025.
  Biologics appear to be delivering a better overall economic return than small molecule drugs.
  Studies also show that the rate of attrition for biologics is less than that for small molecules.
  It has been reported that 24.4% of biologics that enter preclinical testing eventually reach the market compared with a success rate of only 7.1% for small molecule drugs.
  Biologics performed better than small molecules at all stages of development with an astonishing 116% rate of success at Phase 2.

NLRP3 (also known as NALP3 and cryopyrin) is a cytosolic protein; therefore, in order to target this protein, any therapy must gain entry to the cell. Humanized antibodies are quite large in size and entry to the cytosol may prove difficult. Small antibody fragment development also present a possibility to overcome such a challenge where an antibody fragment may be a Fab fragment, which is the antigen-binding fragment of an antibody, or a single-chain variable fragment, which is a fusion protein of the variable region of heavy and the light chain of an antibody connected by a peptide linker. As discussed further below, the present inventor has devised additional strategies to ensure the therapeutic antibody or aptamer, and their fragments, can gain entry to the cell.

There are some reports in the field describing the targeting of the NLRP3 inflammasome or related molecules using various agents. For example, WO2013/007763A1 discloses an inhibitor capable of intracellular localisation and cytosolic binding to a member of the inflammasome group including NLRP3, for use in a method for the prevention/treatment of acne.

US20080008652A1 discloses methods and compositions for modulating immune responses and adjuvant activity, and in particular, via modulation of cryopyrin (NPRL3) signalling. Humanized antibodies that target cryopyrin modulating proteins, or cryopyrin signal pathway components, are mentioned, and methods of producing cryopyrin antibodies are disclosed.

WO2002026780A2 discloses antibodies that bind to PAAD-domain containing polypeptides, as well as methods of treating various pathologies, including inflammation, by administering an anti-PAAD antibody. Single chain antibodies, chimeric, bifunctional and humanized antibodies, as well as antigen-binding fragments thereof are also mentioned.

WO2011109459A2 discloses a method of treating an inflammatory disease of skin/hair by providing a composition including at least one antibody that specifically binds to a component(s) of a mammalian inflammasome, such as ASC or NLRP1. Commercially available antibodies to ASC and NPRL1 are mentioned.

EP2350315B1 discloses methods and kits for the early diagnosis of atherosclerosis, involving the measurement of the expression levels of NLRP3, ASC and/or caspase-1. Expression levels may be measured by methods involving antibodies, including human antibodies, humanized antibodies, recombinant antibodies and antibody fragments, which in turn include Fab, Fab', F(ab)2, F(ab')2, Fv and scFv.

WO2013119673A1 discloses a method of evaluating a patient suspected of having a CNS injury comprising measuring the level of at least one inflammasome protein such as NLRP1 (NALP-1), ASC, and caspase-1. Commercially available antibodies to NPRL-1, ASC and caspase-1 are mentioned.

WO2007077042A1 discloses a method for the treatment of gout or pseudogout, comprising administering a NALP3 inflammasome inhibiting agent. The NALP3 inflammasome inhibiting agents are described as acting downstream of the NALP3 inflammasome and selected from among antibodies that inhibit the activity of IL-1.

WO2013138795A1 discloses a fusion protein comprising a Surf+Penetrating Polypeptide and an antibody or antibody-mimic moiety (AAM moiety) that binds to an intracellular target, wherein the fusion protein penetrates cells and binds to the intracellular target to inhibit binding between the target and another protein inside the cells.

The present invention provides novel and effective modulators of the NLRP3 inflammasome. Such modulators include a bi-antibody or aptamer, and their fragments, targeted to both of IL-1R1 and NLRP3. The bi-antibody first gains entry into the cell by binding to the IL-1R1 which triggers rapid internalisation and, once internalised, the bi-antibody then targets the intracellular protein NLRP3 inhibiting the assembly of the NLRP3 inflammasome, in turn preventing IL-1β secretion from the cells, and reducing the initiation/amplification of inflammation.

SUMMARY OF THE INVENTION

Accordingly, in a first aspect of the present invention, there is provided an NLRP3 inflammasome modulator which is capable of binding to both of IL-1R1 and NLRP3.

Optionally, the modulator is also capable of binding to the PYD domain of NLRP3.

Optionally, the modulator is selected from the group comprising: a polyclonal antibody, a monoclonal antibody, a humanized antibody, a chimeric antibody, a fusion protein, or an aptamer molecule, a combination thereof, and fragments of each thereof.

The modulator may be a bi-antibody capable of binding to both of: IL-1R1 and NLRP3. Optionally, the modulator is a recombinant humanized bi-antibody capable of binding to both of: IL-1R1 and NLRP3.

Optionally, the modulator is a bi-antibody comprising one or more of the binding regions of a first antibody capable of binding IL-1R1 and one or more of the binding regions of a second antibody capable of binding NLRP3. Optionally, the modulator is a bi-antibody comprising one or more complementary determining regions (CDRs) of a first antibody capable of binding IL-1R1 and one or more CDRs of a second antibody capable of binding NLRP3. Optionally, the first and/or second antibody is a monoclonal antibody.

Optionally, the modulator is selected from an antibody fragment capable of binding to both: IL-1R1 and NLRP3. Optionally, the antibody fragment is selected from one or more of Fab, Fv, Fab', (Fab')2, scFv, bis-scFv, minibody, Fab2, and Fab3.

Optionally, the modulator is selected from a recombinant humanized antibody or antibody fragment capable of binding to both of: IL-1R1 and NLRP3.

Optionally, the modulator is an antibody or antibody fragment raised against one or more antigens selected from both of IL-1R1 and NLRP3. Optionally, the modulator is raised against one or more antigens selected from all or part of both of IL-1R1 and NLRP3. Optionally, the modulator is raised against one or more antigens selected from NLRP3, optionally conjugated to a carrier protein such as Keyhole Limpet Haemocyanin (KLH) (hereinafter, the NLRP3 immunogen), and IL-1R1, optionally recombinant IL-1R1.

Optionally, the extracellular domain of IL-1R1 (hereinafter, the IL-1R1 immunogen) comprises the sequence:

```
                                         (SEQ ID NO: 1)
MKVLLRLICFIALLISSLEADKCKEREEKIILVSSANEIDVRPCPLNPNE

HKGTITWYKDDSKTPVSTEQASRIHQHKEKLWFVPAKVEDSGHYYCVVRN

SSYCLRIKISAKFVENEPNLCYNAQAIFKQKLPVAGDGGLVCPYMEFFKN

ENNELPKLQWYKDCKPLLLDNIHFSGVKDRLIVMNVAEKHRGNYTCHASY

TYLGKQYPITRVIEFITLEENKPTRPVIVSPANETMEVDLGSQIQLICNV

TGQLSDIAYWKWNGSVIDEDDPVLGEDYYSVENPANKRRSTLITVLNISE

IESRFYKHPFTCFAKNTHGIDAAYIQUYPVTNFQKLEGGPSVFIFPPNIK

DVLMISLTPKVTCVVVDVSEDDPDVQISWFVNNVEVHTAQTQTHREDYNS

TIRVVSHLPIQHQDWMSGKEFKCKVNNKDLPSPIERTISKPKGLVRAPQV

YTLPPPAEQLSRKDVSLTCLVVGFNPGDISVEWTSNGHTEENYKDTAPVL

DSDGSYFIYSKLNMKTSKWEKTDSFSCNVRHEGLKNYYLKKTISRSPG

K*.
(* or ** denotes a stop codon throughout this specification).
```

Optionally, the NLRP3 immunogen comprises the sequence:

```
                                       (SEQ ID NO: 30)
         EDYPPQKGCIPLPRGQTEKADHVD.
```

Optionally, the NLRP3 immunogen comprises a carrier protein conjugated to the sequence EDYPPQKGCIPLPRGQTEKADHVD (SEQ ID NO: 30), optionally conjugated to the N-terminal end of the sequence EDYPPQKGCIPLPRGQTEKADHVD (SEQ ID NO: 30).

A carrier protein, conjugated to a peptide, is known in the art to help the peptide generate a stronger immune response. Optionally, the carrier protein is KLH.

Optionally, the carrier protein is conjugated to the sequence EDYPPQKGCIPLPRGQTEKADHVD (SEQ ID NO: 30) via a linker, optionally the linker is Hydrazide-Ahx.

Optionally, the NLRP3 immunogen is:

```
                                       (SEQ ID NO: 30)
     KLH-Hydrazide-Ahx-EDYPPQKGCIPLPRGQTEKADHVD.
```

As is understood in the art, a hydrazide is a class of organic compounds characterized by a nitrogen-nitrogen covalent bond with four substituents with at least one of them being an acyl group. Ahx denotes a 6-carbon linear aminohexanoic linker.

Optionally, the modulator is raisable, optionally raised, against one or more immunogens selected from NLRP3 immunogen and IL-1R1 immunogen, wherein the IL-1R1 immunogen comprises the sequence:

```
                                         (SEQ ID NO: 1)
MKVLLRLICFIALLISSLEADKCKEREEKIILVSSANEIDVRPCPLNPNE

HKGTITWYKDDSKTPVSTEQASRIHQHKEKLWFVPAKVEDSGHYYCVVRN

SSYCLRIKISAKFVENEPNLCYNAQAIFKQKLPVAGDGGLVCPYMEFFKN

ENNELPKLQWYKDCKPLLLDNIHFSGVKDRLIVMNVAEKHRGNYTCHASY

TYLGKQYPITRVIEFITLEENKPTRPVIVSPANETMEVDLGSQIQLICNV

TGQLSDIAYWKWNGSVIDEDDPVLGEDYYSVENPANKRRSTLITVLNISE

IESRFYKHPFTCFAKNTHGIDAAYIQUYPVTNFQKLEGGPSVFIFPPNIK

DVLMISLTPKVTCVVVDVSEDDPDVQISWFVNNVEVHTAQTQTHREDYNS

TIRVVSHLPIQHQDWMSGKEFKCKVNNKDLPSPIERTISKPKGLVRAPQV

YTLPPPAEQLSRKDVSLTCLVVGFNPGDISVEWTSNGHTEENYKDTAPVL

DSDGSYFIYSKLNMKTSKWEKTDSFSCNVRHEGLKNYYLKKTISRSPG

K*.
(* denotes a stop codon)
``` and the NLRP3 immunogen comprises the sequence:

```
                                       (SEQ ID NO: 30)
     KLH-Hydrazide-Ahx-EDYPPQKGCIPLPRGQTEKADHVD.
```

Optionally, the modulator is a bi-antibody comprising one or more of the binding regions of a first antibody raisable, optionally raised, against IL-1R1 immunogen and comprising the sequence:

(SEQ ID NO: 1)
MKVLLRLICFIALLISSLEADKCKEREEKIILVSSANEIDVRPCPLNPN

EHKGTITWYKDDSKTPVSTEQASRIHQHKEKLWFVPAKVEDSGHYYCVV

RNSSYCLRIKISAKFVENEPNLCYNAQAIFKQKLPVAGDGGLVCPYMEF

FKNENNELPKLQWYKDCKPLLLDNIHFSGVKDRLIVMNVAEKHRGNYTC

HASYTYLGKQYPITRVIEFITLEENKPTRPVIVSPANETMEVDLGSQIQ

LICNVTGQLSDIAYWKWNGSVIDEDDPVLGEDYYSVENPANKRRSTLIT

VLNISEIESRFYKHPFTCFAKNTHGIDAAYIQLIYPVTNFQKLEGGPSV

FIFPPNIKDVLMISLTPKVTCVVVDVSEDDPDVQISWFVNNVEVHTAQT

QTHREDYNSTIRVVSHLPIQHQDWMSGKEFKCKVNNKDLPSPIERTISK

PKGLVRAPQVYTLPPPAEQLSRKDVSLTCLVVGFNPGDISVEWTSNGHT

EENYKDTAPVLDSDGSYFIYSKLNMKTSKWEKTDSFSCNVRHEGLKNYY

LKKTISRSPGK*,
(* denotes a stop codon)

and one or more of the binding regions of a second antibody raised against NLRP3 immunogen comprising the sequence:

(SEQ ID NO: 30)
KLH-Hydrazide-Ahx-EDYPPQKGCIPLPRGQTEKADHVD.

Optionally, the modulator is a bi-antibody comprising one or more complementary determining regions (CDRs) of a first antibody raisable, optionally raised, against IL-1R1 immunogen and comprising the sequence:

(SEQ ID NO: 1)
MKVLLRLICFIALLISSLEADKCKEREEKIILVSSANEIDVRPCPLNPN

EHKGTITWYKDDSKTPVSTEQASRIHQHKEKLWFVPAKVEDSGHYYCVV

RNSSYCLRIKISAKFVENEPNLCYNAQAIFKQKLPVAGDGGLVCPYMEF

FKNENNELPKLQWYKDCKPLLLDNIHFSGVKDRLIVMNVAEKHRGNYTC

HASYTYLGKQYPITRVIEFITLEENKPTRPVIVSPANETMEVDLGSQIQ

LICNVTGQLSDIAYWKWNGSVIDEDDPVLGEDYYSVENPANKRRSTLIT

VLNISEIESRFYKHPFTCFAKNTHGIDAAYIQLIYPVTNFQKLEGGPSV

FIFPPNIKDVLMISLTPKVTCVVVDVSEDDPDVQISWFVNNVEVHTAQT

QTHREDYNSTIRVVSHLPIQHQDWMSGKEFKCKVNNKDLPSPIERTISK

PKGLVRAPQVYTLPPPAEQLSRKDVSLTCLVVGFNPGDISVEWTSNGHT

EENYKDTAPVLDSDGSYFIYSKLNMKTSKWEKTDSFSCNVRHEGLKNYY

LKKTISRSPGK*,
(* denotes a stop codon)

and one or more CDRs of a second antibody raised against NLRP3 immunogen comprising the sequence:

(SEQ ID NO: 30)
KLH-Hydrazide-Ahx-EDYPPQKGCIPLPRGQTEKADHVD.

Optionally, the first and/or second antibody is a monoclonal antibody.

Optionally, the consensus sequence of the heavy chain of the first antibody (to IL-1R1) is (SEQ ID NO: 7)
MGWVWNLPFLMAAAQSIQAQIQLVQSGPELRKPGETVRISCKASGYPFTT

AGLQINVQKMSGKGLKWIGWMNTQSEVPKYAEEFKGRIAFSLETAASTAY

LQINNLKTEDTATYFCAKSVYFNWRYFDVWGAGTTVTVSSAKTTPPPVYP

LA.

Optionally, the heavy chain CDRs of the first antibody comprise:

(SEQ ID NO: 60)
GYPFTTAG;

(SEQ ID NO: 61)
MNTQSEVP;
and (SEQ ID NO: 62)
AKSVYFNWRYFDV.

Optionally, the consensus sequence of the light chain of the first antibody (to IL-1R1) is (SEQ ID NO: 12)
MRSPAQFLGLLLFWTSASRCDIVMTQSPATLSVTPGDRVSLSCRASQSI

SDYLSWYQQRSHESPRLIIKYASQSISGIPSRFSGSGSGSDFTLSINSV

EPEDVGVYYCQHGHSFPLTFGSGTKLELKRADAAPTVSIFPPSSEQLTS

GGASVVCFLNNFYPK.

Optionally, the light chain CDRs of the first antibody comprise:

(SEQ ID NO: 63)
QSISDY;

YAS;
and (SEQ ID NO: 64)
QHGHSFPLT.

Optionally, the consensus sequence of the heavy chain of the second antibody (against NLRP3) is (SEQ ID NO: 36)
MDFGLSWVFLVLVLKGVQCEVQLVESGGGLVKPGGSLKLSCAASGFTFS

DYYMYWVRQTPEKRLEWVATISDGGTYTYYPDSVKGRFTISRDNAKNNL

YLQMNSLKSEDTAMYYCARGWVSTMVKLLSSFPYWGQGTLVTVSAAKTT

PPSVYPLA.

Optionally, the heavy chain CDRs of the second antibody comprise:

GFTFSDYY; (SEQ ID NO: 65)

ISDGGTYT; (SEQ ID NO: 66)
and

ARGWVSTMVKLLSSFPY. (SEQ ID NO: 67)

Optionally, the consensus sequence of the light chain of the second antibody (to NLRP3) is (SEQ ID NO: 43)
MAWISLLLSLLALSSGAISQAVVTQESALTTSPGETVTLTCRSSTGAVT

TSNYANWVQEKPDHLFTGLIGGTNNRAPGVPARFSGSLIGDKAALTITG

AQTEDEAIYFCALWYSNYWVFGGGTKLTVLGQPKSSPSVTLFPPSTEEL

SL.

Optionally, the light chain CDRs of the second antibody comprise:

TGAVTTSNY; (SEQ ID NO: 68)

GTN; 
and

ALWYSNYWV. (SEQ ID NO: 69)

Optionally, the modulator is capable of binding simultaneously to IL-1R1 and NLRP3. Optionally, or additionally, the modulator is capable of binding sequentially to IL-1R1 and NLRP3.

Optionally, the light chain of a bi-specific antibody of the present invention has the amino acid sequence:

(SEQ ID NO: 57)
MVSSAQFLGLLLLCFQGTRCDIVMTQSPATLSVTPGDRVSLSCRASQSI

SDYLSWYQQRSHESPRLIIKYASQSISGIPSRFSGSGSGSDFTLSINSV

EPEDVGVYYCQHGHSFPLTFGSGTKLELKRADAAPTVSIFPPSSEQLTS

GGASVVCFLNNFYPKDINVKWKIDGSERQNGVLNSWTDQDSKDSTYSMS

STLTLTKDEYERHNSYTCEATHKTSTSPIVKSFNRNEC**.

Optionally, the heavy chain of a bi-specific antibody of the present invention has the amino acid sequence:

(SEQ ID NO: 59)
MGWTLVFLFLLSVTAGVHSQIQLVQSGPELRKPGETVRISCKASGYPFT

TAGLQWVQKMSGKGLKWIGWMNTQSEVPKYAEEFKGRIAFSLETAASTA

YLQINNLKTEDTATYFCAKSVYFNWRYFDVWGAGTTVTVSSAKTTAPSV

YPLAPVCGDTTGSSVTLGCLVKGYFPEPVTLTWNSGSLSSGVHTFPAVL

QSDLYTLSSSVTVTSSTWPSQSITCNVAHPASSTKVDKKIEPRGPTIKP

CPPCKCPAPNLLGGPSVFIFPPKIKDVLMISLSPIVTCVVVDVSEDDPD

VQISWFVNNVEVHTAQTQTHREDYNSTLRVVSALPIQHQDWMSGKEFKC

-continued

KVNNKDLPAPIERTISKPKGSVRAPQVYVLPPPEEEMTKKQVTLTCMVT

DFMPEDIYVEWTNNGKTELNYKNTEPVLDSDGSYFMYSKLRVEKKNWVE

RNSYSCSVVHEGLHNHHTTKSFSRTPGKGSAGGSGGDSEVQLVESGGGL

VKPGGSLKLSCAASGFTFSDYYMYWVRQTPEKRLEWVATISDGGTYTYY

PDSVKGRFTISRDNAKNNLYLQMNSLKSEDTAMYYCARGWVSTMVKLLS

SFPYWGQGTLVTVSAGGGGSGGGGSGGGGSQAVVTQESALTTSPGETVT

LTCRSSTGAVTTSNYANWVQEKPDHLFTGLIGGTNNRAPGVPARFSGSL

IGDKAALTITGAQTEDEAIYFCALWYSNYWVFGGGTKLTVLGQPK**.

By "binding simultaneously" to both of IL-1R1 and NLRP3, it is meant that the modulator is capable of binding to each of IL-1R1 and/or NLRP3, whether said IL-1R1 and/or NLRP3 are formed as a complex, or whether they are not formed as a complex.

In a second aspect, the invention provides a modulator as defined herein for use in the treatment or prophylaxis of an inflammation-related disorder in which the NLRP3 inflammasome is known to play a key role in the disease pathogenesis.

An advantage of the bispecific antibody as the modulator is that it can be used at lower, and thus less toxic, concentrations than single antibodies, therefore, reducing cytotoxicity potential. Being bi-specific allows for a more stable antibody with greater purity.

Being a biological has a longer half live thus confers a major advantage over small molecule inhibitors.

In a third aspect, the present invention provides a method for the treatment and/or prophylaxis of an inflammation-related disorder, the method comprising the steps of:
providing a therapeutically effective amount of a modulator of the first aspect of the invention which suppresses activation and/or signalling of the NLRP3 inflammasome, and
administering the therapeutically effective amount of said compound to a subject in need of such treatment.

In a fourth aspect, the present invention provides for use of the modulator of the first aspect of the invention in the preparation of a medicament for the treatment of an inflammation-related disorder.

In a fifth aspect, the present invention provides a method to reduce or prevent or treat at least one symptom of an inflammation-related disorder in a subject comprising selectively inhibiting and/or reducing activation of the inflammasome pathway by the use of modulator of the first aspect of the invention.

Optionally, the modulator is for use in the treatment or prevention of at least one symptom of an inflammation-related disorder in a subject comprising selectively inhibiting and or reducing activation of the inflammasome pathway by the use of modulator of the first aspect of the invention.

Optionally, InflaMab may have disease modifying effects in systemic conditions such as but not limited to Atherosclerosis, whereby it prevents/inhibits inflammation therefore preventing plaque build up and/or plaque rupture thus reducing risk of myocardial infarction.

Optionally, InflaMab may have disease modifying effects in eye diseases such as but not limited to Glaucoma, whereby it prevents/inhibits inflammation, reduces intraocular pressure and/or prevents loss of retinal ganglion cells and axons, protecting the optic nerve and preserving visual acuity, and/or preventing blindness.

Optionally, InflaMab may have disease modifying effects in neurological conditions such as but not limited to Alzheimer's Disease, whereby it prevents/inhibits inflammation, reduces/inhibits amyloid plaque load, and/or prevents of cognitive dysfunction.

The modulator of the first aspect of the invention may have utility in individuals with multi-morbidities or co-morbidities associated with inflammation.

Optionally, the modulator of any of the aforementioned aspects of the invention, denoted as Inflamab, is a 210 kiloDalton (kDa) bispecific mouse antibody composed of two pairs of light chain and two pairs of heavy chains with scFv domains fused to the N-terminal, complexed together via disulphide bonds.

As used herein, an "inflammation-related disorder" includes, but is not limited to, Atherosclerosis, inflammatory eye conditions such as Age-Related Macular degeneration, Dry Eye Syndrome, Glaucoma, Sjogren's syndrome, Diabetes, Inflammatory eye disease, Depression, Alzheimer's Disease, Parkinson's Disease, Inflammatory Bowel Disease, Rheumatoid Arthritis, Ageing, Dermatological conditions and Cancer.

Optionally, the subject is a mammal, such as a human.

The term "antibody" should be construed as covering any binding member or substance having a binding domain with the required specificity. The antibody of the invention may be a monoclonal antibody, or a fragment, functional equivalent or homologue thereof. The term includes any polypeptide comprising an immunoglobulin binding domain, whether natural or wholly or partially synthetic. Chimeric molecules comprising an immunoglobulin binding domain, or equivalent, fused to another polypeptide are therefore included.

Fragments of a whole antibody can perform the function of antigen binding. Examples of such binding fragments are; a Fab fragment comprising of the VL, VH, CL and CH1 antibody domains; an Fv fragment consisting of the VL and VH domains of a single antibody; a F(ab')2 fragments, a bivalent fragment comprising two linked Fab fragments; a single chain Fv molecule (scFv), wherein a VH domain and a VL domain are linked by a peptide linker which allows the two domains to associate to form an antigen binding site; or a bi- or tri-specific antibody, which may be multivalent or multispecific fragments constructed by gene fusion.

A fragment of an antibody or of a polypeptide for use in the present invention, generally means a stretch of amino acid residues of at least 5 to 7 contiguous amino acids, often at least about 7 to 9 contiguous amino acids, typically at least about 9 to 13 contiguous amino acids, more preferably at least about 20 to 30 or more contiguous amino acids and most preferably at least about 30 to 40 or more consecutive amino acids.

The term "antibody" includes antibodies which have been "humanized". Methods for making humanised antibodies are known in the art.

Aptamers are peptide molecules that bind to specific target molecules. Aptamers are in the realm between a small molecule and a biologic. They exhibit significant advantages relative to antibody therapeutics in terms of size, synthetic accessibility and modification.

Modulators as described herein may be used in assays, such as ELISAs, to detect NLRP3 from human blood or tissue samples. Thus, in a further aspect, the present invention provides a kit comprising one or more modulators of the first aspect of the invention. Optionally, the kit further comprises instructions for use of said kit. Optionally, the kit is for detecting NLRP3 in human cells, in blood or tissue samples.

IN THE DRAWINGS

Figure 1:
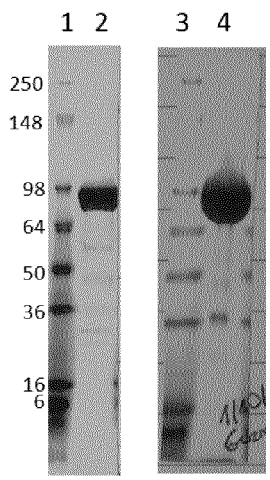

FIG. 1: 4-20% denaturing, reducing and non-reducing, SDS-PAGE analysis of IL-1R1 FC. Molecular weight marker shown in kiloDaltons.

Figure 2:
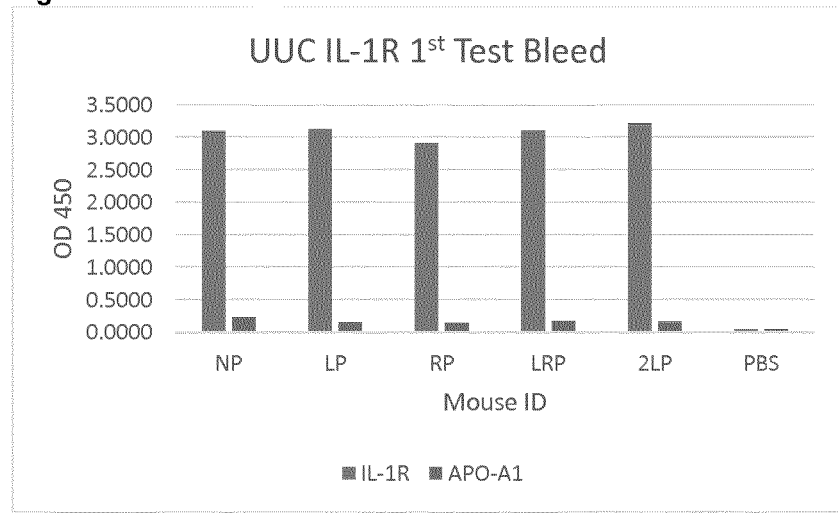

FIG. 2: UUC IL-1R $1^{st}$ Bleed.

Figure 3:
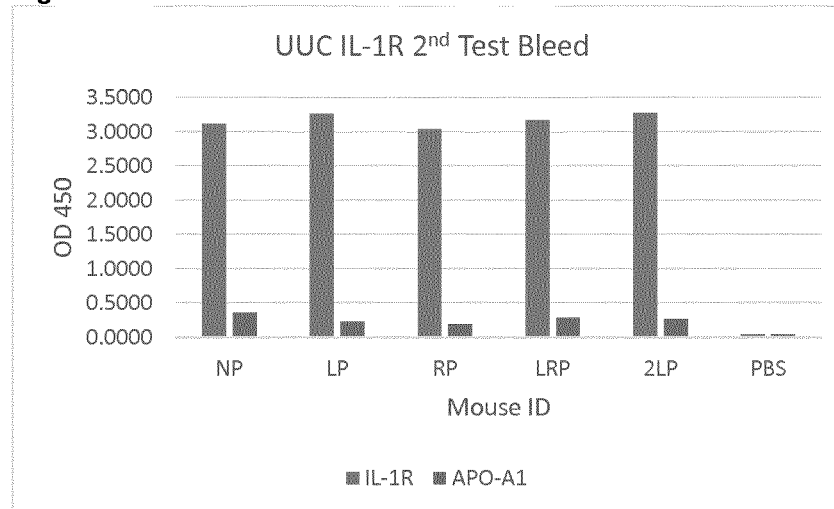

FIG. 3: UUC IL-1R $2^{nd}$ Bleed.

Figure 4:
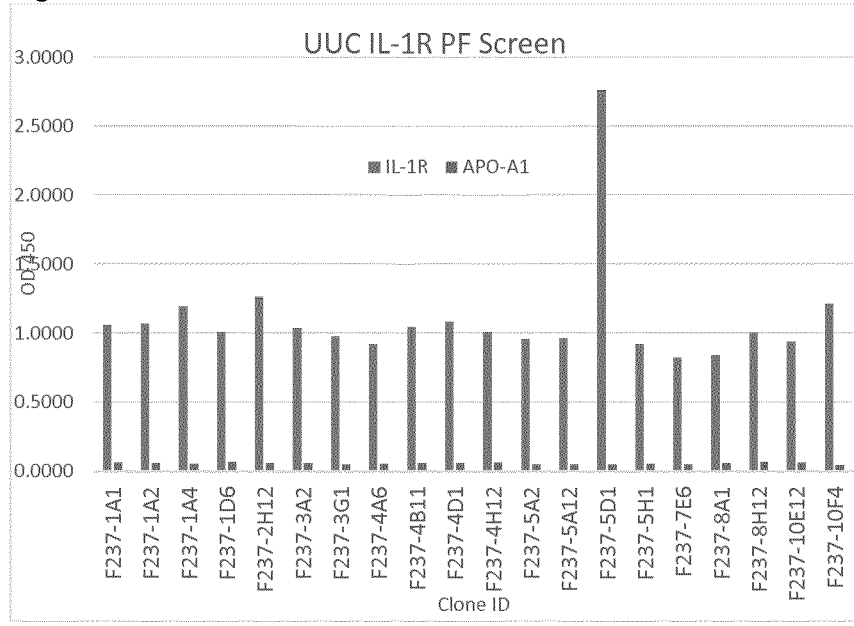

FIG. 4: Post Fusion Screening Results.

Figure 5:
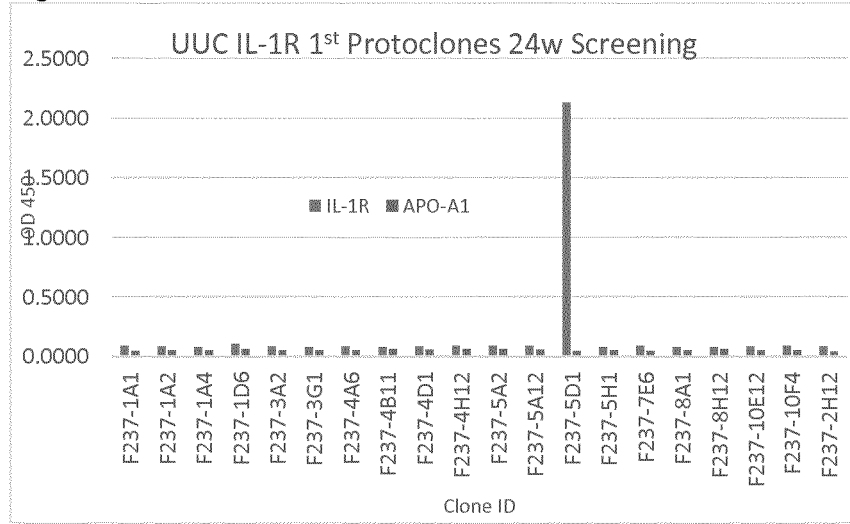

FIG. 5: $1^{st}$ Protoclones 24 well.

Figure 6:
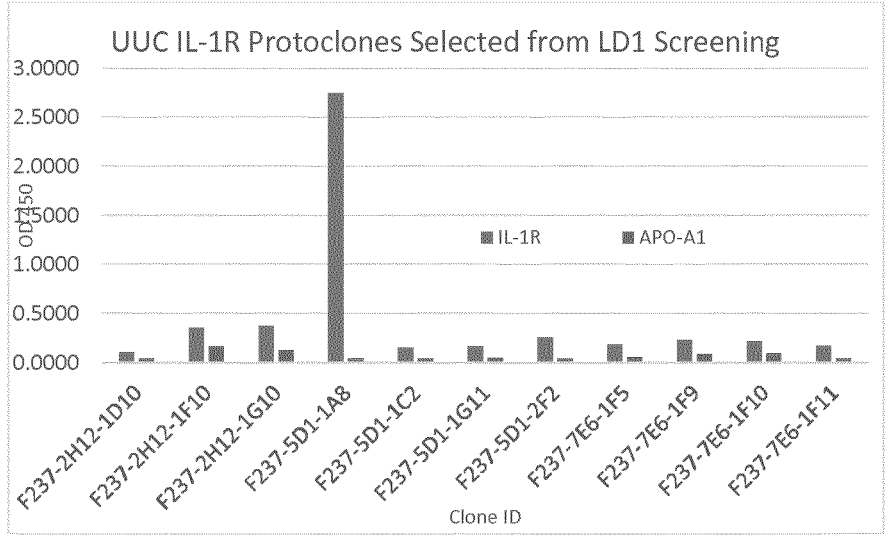

FIG. 6: LD1 Screening Results.

Figure 7:
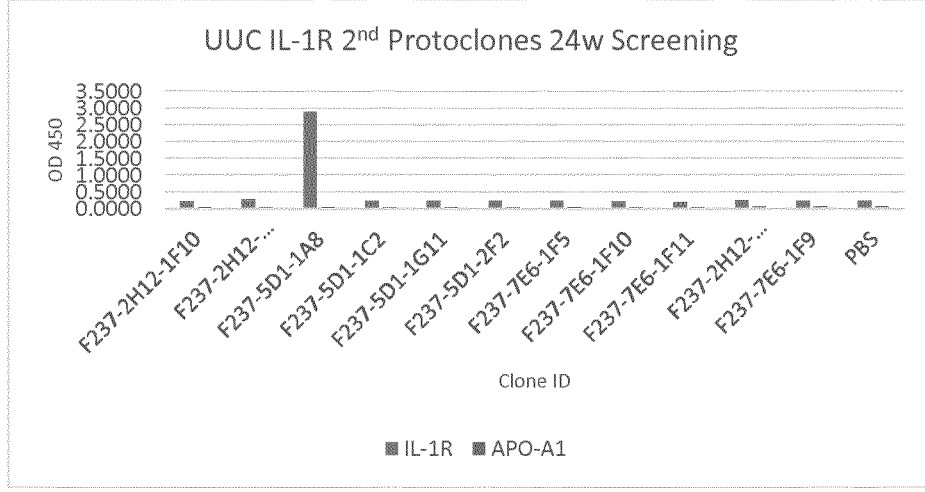

FIG. 7: 24 Well-Plate Screening Results.

Figure 8:
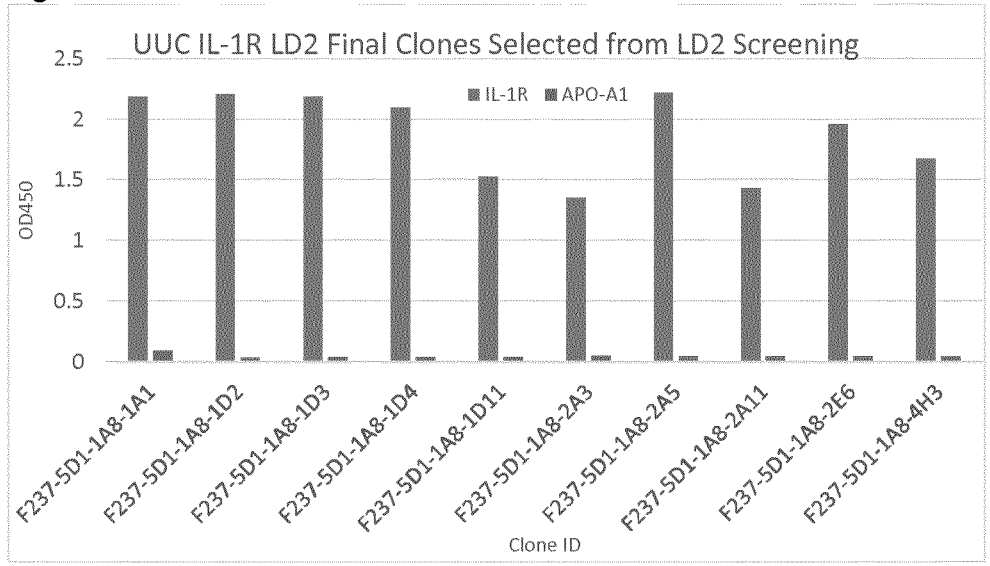

FIG. 8: Final Selected Hybridomas from F237 5D1-1A8.

Figure 9:
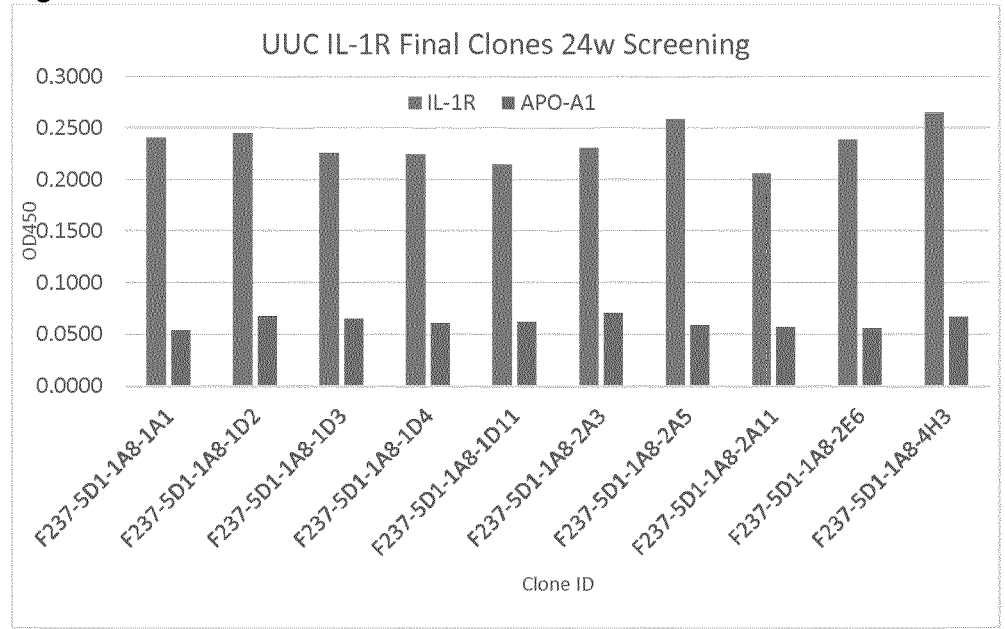

FIG. 9: Final Selected Hybridomas from F237 5D1-1A8 final 24w Screening.

Figure 10:
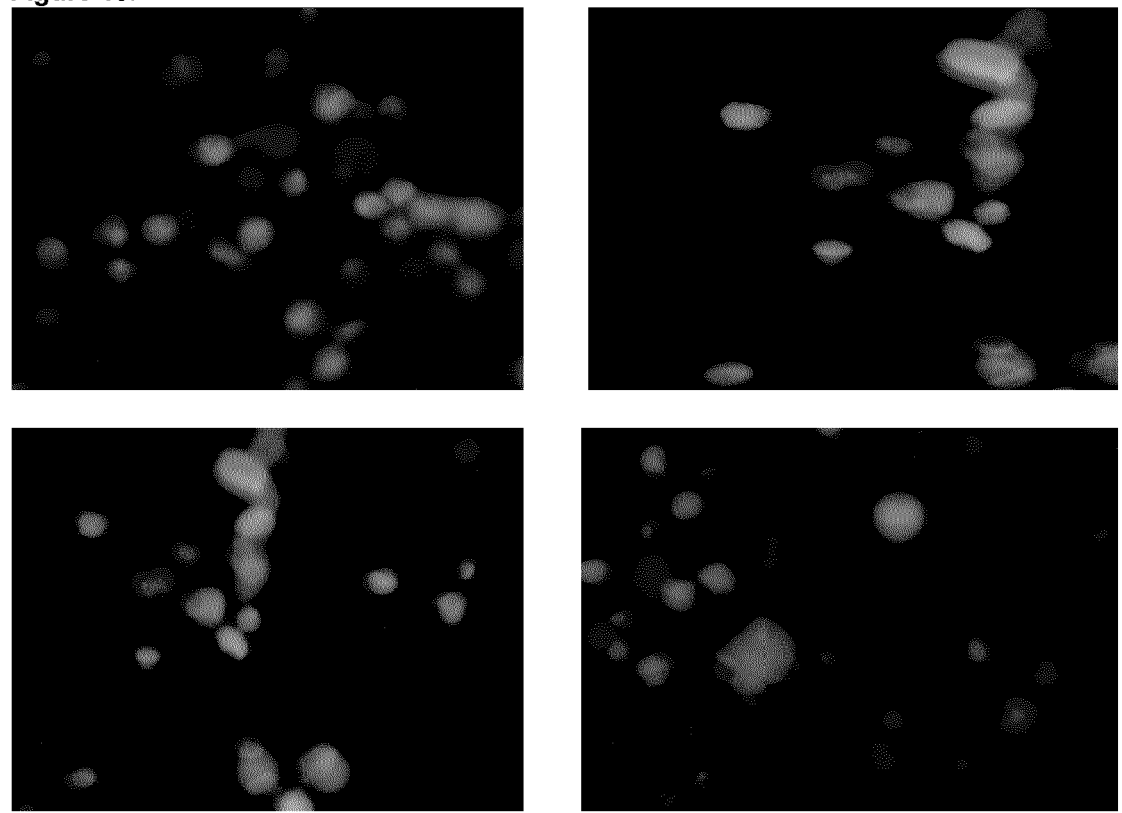

FIG. 10: IL-1R1 Internalisation in THP1 cells—immunofluorescence imaging. Fluorescence microscopic images taken from THP1 macrophages treated with LPS and ATP to induce the expression of the IL-1R1.

FIG. 11: IL-1R1 Internalisation in THP1 cells—flow cytometry.

Figure 12:
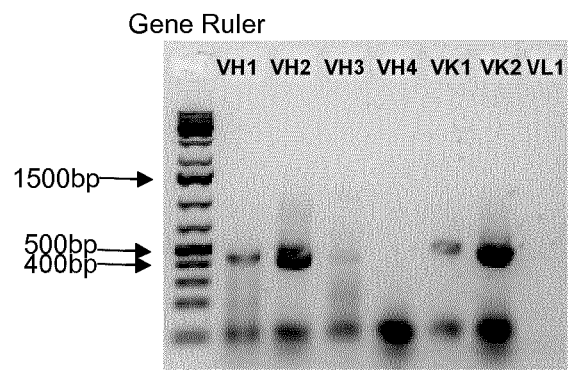

FIG. 12: PCR using several combinations of Ig variable domain primers.

Figure 13:
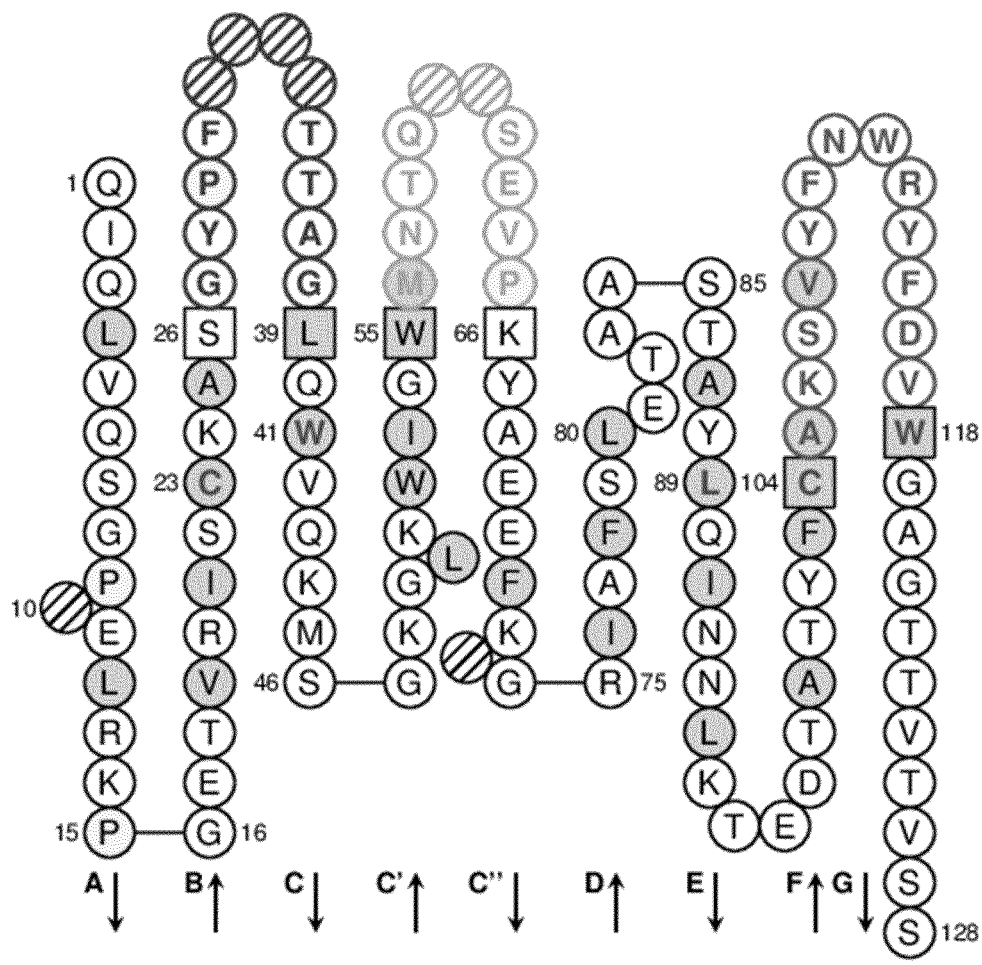

FIG. 13: Graphical representation of the CDR loops. Ref: Lefranc, M.-P. et al., Dev. Comp. Immunol., 27, 55-77 (2003) PMID: 12477501).

Figure 14:
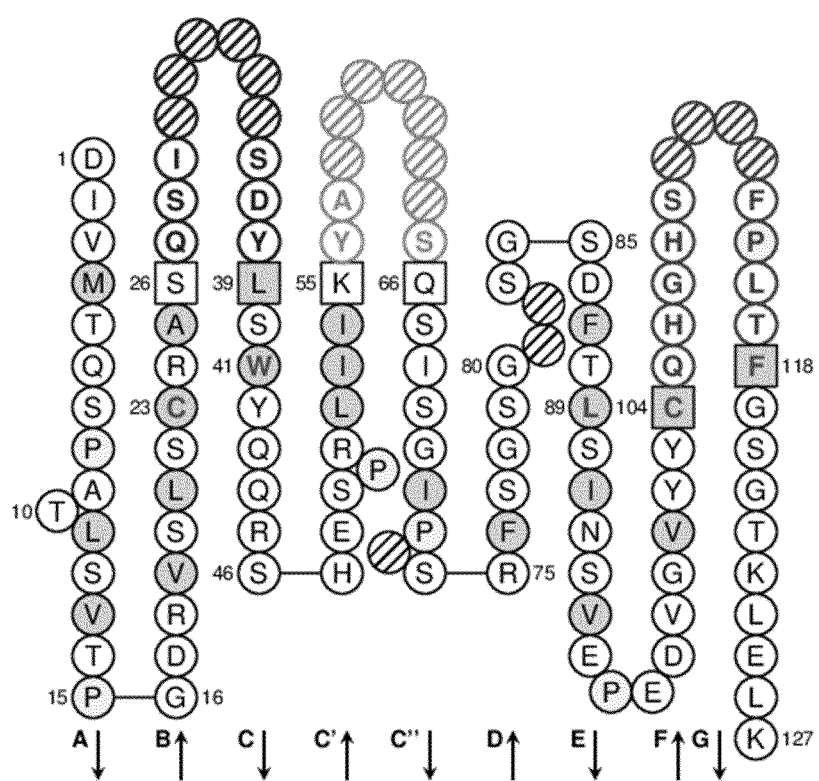

FIG. 14: Graphical representation of the CDR loops (Lefranc, M.-P. et al., Dev. Comp. Immunol., 27, 55-77 (2003) PMID: 12477501).

FIG. 15: Structure of NLRP3 inflammasome. Bergsbaken, T.; Fink, S. L.; Cookson, B. T. (2009). "Pyroptosis: Host cell death and inflammation". Nature Reviews Microbiology. 7 (2): 99-109. doi:10.1038/nrmicro2070. PMC 2910423. PMID 19148178. and Dagenais, M.; Skeldon, A.; Saleh, M. (2011). "The inflammasome: In memory of Dr. Jurg Tschopp". Cell Death and Differentiation. 19 (1): 5-12. doi:10.1038/cdd.2011.159. PMC 3252823. PMID 22075986. http://jonlieffmd.com/blog/cellular-intelligence-blog/inflammasomes-are-large-complex-signaling-platforms FIG. 16: Sequence alignment using CLUSTAL 0 (1.2.4) of the consensus sequences of C-term domains of human and mouse NALP (NLRP) proteins.

Figure 17:
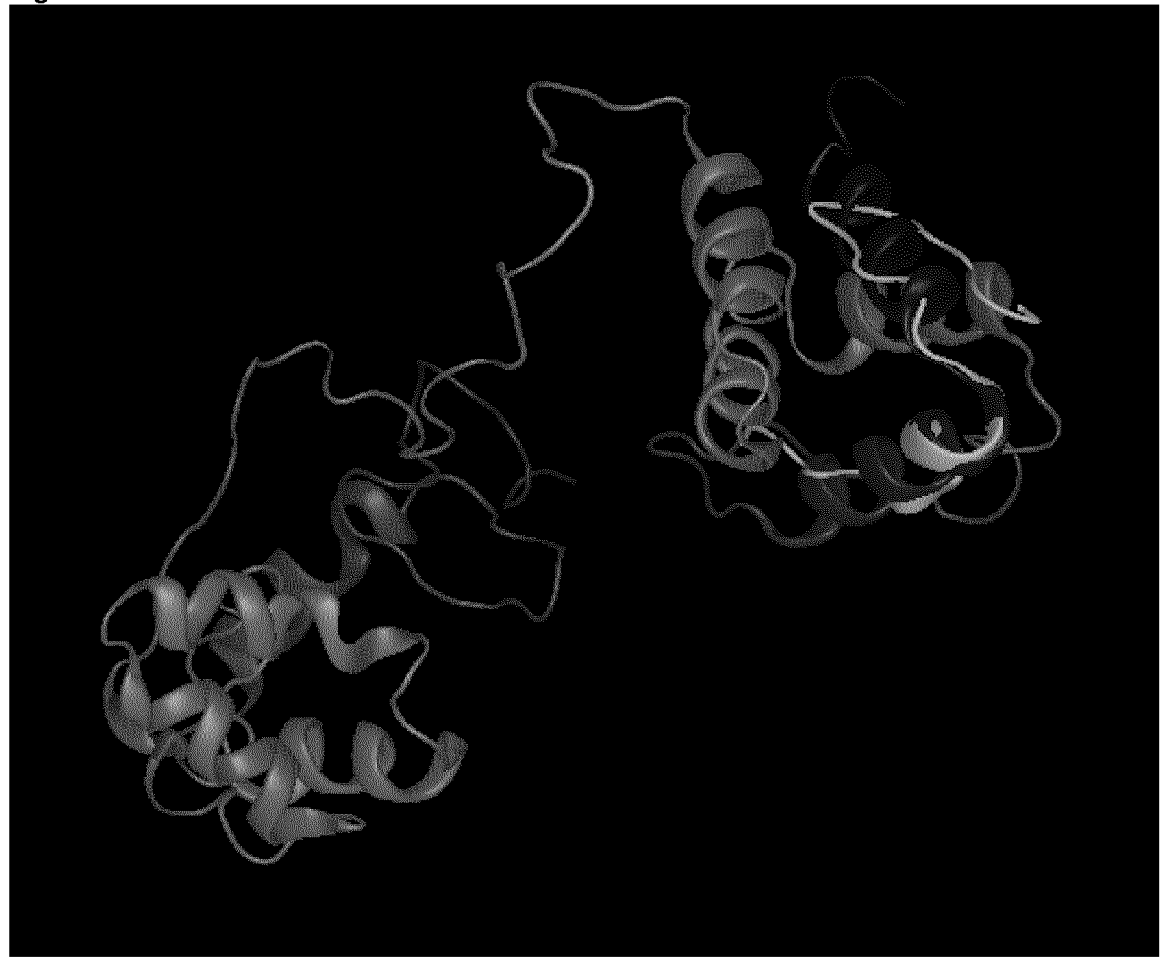

FIG. 17: Novafold predicted structure of Peptide FUS_746_001 (Yellow) aligned to NLRP3 PDB: 3QF2 showing secondary structural features using Protean 3D, version 14.0.1

Figure 18:
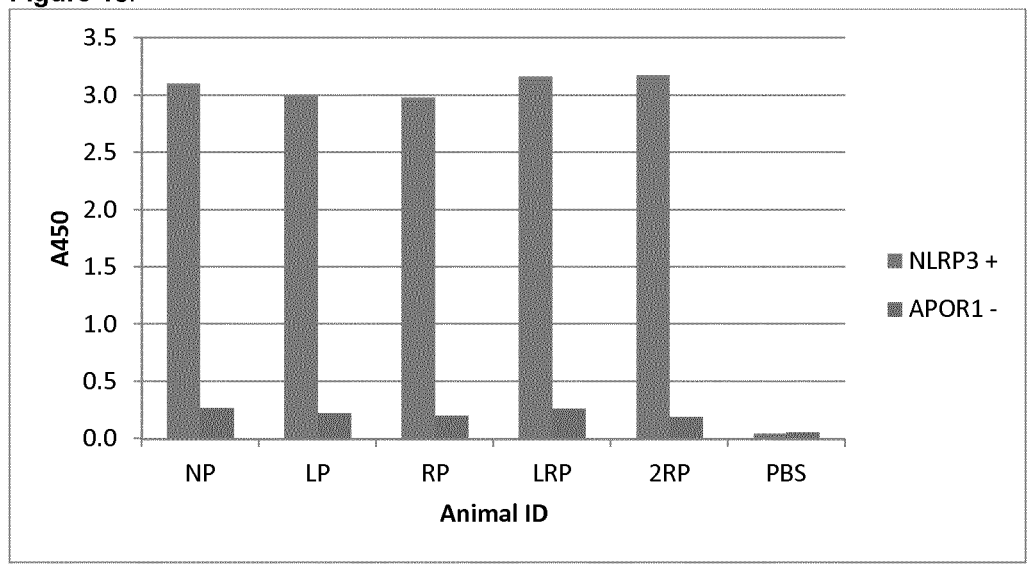

FIG. 18: Immunized mice expressed high levels of the NLRP3 mAb.

Figure 19:
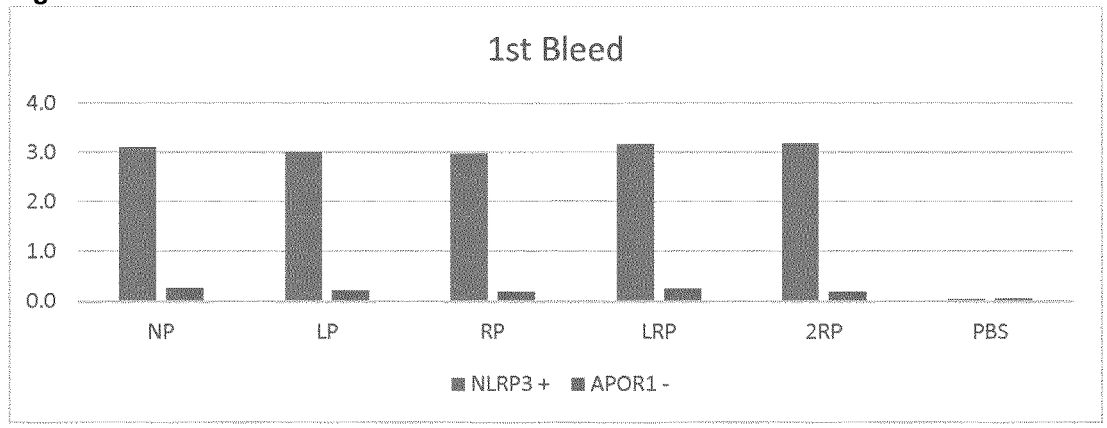

FIG. 19: UUC NLRP3 $1^{st}$ Bleed.

Figure 20:
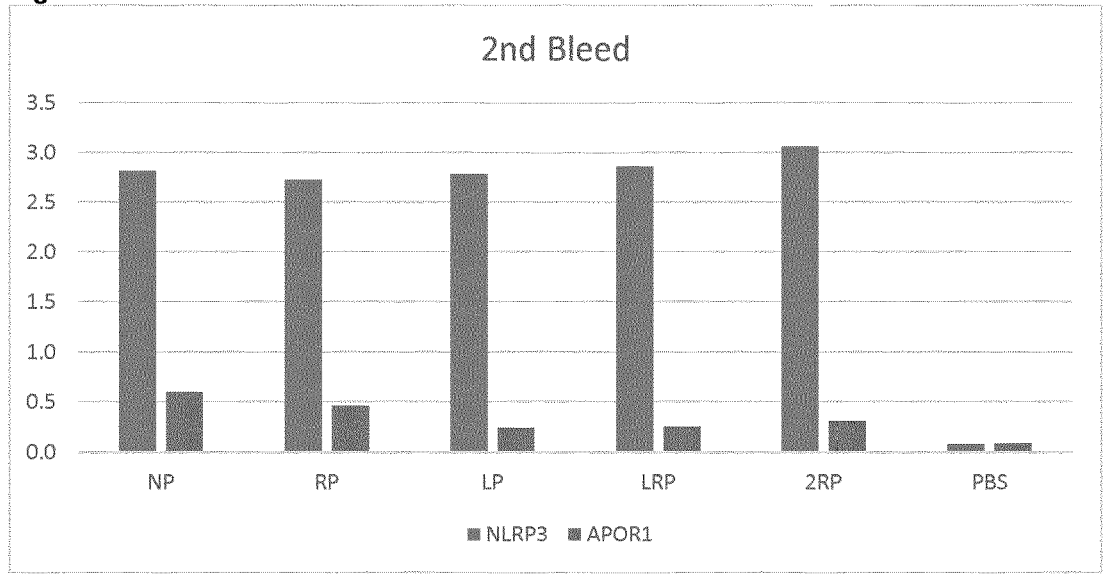

FIG. 20: UUC NLRP3 $2^{nd}$ Bleed.

Figure 21:
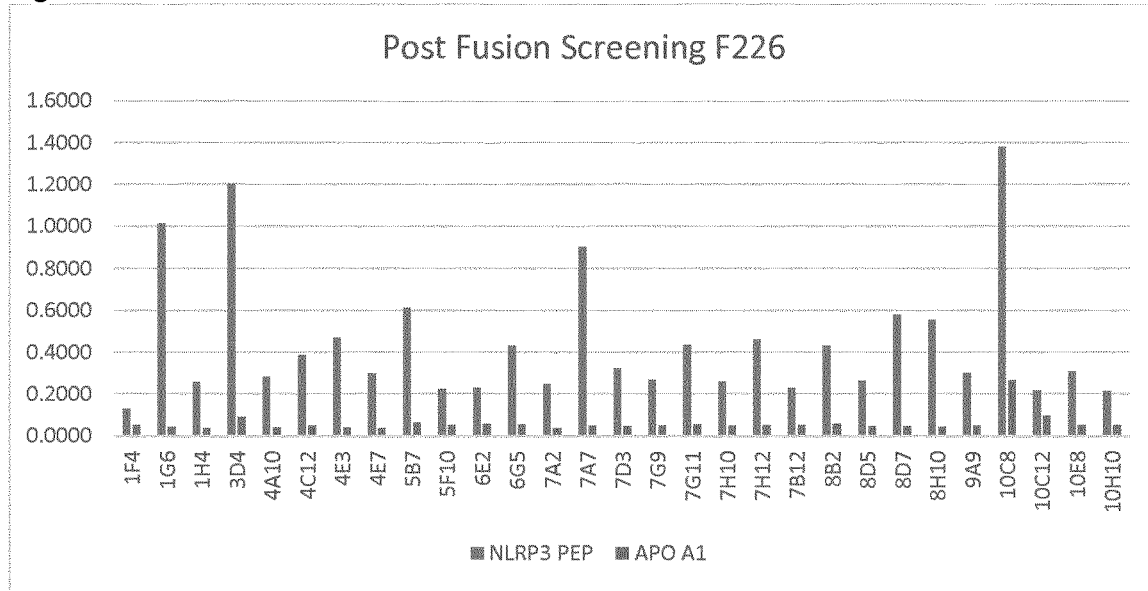

FIG. 21: Post Fusion Screening Results.

FIG. 22: $1^{st}$ Protoclones 24 well.

FIG. 23: LD1 Screening Results.

FIG. 24: 24 Well-Plate Screening Results.

Figure 25:
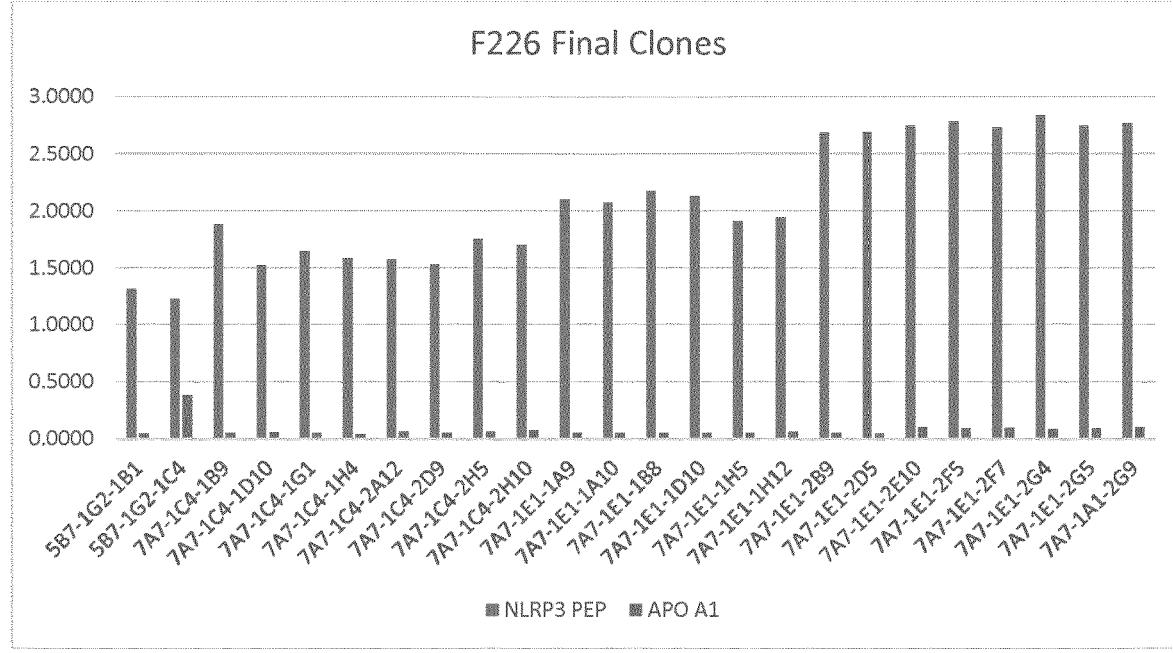

FIG. 25: Final Selected Hybridomas from F226.

Figure 26:
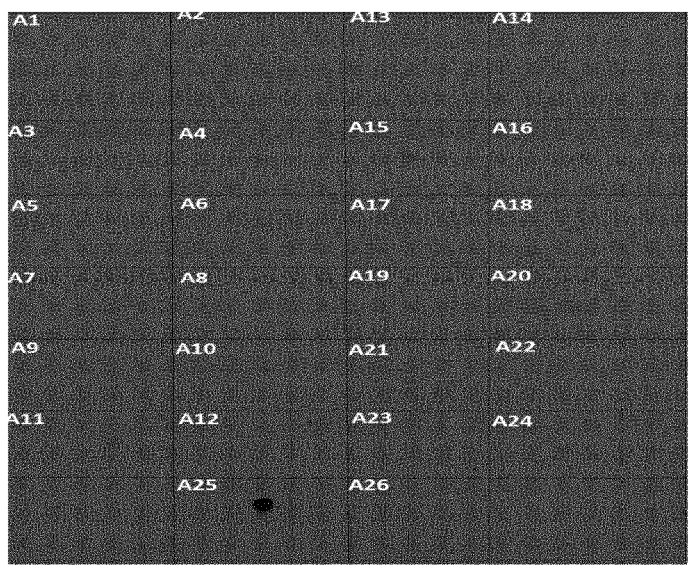

FIG. 26: Dot Blot analysis.

Figure 27:
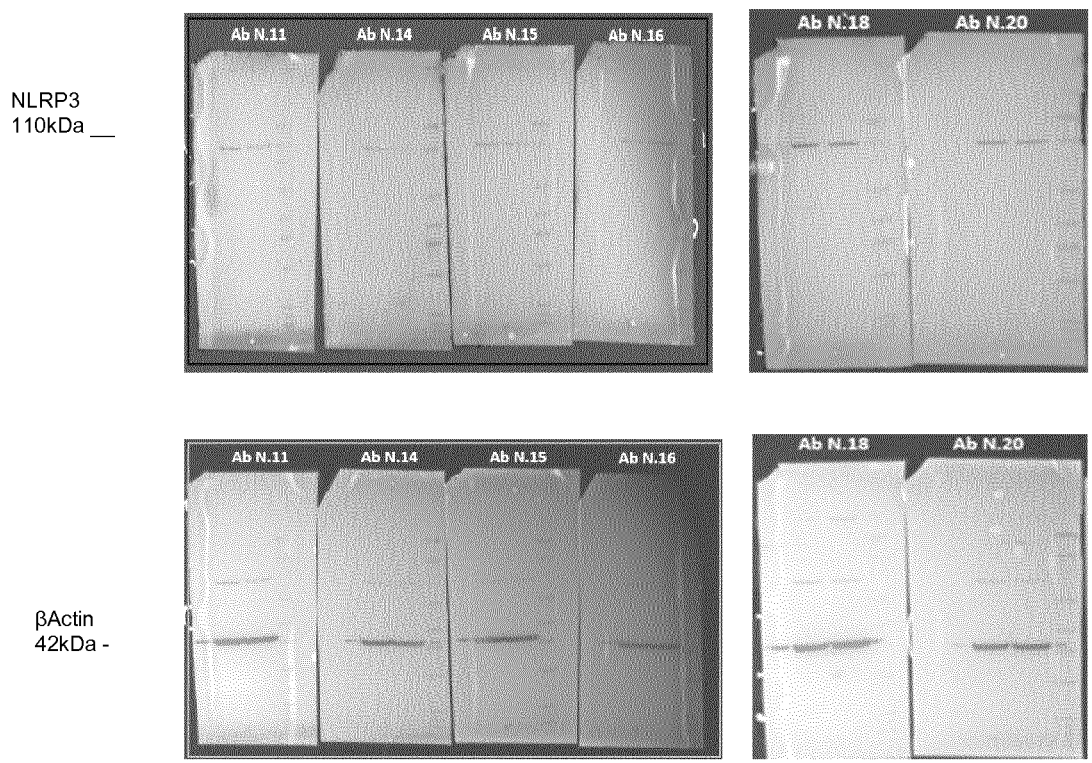

FIG. 27: Western Blot Analysis.

Figure 28:
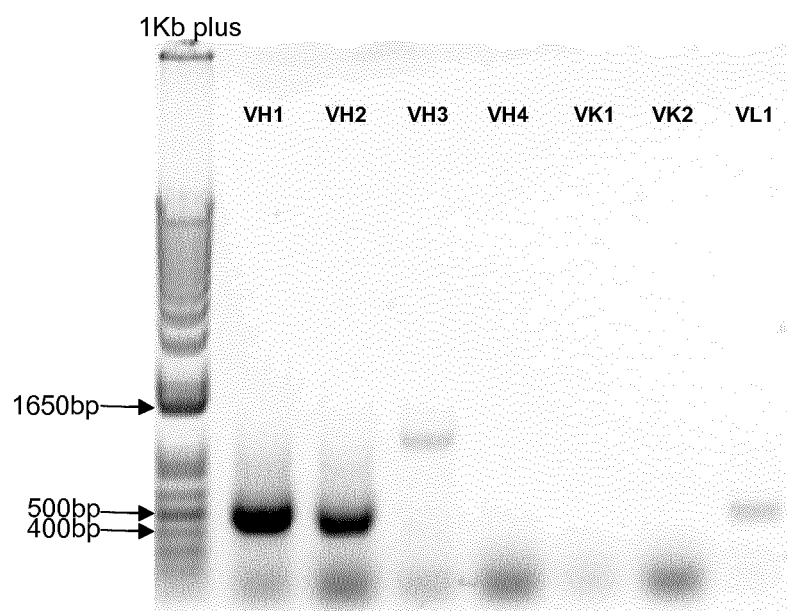

FIG. 28: PCR using several combinations of Ig variable domain primers.

Figure 29:
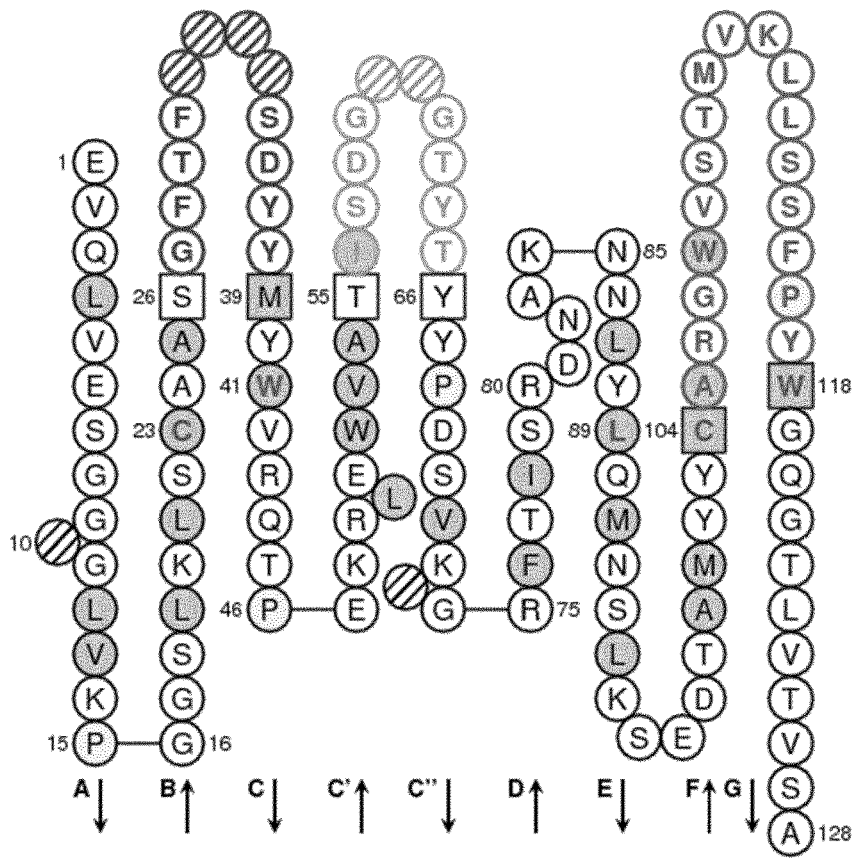

FIG. 29: Graphical representation of the CDR loops (Lefranc, M.-P. et al., Dev. Comp. Immunol., 27, 55-77 (2003) PMID: 12477501).

Figure 30:
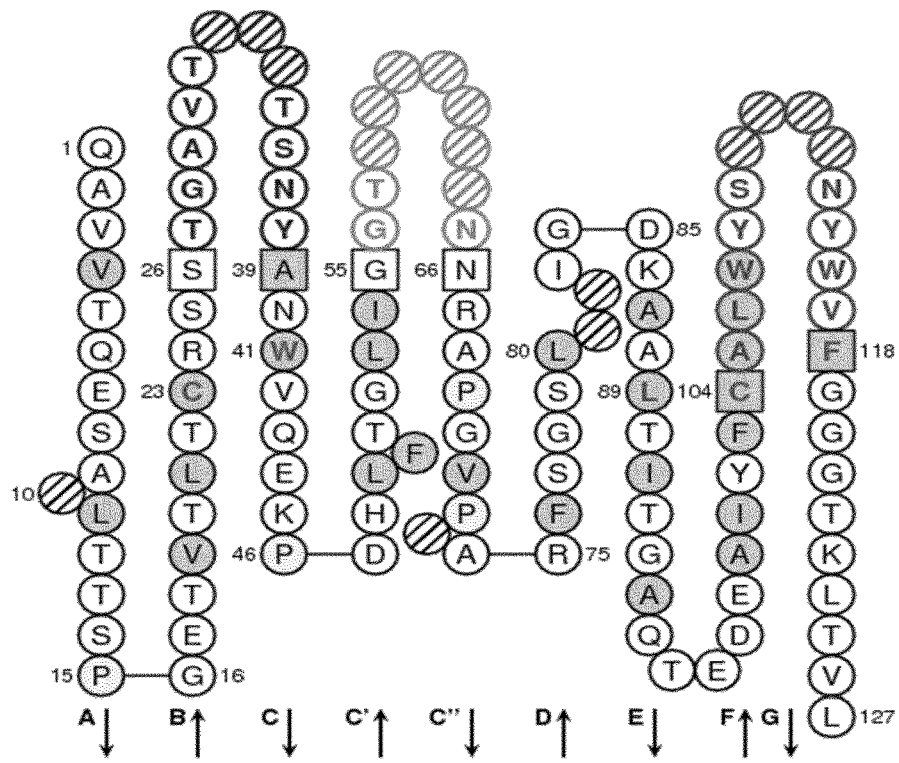

FIG. 30: Graphical representation of the CDR loops (Lefranc, M.-P. et al., Dev. Comp. Immunol., 27, 55-77 (2003) PMID: 12477501).

Figure 31:
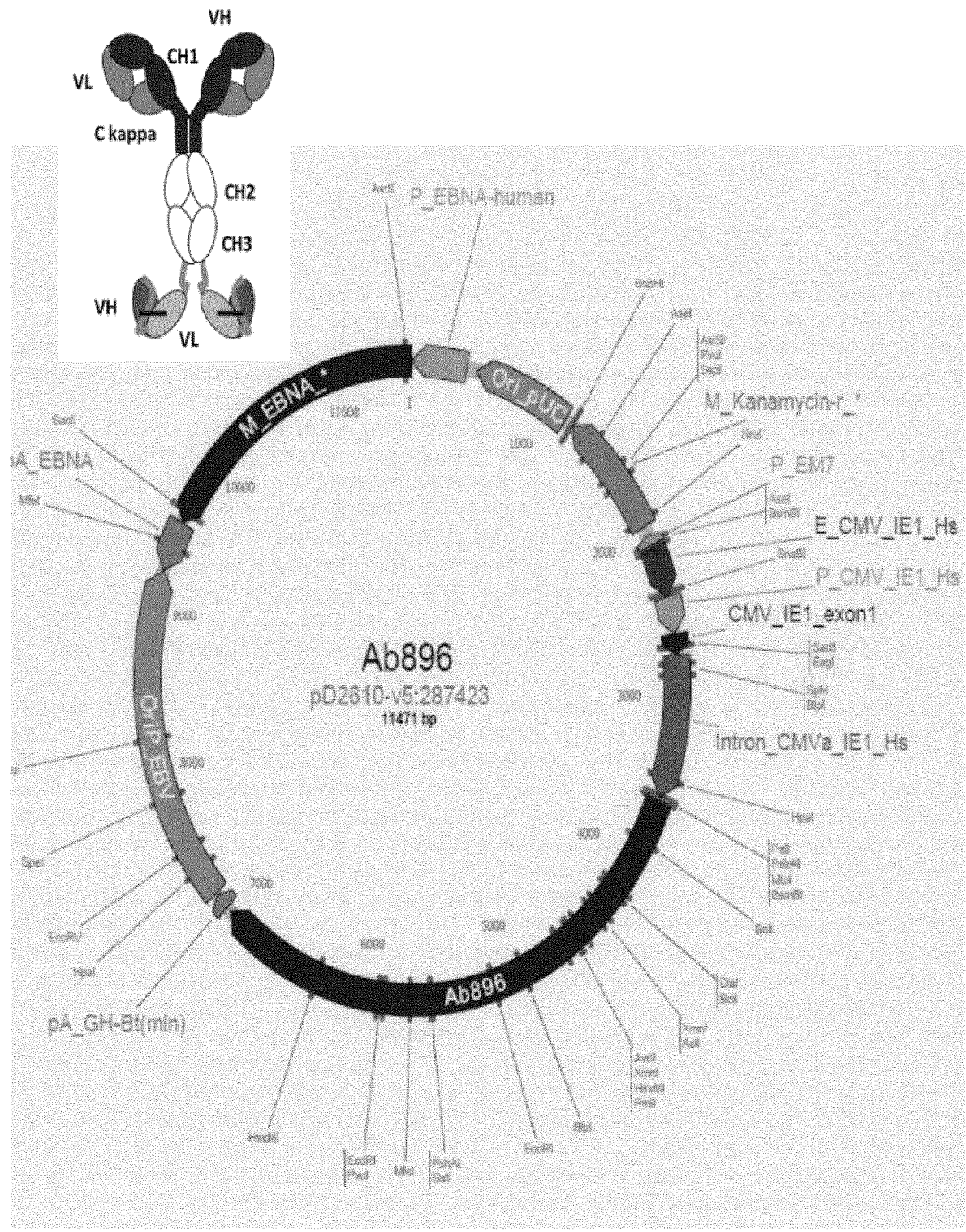

FIG. 31: Diagram illustrating the bispecific design and the plasmid map of InflaMab.

Figure 32:
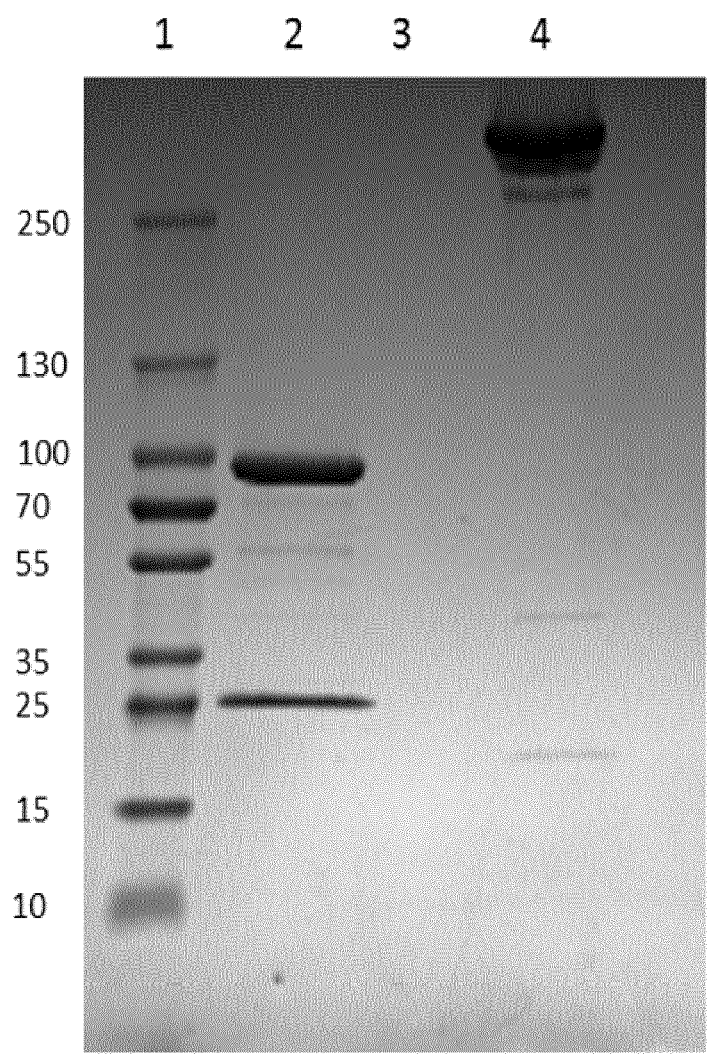

FIG. 32: 4-20% SDS-PAGE analysis of InflaMab. Molecular weight marker shown in kiloDaltons.

FIG. 33: Inflamab prevents IL-1β release. (Note, "Ulster Ab" is synonymous with "Inflamab" and "Bi-specific Ab".)

Figure 34:
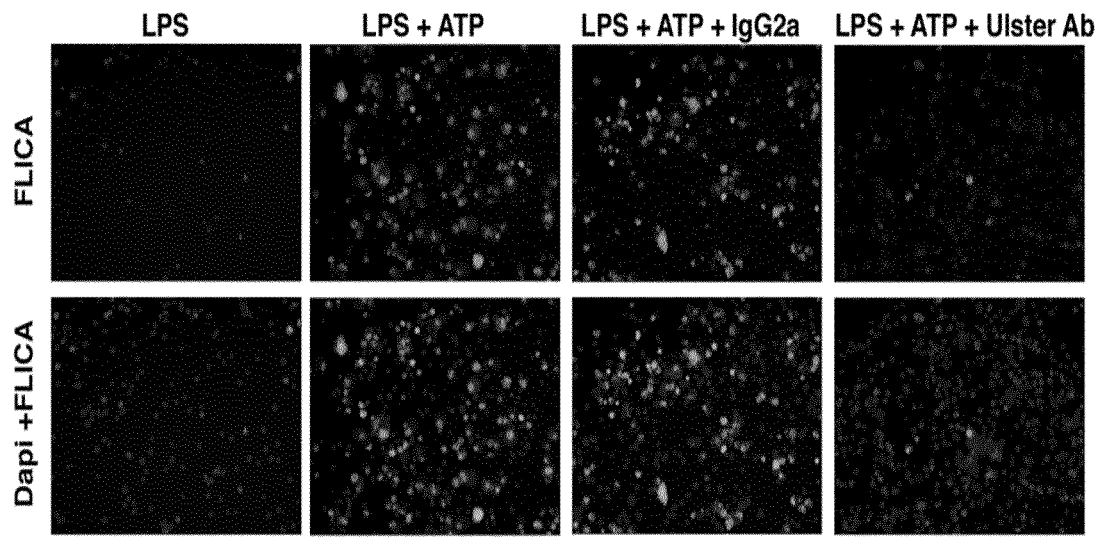

FIG. 34: Inflamab prevents caspase-1 activation in THP1 cells.

Figure 35:
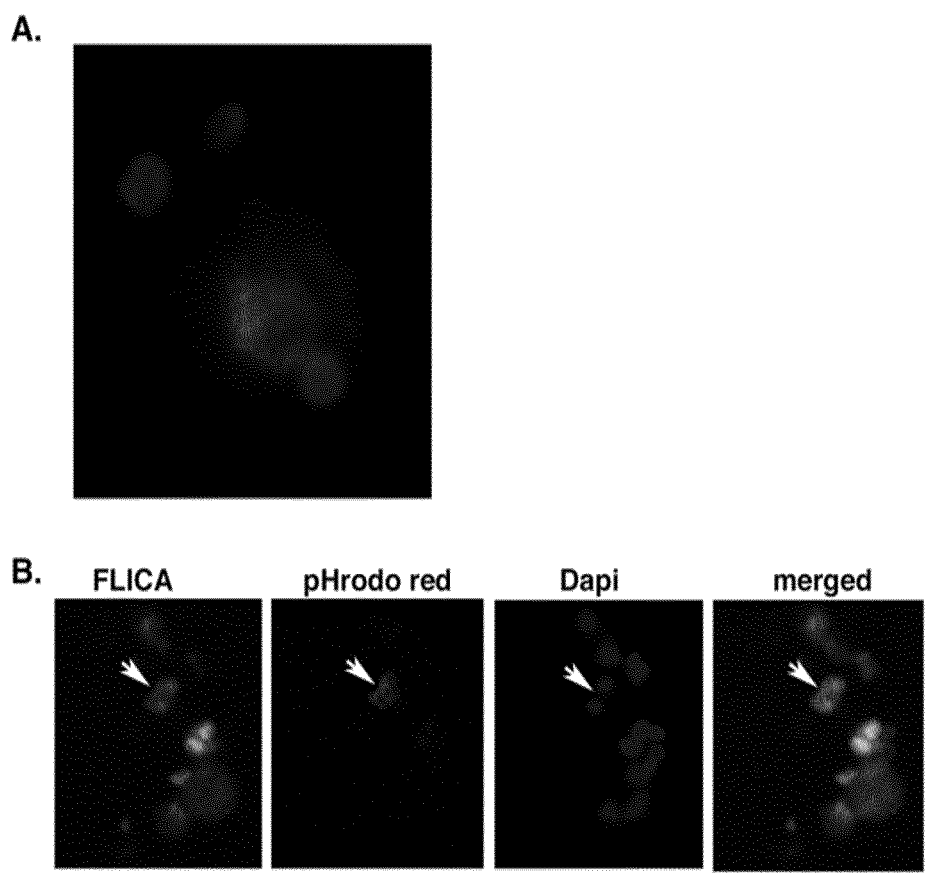

FIG. 35: Internalization of Inflamab.

Figure 36:
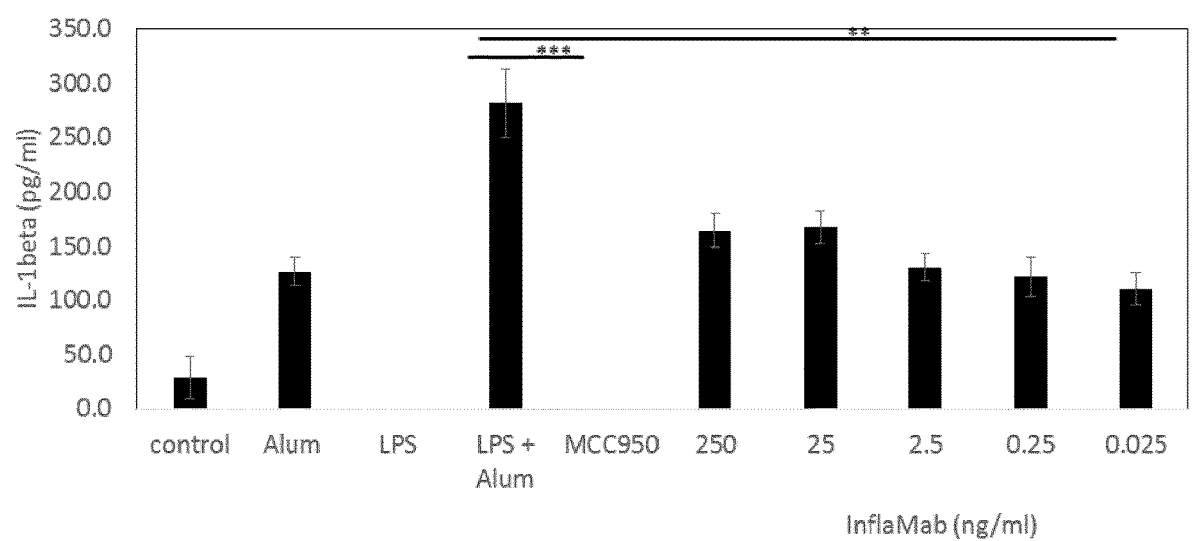

FIG. 36: InflaMab inhibits IL-1beta secretion from Bone Marrow Derived Macrophages (BMDMs).

Figure 37A:
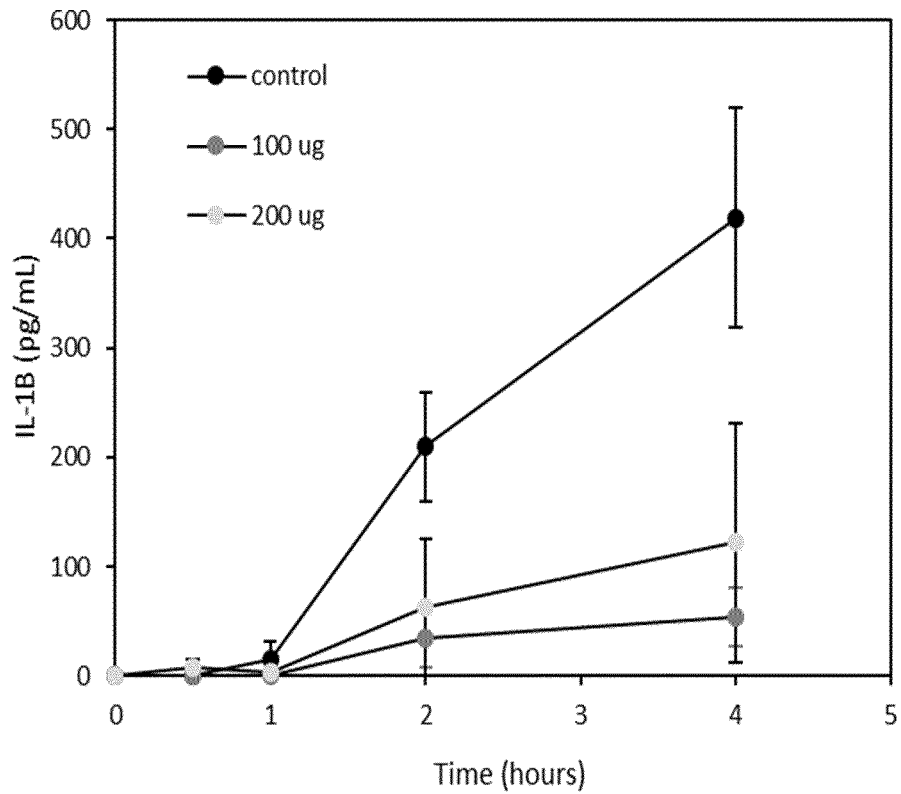
Figure 37B:
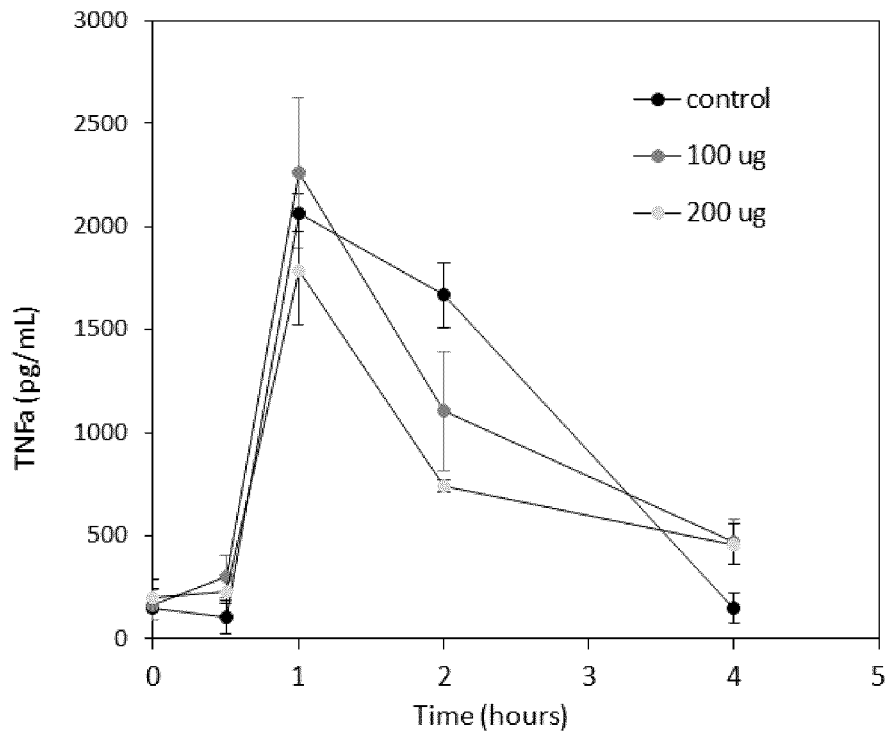

FIG. 37: IL-1beta, but not TNFalpha, is inhibited in vivo via LPS challenge.

Figure 38A:
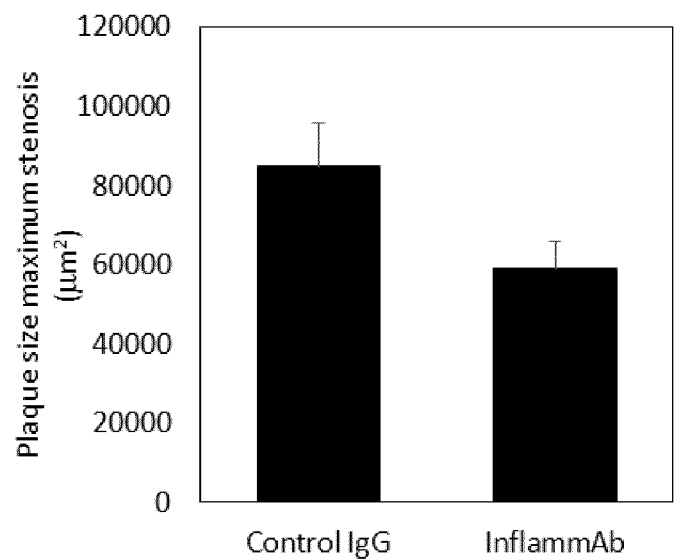
Figure 38B:
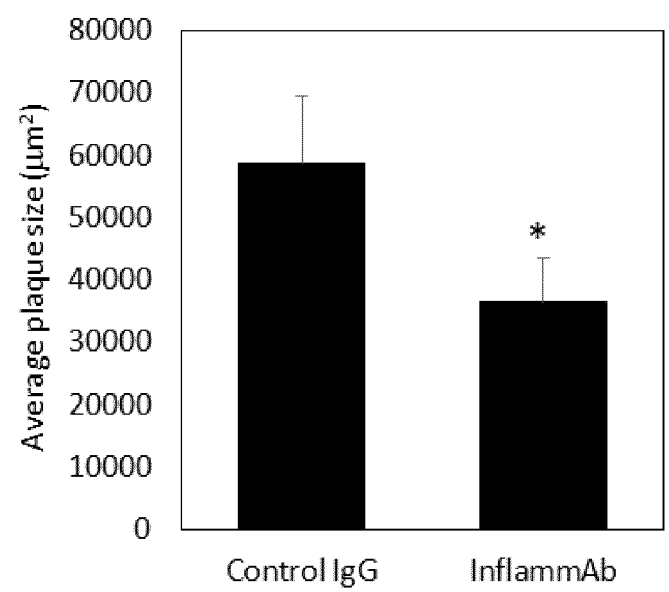

FIG. 38: InflaMab reduces plaque size in an in vivo apoE−/− model of atherosclerosis.

In a particular use or method of treatment, the modulator of the invention, e.g. the bi-specific antibody, acts according to steps which include:

1. Targeting the bispecific antibody to IL-1R1 to allow internalisation and entry of the antibody into the cell.
2. Targeting the antibody to NLRP3 in order to inhibit NLRP3 inflammasome assembly and subsequent IL-1β release from the cell, thus reducing inflammation.
3. Targeting the antibody to IL-1R1 triggers internalisation of the IL-1R1, thus making less IL-1R1 available for IL-1β binding resulting in further inhibiting the potentiation and amplification of inflammation.

Such a modulator of the first aspect of the invention provides a surprisingly additive inhibitory effect upon the inflammasome as a whole, not only the NLRP3 protein portion and thus will provide a more effective inhibitor of inflammasome-related diseases.

EXAMPLES

Transient Expression of IL-1R1 FC fusion (Example 1)
Generation of a monoclonal antibody against IL-1R1 (Example 2)
IL-1R1 monoclonal antibody sequencing report (Example 3)
NLRP3 peptide synthesis (Example 4)
Generation of a monoclonal antibody against NLRP3 (Example 5)
NLRP3 monoclonal sequencing report (Example 6)
InflaMab design (Example 7)
InflaMab transient expression (Example 8)
InflaMab for Atherosclerosis/Coronary Artery Disease (Example 9)

Example 1: Transient Expression of IL-1R1 Fc Fusion

IL-1R1 Fc is transiently expressed and purified in HEK293 cells. The purified protein is evaluated for size and purity by SDS PAGE and tested for endotoxin levels. Finally the protein is evaluated for activity by ELISA.

A mammalian expression vector encoding interleukin-1 receptor (IL-1R1) Fc fusion protein was transfected into HEK293 cells. The expressed Fc fusion protein was subsequently purified from cell culture supernatant using standard chromatography techniques. The concentration and purity were determined for the purified product.

Transient Transfection of HEK293 Cells and Purification of Protein

DNA coding for the amino acid sequence of IL-1R1 Fc (see Example 1A) was synthesised and cloned into a mammalian transient expression plasmid pD2610-v1 (DNA2.0). IL-1R1 Fc was expressed using a HEK293 cell based transient expression system and the resulting antibody containing cell culture supernatants was clarified by centrifugation and filtration. Two lots of IL-1R1 Fc were purified (using AKTA chromatography equipment) from cell culture supernatants via protein A affinity chromatography. Purified protein was dialysed/buffer exchanged into phosphate buffered saline solution. The purity of the recombinant protein was determined to be >95%, as judged by Sodium Dodecyl Sulphate Polyacrylamide gels (FIG. 1). Protein concentration was determined by measuring absorbance (1.0 mg/ml=A280 of 1.37). Details of the purified product are summarized in Table 1.

FIG. 1 shows 4-20% denaturing, reducing and non-reducing, SDS-PAGE analysis of IL-1R1 FC. Molecular weight marker shown in kiloDaltons. Lanes are as follows:

| Lane Number | Sample | Lot | Amount (µg) | Conditions |
| --- | --- | --- | --- | --- |
| 1 | See Blue plus 2 (Thermo Fisher) | — | — | Reducing |
| 2 | IL-1R1 FC | 1 | — | Reducing |
| 3 | Blank | — | — | NA |
| 4 | IL-1R1 FC | 2 | — | Reducing |

TABLE 1

| Purification summary: IL-1R1 Fc | | | | | |
| --- | --- | --- | --- | --- | --- |
| Sample | Lot | Concentration (mg/ml) | Volume (ml) | Total (mg) | Purity | Endotoxin (EU/mg) |
| IL-1R1Fc | 1 | 0.64 | 1.6 | 1.02 | >95% | ND |
| IL-1R1 Fc | 2 | 0.95 | 1.4 | 1.33 | >95% | ND |

Abbreviations are as follows;
ND, not determined.

Example 1A: IL-1R1 Fc Amino Acid Sequence (SEQ ID NO: 1)
MKVLLRLICFIALLISSLEADKCKEREEKIILVSSANEIDVRPCPLNPN

EHKGTITWYKDDSKTPVSTEQASRIHQHKEKLWFVPAKVEDSGHYYCVV

RNSSYCLRIKISAKFVENEPNLCYNAQAIFKQKLPVAGDGGLVCPYMEF

FKNENNELPKLQWYKDCKPLLLDNIHFSGVKDRLIVMNVAEKHRGNYTC

HASYTYLGKQYPITRVIEFITLEENKPTRPVIVSPANETMEVDLGSQIQ

LICNVTGQLSDIAYWKWNGSVIDEDDPVLGEDYYSVENPANKRRSTLIT

VLNISEIESRFYKHPFTCFAKNTHGIDAAYIQLIYPVTNFQKLEGGPSV

FIFPPPNIKDVLMISLTPKVTCVVVDVSEDDPDVQISWFVNNVEVHTAQT

QTHREDYNSTIRVVSHLPIQHQDWMSGKEFKCKVNNKDLPSPIERTISK

PKGLVRAPQVYTLPPPAEQLSRKDVSLTCLVVGFNPGDISVEWTSNGHT

EENYKDTAPVLDSDGSYFIYSKLNMKTSKWEKTDSFSCNVRHEGLKNYY

LKKTISRSPGK*

Example 2: Generation of a Monoclonal Antibody Against IL-1R1

The aim of this project is to generate a monoclonal antibody against IL-1R1. A population of 5 mice were immunised and screened for positive immune responses. After selecting a suitable candidate for fusion, splenocytes were fused with partner cells to produce a population of hybridomas. This population underwent a series of limiting dilutions and screening assays to produce fully monoclonal cell lines.

Cell Line Nomenclature

The product name "F237 5D1-1A8-2A5" refers to one of the 10 chosen monoclonal hybridoma cell lines. The name is comprised of components describing the production pathway at each stage. Each hybridoma selected from the post-fusion screening and each limiting dilution was given a number corresponding to the plate number and well location on that plate for which the hybridoma was chosen (i.e. 5D1-1A8-2A5). This nomenclature traces the derivation of each individual hybridoma allowing for clear differentiation in the screening process.

Abbreviations

| | |
|---|---|
| Ab | Antibody |
| DMSO | Dimethyl Sulfoxide |
| FCS | Fetal Calf Serum |
| ELISA | Enzyme-Linked Immunosorbent Assay |
| RT | Room Temperature |
| OD | Optical Density |
| PBST | Phosphate-buffered saline + 1% Tween 20 |
| PBS | Phosphate-buffered saline |
| RPM | Revolutions per minute |
| NP, LP, | Mouse Identification: No Punch, Left Punch, |
| RP, LRP, 2LP | Right Punch Left/Right Punch, 2 Left Punches |
| HAT | Hypoxanthine, Aminopterin, Thymidine supplement |
| HATR Media[1] | DMEM supplemented with 2% Roche (HFCS), 2% HAT, 1% Pen/Strep, 1% L-Glutamine |
| SFM | Serum Free Medium |
| PEG | Polyethylene Glycol |
| GAM-HRP | Goat Anti-Mouse-Horse Radish Peroxidase |
| HT | Hypoxanthine and Thymidine |
| LD1 | First Limiting Dilution |
| LD2 | Second Limiting Dilution |

[1]This is the media that was used for all cultures following fusion and screening.

Materials

Reagents and Media

| Reagent | Supplier | Catalogue No. |
|---|---|---|
| L-glutamine | Gibco | 25030-024 |
| HAT Supplement | Gibco | 21060-017 |
| HFCS | Roche | 11363735001 |
| DMEM Glutamax | Gibco | 61965-059 |
| Penicillin/Streptomycin | Gibco | 15140-122 |
| FCS | Gibco | 16000.044 |
| DMSO | Sigma | D2650 |
| Trypan Blue | Sigma | T8154 |
| PEG | Sigma | 10783641001 |
| Freund's Adjuvant Complete | Sigma | F5881 |
| Freund's Adjuvant Incomplete | Sigma | F5506 |
| Sodium Hydrogen Carbonate | VWR | 27778.260 |
| Sodium Carbonate | Sigma | S2127-500G |
| Powdered Milk | Marvel | Original Dried Skimmed |
| Tween 20 (10%) | Sigma | P1379-1L |
| GAM-HRP (Fc Specific) | Sigma | A2554 |
| TMB | Biopanda | TMB-S-002 |
| Mr. Frosty | Nalgene | 55710-200 |

| Name | Supplier | Catalogue No. |
|---|---|---|
| 25 cm² static flasks | Corning | 430639 |
| 75 cm² static flasks | Corning | 430641 |
| 96-well plate sterile | Corning | 3595 |
| 96-well plate sterile TPP | Primer Scientific | 92696T |
| Cryovials | Fisher Scientific | 366656 |
| Maxi Sorb 96-well plates | Nunc | 442404 |

Equipment $CO_2$ Cell culture static incubators (SANYO)
Plate reader Sunrise (Tecan)
Centurion Scientific K40R Centrifuge
Grant-Bio Multishaker PSU 20

Methods

Antigen Preparation

Once the immunogen (IL-1R1) was purified, these solutions were diluted to 200 μg/ml in sterile, EF-PBS and aliquoted in volumes of 600 μl for immunisation and 150 μl for boosts and ELISA screening. These aliquots were labelled and stored at −20° C.

Immunisations

A population of 5 BalbC mice were immunised subcutaneously with 200 μl of a 1:1 emulsion of Freund's Adjuvant Complete (Sigma) and a 600 μl aliquot of IL-1R1 prepared herein. Two weeks after the 1$^{st}$ immunisation, the population was immunized with a 2$^{nd}$ injection at the same volumes and concentrations as the original injection only using Freund's Adjuvant Incomplete (Sigma) instead. One week after the 2$^{nd}$ immunisation, the mice were tagged by ear punches (NP, RP, LP, LRP, 2LP), and test bleeds were screened as described herein for preliminary results. Three weeks after the 2$^{nd}$ immunisation, the population was immunised a 3$^{rd}$ time using the same method as the 2$^{nd}$ injection. One week after the 3$^{rd}$ immunisation, test bleeds were screened, and the mouse with an ear tag of RP was then selected for fusion.

Test Bleed ELISAs

Tail bleeds were taken from the population of 5 BalbC mice and centrifuged at 8000 rpm for 10 min at RT (room temperature). The blood serum from each mouse was collected, loaded onto the plate the same day as screening, and stored at −20° C. This screening was performed twice for the selection of a suitable mouse for fusion.

The day prior to screening, a Maxi Sorp plate was coated by adding 100 μl/well of 50 mM sodium carbonate coating buffer (pH 9.5) containing the IL-1R1 at 1 μg/ml. A separate coating solution was prepared by diluting APO-A1 in the same coating buffer at 1 μg/ml. These solutions were loaded onto the plate in alternating rows so as to provide two wells to load each sample that demonstrates a positive and negative result. This plate was incubated overnight at 4° C. in static conditions.

The following morning, coating buffer was removed, and 200 μl/well of blocking solution (4.0% w/v semi skim milk powder, 1×PBS) was added and agitated at 150 rpm for 2 hr at RT. The plate was washed three times with PBS-T (0.1% v/v Tween 20). PBS was loaded into each well at 100 μl/well, and 1 μl of each test bleed serum was loaded into each positive and negative well. The plate was incubated at 150 rpm (Grant Shaker) for 2 hrs at room temperature. These samples were then removed and washed four times with PBS-T. 100 μl/wel,l GAM-HRP diluted 1:5000 (Sigma, UK) was added, and the plate was incubated for 1 hr with agitation at 150 rpm at RT. The secondary antibody was removed, and the plate was washed four times with PBS-T and once in PBS. 100 μl/well of TMB substrate solution was added and incubated at 37° C. for 10 minutes. 50 μl 1M HCl was added per well and the plate immediately read at 450 nm on a Tecan Sunrise plate reader.

After the second test bleed ELISA screening, the mouse with an ear tag of RP was selected for fusion by expressing the most positive immune response.

Boost Injections

One week after the 3$^{rd}$ and final immunization, a boost injection was given to BalbC mouse RP by injecting 100 μl of aliquoted IL-1R1 at 200 μg/ml without any adjuvant.

Fusion F237

One week before fusion, SP2 cells were broken out from liquid nitrogen and were passaged in 10% FCS DMEM supplemented with 1% Pen/Strep, 1% L-glutamine until 3×12 ml T75 flasks were 75%-90% confluent on the day of fusion. On the day of the fusion, SP2 cells were dislodged by tapping the flask and were centrifuged at 1000 rpm for 5 min at 37° C. The cells were resuspended in 20 ml SFM DMEM, centrifuged again, and resuspended in 10 ml SFM DMEM. SP2 cells were stored in a Sterilin tube in SFM at 37° C., 6% $CO_2$ until needed.

After euthanasia, the spleen was aseptically removed from the mouse that showed the strongest immune response. Splenocytes were extracted by puncturing both ends of the spleen with a fine gauge needle and flushing 10-15 ml SFM DMEM. Splenocytes were transferred to a sterilin tube and washed twice with 20 ml serum free DMEM by centrifugation at 1300 rpm for 5 min at 37° C. and gently removing the supernatant. The splenocytes were resuspended in 10 ml Serum free DMEM in a sterilin tube.

Using the SP2 cells stored at 37° C., the SP2 cells were added to the splenocytes. This SP2/splenocytes culture was centrifuged at 1300 rpm for 5 min at 37° C. After discarding the supernatant, 1 ml PEG was added to the SP2/splenocytes culture dropwise while stirring continuously over a period of 3 min. 1 ml SFM DMEM was added to the fusion mixture and stirred for 4 min. 10 ml SFM DMEM was added dropwise to the fresh culture and incubated for in 37° C. water bath for 5 min. The cells were then centrifuged at 1000 rpm for 5 min at 37° C. The pellet was resuspended in 200 mL HATR media and was plated at 200 μl/well in 10×96 well culture plates which were incubated 11 days at 37° C. in 6% $CO_2$ prior to screening.

Post-Fusion Screening and Post-LD Screening

Eleven days after fusion, protoclones were screened by ELISA. 20× Maxi Sorp 96 well plates were coated as described herein using APO-A1 at 1 μg/ml as the negative control for specificity. The coating solution was removed and the plates were blocked as described herein. Samples were prepared by removing 160 μl of supernatant from each well of the ten fusion plates, limiting dilution plates, or 24-well plates and transferring to fresh 96 well culture plates containing 50 μl 1×PBS. After 2 hours of blocking, the blocking solution was removed, and the plates were washed 3× with PBS-T. The samples from each dilution plate were loaded onto the ELISA plates at 100 μl/well by adding 1 row from each dilution plate per 2 rows on the ELISA plates to account for specificity of the coating antigens. Two wells per ELISA were incubated with 100 μl 1×PBS as a negative control. These samples were incubated at 150 rpm for 2 hours at room temperature.

Limiting Dilutions Once the hybridoma populations were expanded in 24-well plates and growing well, a secondary screen was performed to select the most specific and highest producing populations for rounds of limiting dilutions.

Both limiting dilutions were performed for 1-3 protoclones each by seeding 2-4×96-well plates at 1 cell/well in 200 μl culture/well. The plates were prepared by counting each culture in the 24-well plate and were diluted 10× as an intermediate dilution, then were diluted to 200 cells in 40 ml. The culture was plated at 200 μl/well and left to incubate at 37° C., 6% $CO_2$ for 7-10 days until the wells were 80%-90% confluent. Each well for both limiting dilutions were screened by ELISA as described herein.

Final Clone Selection

Following the second limiting dilution, 10 clones were selected for expansion in a 24 well plate. Each clone was left to grow in 37° C., 6% $CO_2$ for 6 days until each well became 80%-90% confluent. When the clones were well established in the 24-well plates, each clone at 1 ml/well was transferred to a T25 flask containing 5 ml fresh 10% HATR DMEM for cryopreservation.

Cryopreservation of Monoclonal Cell Lines

Once the clones were well established (80%-90% confluency) in T25 flasks, each 5 ml culture was centrifuged at 1000 rpm for 5 min at 37° C. and was resuspended in 1 ml of fresh 10% DMEM HATR media. Each 1 ml culture was transferred to a cryovial containing 300 μl of a 1:1 ratio of FCS to DMSO. The vials were sealed and placed in a Mr. Frosty and transferred to the −70° C. freezer for short-term storage.

Cell Preparation for Sequencing

Anti-IL-1R1 produced from clone F237 5D1-1A8-2A5 was selected for sequencing. Once the culture was confluent in the T25 flask, the supernatant was discarded. The cells were dislodged by cell scraping into 2 ml fresh media and were centrifuged at 7,600 rpm for 5 min at RT. The supernatant was then discarded and the pellet was flash frozen in liquid nitrogen and placed in −70° C. until ready for mRNA extraction.

Immunisation and Screening of Test Bleeds

A colony of mice were immunised with an IL-1R1 immunogen (produced in house in CHO cells) and regular test bleeds were taken over an 11 week period. Test bleeds were screened for IL-1R1 mAb expression levels using ELISA and internalisation capability using the pHrodo fluorescent assay (Thermo Fisher Scientific, UK https://www-.thermofisher.com/order/catalog/product/P35369 and https://www.sigmaaldrich.com/catalog/product/sigma/ m4280?lang=en&region=GB).

Results

Test Bleed 1

One week after the 2$^{nd}$ immunisation, a tail bleed was taken from each of the 5 mice and screened against IL-1β and APO-A1 for determination of a suitable animal for fusion and a relative specificity of the polyclonal antibody produced—see FIG. 2.

Test Bleed 2

After screening sera from tail bleeds, the mouse with an ear tag of RP was selected for the fusion of its splenocytes to fusion partner SP2 culture as it demonstrated the best immune response—see FIG. 3.

Post-Fusion Screening

Once the wells in each plate had reached 70%-80% confluency, the plates were screened by ELISA against IL-1R1 and APO-A1. The hybridoma population producing the highest responses were selected for expansion in a 24-well plate—see FIG. 4.

1$^{st}$ 24-Well Plate Screening

Clones were selected from the post-fusion screening and were arrayed into a 24 well plate for expansion followed by a secondary screening that determines suitable protoclones for the first round of limiting dilutions—see FIG. 5.

Limiting Dilution 1 Screening

Once the 1st limiting dilution plates were confluent, the limiting dilution was screened by ELISA against IL-1R1 and APO-A1. Eleven hybridoma populations were selected from F237 2H12, F237 5D1, and F237 7E6 that demonstrated the highest and most specific response—see FIG. 6.

2$^{nd}$ 24-Well Plate Screening

When the clones became confluent in the 24-well plate, each clone was screened by ELISA against IL-1R1 and APO-A1. F237-5D1-1A8 was selected for the 2$^{nd}$ round of limiting dilution over 4×96 well plates—see FIG. 7.

Limiting Dilution 2 Screening

Once the wells in each plate had reached 70%-80% confluency, the plates were screened by ELISA against IL-1R1 and APO-A1. The hybridoma population producing the highest response and highest specificity were selected for expansion in a 24-well plate and cryopreservation—see FIG. 8.

IL-1R1 Internalisation in THP1 Cells was Immunofluorescence Imaged

Fluorescence microscopic images taken from THP1 macrophages treated with LPS and ATP to induce the expression of the IL-1R1—see FIG. 10. The cells were incubated with mouse serum from several different mice, containing the test antibody against the IL-1R1, which was conjugated to a pHrodo™ dye (that will only fluoresce within a cell). Strong IL-1R1 immunoreactivity was observed in the nucleus and cytoplasm of the THP1 cells. IL-1R1 and DAPI staining at ×40 magnification. No staining was observed in the secondary antibody only treated control cells. Images are from four different wells used in two different experiments. The best mouse was selected to take forward to the fusion hybridoma and cloning stages.

THP1 macrophages (see FIG. 11) treated with LPS and ATP to induce the expression of the IL-1R1. The cells were incubated with mouse serum from several mice containing the test monoclonal antibody against the IL-1R1, which was conjugated to a pHrodo dye (that will only fluoresce within a cell) and analysed with flow cytometry. More fluorescence was seen in the IL-1R1 antibody treated cells (i) as compared to the control secondary antibody only treated cells (ii). Using this data and that from FIG. 3, the best mouse was chosen to take forward to the fusion hybridoma and cloning stages.

Conclusions

The aim of the project was to produce a range of antibodies against IL-1R1. Once the mice were immunised and screened, RP was selected for fusion. 10 monoclonal hybridoma cell lines were produced from two rounds of limiting dilutions. Each population was selected by highest production and highest specificity for IL-1R1. These final cell lines have been frozen down, and the antibody expressed by this cell line will be sequenced.

Example 3: IL-1R1 Monoclonal Antibody Sequencing mRNA was extracted from the hybridoma cell pellets. Total RNA was extracted from the pellets using a conventional RNA extraction protocol. Cell pellets were homogenised using RNA STAT-60 reagent. Upon addition of chloroform, the homogenate separated into an aqueous phase and an organic phase, and total RNA was isolated in the aqueous phase. Isopropanol was used to precipitate the RNA, followed by ethanol washes and solubilisation in water.

RT-PCR cDNA was created from the RNA by reverse-transcription with an oligo(dT) primer. PCR reactions are set up using variable domain primers to amplify both the VH and VL regions of the monoclonal antibody DNA giving the following bands—see FIG. 12.

The VH and VL products were cloned into the Invitrogen sequencing vector pCR2.1 and transformed into TOP10 cells and screened by PCR for positive transformants. Selected colonies were picked and analyzed by DNA sequencing on an AB13130xl Genetic Analyzer, the result may be seen below.

Sequencing Results

Heavy Chain

V$_H$ Amino Acid Sequence Alignment:

```
                         1                                                  50
VH1.1        (1)  MEWSCVMLFLMAAAQSIQAQIQLVQSGPELRKPGETVRISCKASGYPFTT
VH1.4        (1)  MECSCVMLFLMAAAQSIQAQIQLVQSGPELRKPGETVRISRKASGYPFTT
VH1.3        (1)  MGWSWVMLFLMAAAQSIQAQIQLVQSGPELRKPGETVRISCKASGYPFTT
VH2.1        (1)  MGWVWNLLFLMAAAQSIQAQIQLVQSGPELRKPGETVRISCKASGYPFTT
VH2.5        (1)  MGWVWTLPFLMAAAQSIQAQIQLVQSGPELRKPGETVRISCKASGYPFTT
VH2.3        (1)  MGWVWNLPFLMAAAQSIQAQIQLVQSGPELRKPGETVRISCKASGYPFTT
VH1.2        (1)  MDWVWTLPFLMAAAQSIQAQIQLVQSGPELRKPGETVRISCKASGYPFTT
VH2.4        (1)  MDWLWNLPFLMAAAQSIQAQIQLVQSGPELRKPGETVRISCKASGYPFTT
Consensus    (1)  MGWVWNLPFLMAAAQSIQAQIQLVQSGPELRKPGETVRISCKASGYPFTT 51                                                100
VH1.1       (51)  AGLQWVQKMSGKGLKWIGWMNTQSEVPKYAEEFKGRIAFSLETAASTAYL
VH1.4       (51)  AGLQWVQKMSGKGLKWIGWMNTQSEVPKYAEEFKGRIAFSLETAASTAYL
VH1.3       (51)  AGLQWVQKMSGKGLKWIGWMNTQSEVPKYAEEFKGRIAFSLETAASTAYL
VH2.1       (51)  AGLQWVQKMSGKGLKWIGWMNTQSEVPKYAEEFKGRIAFSLETAASTAYL
VH2.5       (51)  AGLQWVQKMSGKGLKWIGWMNTQSEVPKYAEEFKGRIAFSLETAASTAYL
VH2.3       (51)  AGLQWVQKMSGKGLKWIGWMNTQSEVPKYAEEFKGRIAFSLETAASTAYL
```

-continued

```
VH1.2      (51)  AGLQWVQKMSGKGLKWIGWMNTQSEVPKYAEEFKGRIAFSLETAASTAYL
VH2.4      (51)  AGLQWVQKMSGKGLKWIGWMNTQSEVPKYAEEFKGRIAFSLETAASTAYL
Consensus  (51)  AGLQWVQKMSGKGLKWIGWMNTQSEVPKYAEEFKGRIAFSLETAASTAYL 101                                              150
VH1.1      (101) QINNLKTEDTATYFCAKSVYFWWRYFDVWGAGTTVTVSSAKTTPPPVYPL
VH1.4      (101) QINNLKTEDTATYFCAKSVYFWWRYFDVWGAGTTVTVSSAKTTPPSVFPL
VH1.3      (101) QINNLKTEDTATYFCAKSVYFWWRYFDVWGAGTTVTVSSAKTTPPPVYPL
VH2.1      (101) QINNLKTEDTATYFCAKSVYFWWRYFDVWGAGTTVTVSSAKTTPPPVYPL
VH2.5      (101) QINNLKTEDTATYFCAKSVYFWWRYFDVWGAGTTVTVSSAKTTPPPVYPL
VH2.3      (101) QINNLKTEDTATYFCAKSVYFWWRYFDVWGAGTTVTVSSAKTTPPPVYPL
VH1.2      (101) QINNLKTEDTATYFCAKSVYFWWRYFDVWGAGTTVTVSSAKTTPPSVYPL
VH2.4      (101) QINNLKTEDTATYFCAKSVYFWWRYFDVWGAGTTVTVSSAKTTPPPVYPL
Consensus  (101) QINNLKTEDTATYFCAKSVYFWWRYFDVWGAGTTVTVSSAKTTPPPVYPL 151
VH1.1      (151) A
VH1.4      (151) A
VH1.3      (151) A
VH2.1      (151) V
VH2.5      (151) V
VH2.3      (151) A
VH1.2      (151) A
VH2.4      (151) A
Consensus  (151) A VH1.1      (SEQ ID NO: 2)
VH1.4      (SEQ ID NO: 3)
VH1.3      (SEQ ID NO: 4)
VH2.1      (SEQ ID NO: 5)
VH2.5      (SEQ ID NO: 6)
VH2.3      (SEQ ID NO: 7)
VH1.2      (SEQ ID NO: 8)
VH2.4      (SEQ ID NO: 9)
Consensus  (SEQ ID NO: 7)
```

Key to amino acid shading:
Black      non-similar residues
Bold       consensus residue derived from a block of residues at a given position
Underlined residues similar in structure to consensus residue or each other when no consensus found
Italicised consensus residue derived from a completely conserved residue at a given position
Underlined/ residue weakly similar to consensus residue at given
italicized position $V_H$ Consensus Amino Acid Sequence:

(SEQ ID NO: 7)

MGWVWNLPFLMAAAQSIQAQIQLVQSGPELRKPGETVRISCKASGYPFTT

AGLQINVQKMSGKGLKWIGWMNTQSEVPKYAEEFKGRIAFSLETAASTAY

LQINNLKTEDTATYFCAKSVYFNWRYFDVWGAGTTVTVSSAKTTPPPVYP

LA

The variable domain is highlighted in BOLD.

The Complementarity Determining Regions (CDRs) are underlined as determined by the IMGT numbering system (Lefranc, M.-P. et al., Nucleic Acids Research, 27, 209-212 (1999))—see FIG. 13.

Key to amino acid shading, in FIG. 13:

Blue shaded circles are hydrophobic (non-polar) residues in frameworks 1-3 at sites that are hydrophobic in the majority of antibodies.

Yellow shaded circles are proline residues.

Squares are key residues at the start and end of the CDR.

Red amino acids in the framework are structurally conserved amino acids.

Light Chain $V_L$ Amino Acid Sequence Alignment:

```
                 1                                                50
VK1.1      (1)   MRAPAQFLGLLLLWTSASRCDIVMTQSPATLSVTPGDRVSLSCRASQSIS
VK1.5      (1)   MRAPAQLLGLLLFWTSASRCDIVMTQSPATLSVTPGDRVSLSCRASQSIS
VK1.3      (1)   MRSPAQFLGLLLFWTSASRCDIVMTQSPATLSVTPGDRVSLSCRASQSIS
VK1.4      (1)   MRSPAQFLGLLLFWTSASRCDIVMTQSPATLSVTPGDRVSLSCRASQSIS
VK2.1      (1)   MVSSAQFLGLLLFWTSASRCDIVMTQSPATLSVTPGDRVSLSCRASQSIS
VK2.6      (1)   MVSTAQFLGLLLFWTSASRCDIVMTQSPATLSVTPGDRVSLSCRASQSIS
Consensus  (1)   MRSPAQFLGLLLFWTSASRCDIVMTQSPATLSVTPGDRVSLSCRASQSIS 51                                               100
VK1.1      (51)  DYLSWYQQRSHESPRLIIKYASQSISGIPSRFSGSGSGSDFTLSINSVEP
VK1.5      (51)  DYLSWYQQRSHESPRLIIKYASQSISGIPSRFSGSGSGSDFTLNINSVEP
VK1.3      (51)  DYLSWYQQRSHESPRLIIKYASQSISGIPSRFSGSGSGSDFTLSINSVEP
```

-continued

```
VK1.4      (51)  DYLSWYQQRSHESPRLIIKYASQSISGIPSRFSGSGSGSDFTLSINSVEP
VK2.1      (51)  DYLSWYQQRSHESPRLIIKYASQSISGIPSRFSGSGSGSDFTLSINSVEP
VK2.6      (51)  DYLSWYQQRSHESPRLIIKYASQSISGIPSRFSGSGSGSDFTLSINSVEP
Consensus  (51)  DYLSWYQQRSHESPRLIIKYASQSISGIPSRFSGSGSGSDFTLSINSVEP 101                                              150
VK1.1      (101) EDVGVYYCQHGHSFPLTFGSGTKLELKRADAAPTVSIFPPSSEQLTSGGA
VK1.5      (101) EDVGVYYCQHGHSFPLTFGSGTKLELKRADAAPTVSIFPPSSEQLTSGGA
VK1.3      (101) EDVGVYYCQHGHSFPLTFGSGTKLELKRADAAPTVSIFPPSSEQLTSGGA
VK1.4      (101) EDVGVYYCQHGHSFPLTFGSGTKLELKRADAAPTVSIFPPSSEQLTSGGA
VK2.1      (101) EDVGVYYCQHGHSFPLTFGSGTKLELKRADAAPTVSIFPPSSEQLTSGGA
VK2.6      (101) EDVGVYYCQHGHSFPLTFGSGTKLELKRADAAPTVSIFPPSSEQLTSGGA
Consensus  (101) EDVGVYYCQHGHSFPLTFGSGTKLELKRADAAPTVSIFPPSSEQLTSGGA 151       162
VK1.1      (151) SVVCFLNNFYFK
VK1.5      (151) SVVCFLNNFYFK
VK1.3      (151) SVVCFLNNFYFK
VK1.4      (151) SVVCFLNNFYFR
VK2.1      (151) SVVCFLNNFYFK
VK2.4      (151) SVVCFLNNFYFR
Consensus  (151) SVVCFLNNFYFK VK1.1      (SEQ ID NO: 10)
VK1.5      (SEQ ID NO: 11)
VK1.3      (SEQ ID NO: 12)
VK1.4      (SEQ ID NO: 13)
VK2.1      (SEQ ID NO: 14)
VK2.6      (SEQ ID NO: 15)
Consensus  (SEQ ID NO: 12)
```

Key to amino acid shading:
Black      non-similar residues
Bold       consensus residue derived from a block of residues at a given position
Underlined residues similar in structure to consensus residue or each other when no consensus found
Italicised consensus residue derived from a completely conserved residue at a given position
Underlined/ residue weakly similar to consensus residue at given
italicized  position $V_L$ Consensus Amino Acid Sequence:

(SEQ ID NO: 12)

MRSPAQFLGLLLFWTSASRCDIVMTQSPATLSVTPGDRVSLSCRASQSIS

DYLSWYQQRSHESPRLIIKYASQSISGIPSRFSGSGSGSDFTLSINSVEP

EDVGVYYCQHGHSFPLTFGSGTKLELKRADAAPTVSIFPPSSEQLTSGGA

SVVCFLNNFYPK

The variable domain is highlighted in BOLD.

The Complementarity Determining Regions (CDRs) are underlined as determined by the IMGT numbering system (Lefranc, M.-P. et al., Nucleic Acids Research, 27, 209-212 (1999))—see FIG. 14.

Key to amino acid shading, in FIG. 14:

Blue shaded circles are hydrophobic (non-polar) residues in frameworks 1-3 at sites that are hydrophobic in the majority of antibodies.

Yellow shaded circles are proline residues.

Squares are key residues at the start and end of the CDR.

Red amino acids in the framework are structurally conserved amino acids.

VH Sequencing results:

VH1.1 DNA Sequence:

(SEQ ID NO: 16)

ATGGAATGGAGCTGTGTCATGCTCTTTCTCATGGCAGCAGCTCAAAGTATCCAAGCACAGATCC

AGTTGGTGCAGTCTGGACCTGAGCTGAGGAAGCCTGGAGAGACAGTCAGGATCTCCTGCAAGG

CCTCTGGGTATCCCTTCACAACTGCTGGATTGCAGTGGGTACAGAAGATGTCAGGAAAGGGTTT

GAAATGGATTGGCTGGATGAACACCCAGTCTGAAGTGCCAAAATATGCAGAAGAGTTCAAGGGA

CGGATTGCCTTCTCTTTGGAAACCGCTGCCAGTACTGCATATTTACAGATAAACAACCTCAAAAC

TGAGGACACGGCAACGTATTTCTGTGCGAAATCGGTCTATTTTAACTGGAGATATTTCGATGTCT

GGGGTGCAGGGACCACGGTCACCGTCTCCTCAGCCAAAACGACACCCCCACCCGTTTATCCAC

TGGCC

VH1.1 Amino Acid Sequence:

(SEQ ID NO: 2)

MEWSCVMLFLMAAAQSIQAQIQLVQSGPELRKPGETVRISCKASGYPFTTAGLQWVQKMSGKGLK

WIGWMNTQSEVPKYAEEFKGRIAFSLETAASTAYLQINNLKTEDTATYFCAKSVYFNWRYFDVWGA

GTTVTVSSAKTTPPPVYPLA

VH1.3 DNA Sequence:

(SEQ ID NO: 17)

ATGGGATGGAGCTGGGTCATGCTCTTTCTCATGGCAGCAGCTCAAAGTATCCAAGCACAGATCC

AGTTGGTGCAGTCTGGACCTGAGCTGAGGAAGCCTGGAGAGACAGTCAGGATCTCCTGCAAGG

CTTCTGGGTATCCCTTCACAACTGCTGGACTGCAGTGGGTACAGAAGATGTCAGGAAAGGGTTT

GAAATGGATTGGCTGGATGAACACCCAGTCTGAAGTGCCAAAATATGCAGAAGAGTTCAAGGGA

CGGATTGCCTTCTCTTTGGAAACCGCTGCCAGTACTGCATATTTACAGATAAACAACCTCAAAAC

TGAGGACACGGCAACGTATTTCTGTGCGAAATCGGTCTATTTTAACTGGAGATATTTCGATGTCT

GGGGTGCAGGGACCACGGTCACCGTCTCCTCAGCCAAAACGACACCCCCACCCGTTTATCCCT

TGGCC

VH1.3 Amino Acid Sequence:

(SEQ ID NO: 4)

MGWSWVMLFLMAAAQSIQAQIQLVQSGPELRKPGETVRISCKASGYPFTTAGLQWVQKMSGKGLK

WIGWMNTQSEVPKYAEEFKGRIAFSLETAASTAYLQINNLKTEDTATYFCAKSVYFNWRYFDVWGA

GTTVTVSSAKTTPPPVYPLA

VH1.4 DNA Sequence:

(SEQ ID NO: 18)

ATGGAATGCAGCTGTGTAATGCTCTTTCTCATGGCAGCAGCTCAAAGTATCCAAGCACAGATCC

AGTTGGTGCAGTCTGGACCTGAGCTGAGGAAGCCTGGAGAGACAGTCAGGATCTCCCGCAAGG

CTTCTGGGTATCCCTTCACAACTGCTGGATTGCAGTGGGTACAGAAGATGTCAGGAAAGGGTTT

GAAATGGATTGGCTGGATGAACACCCAGTCTGAAGTGCCAAAATATGCAGAAGAGTTCAAGGGA

CGGATTGCCTTCTCTTTGGAAACCGCTGCCAGTACTGCATATTTACAGATAAACAACCTCAAAAC

TGAGGACACGGCAACGTATTTCTGTGCGAAATCGGTCTATTTTAACTGGAGATATTTCGATGTCT

GGGGTGCAGGGACCACGGTCACCGTCTCCTCAGCCAAAACGACACCCCCATCCGTCTTCCCCC

TGGCA

VH1.4 Amino Acid Sequence:

(SEQ ID NO: 3)

MECSCVMLFLMAAAQSIQAQIQLVQSGPELRKPGETVRISRKASGYPFTTAGLQWVQKMSGKGLK

WIGWMNTQSEVPKYAEEFKGRIAFSLETAASTAYLQINNLKTEDTATYFCAKSVYFNWRYFDVWGA

GTTVTVSSAKTTPPSVFPLA

VH2.1 DNA Sequence:

(SEQ ID NO: 19)

ATGGGTTGGGTGTGGAACTTGCTATTCCTCATGGCAGCAGCTCAAAGTATCCAAGCACAGATCC

AGCTGGTGCAGTCTGGACCTGAGCTGAGGAAGCCTGGAGAGACAGTCAGGATCTCCTGCAAGG

CTTCTGGGTATCCCTTCACAACTGCTGGATTGCAGTGGGTACAGAAGATGTCAGGAAAGGGTTT

GAAATGGATTGGCTGGATGAACACCCAGTCTGAAGTGCCAAAATATGCAGAAGAGTTCAAGGGA

CGGATTGCCTTCTCTTTGGAAACCGCTGCCAGTACTGCATATTTACAGATAAACAACCTCAAAAC

TGAGGACACGGCAACGTATTTCTGTGCGAAATCGGTCTATTTTAACTGGAGATATTTCGATGTCT

GGGGTGCAGGGACCACGGTCACCGTCTCCTCAGCCAAAACGACACCCCCACCCGTCTATCCAC

TGGTC

-continued

VH2.1 Amino Acid Sequence:
(SEQ ID NO: 5)
MGWVWNLLFLMAAAQSIQAQIQLVQSGPELRKPGETVRISCKASGYPFTTAGLQWVQKMSGKGLK

WIGWMNTQSEVPKYAEEFKGRIAFSLETAASTAYLQINNLKTEDTATYFCAKSVYFNWRYFDVWGA

GTTVTVSSAKTTPPPVYPLV

VH1.2 DNA Sequence:
(SEQ ID NO: 20)
ATGGATTGGGTGTGGACCTTGCCATTCCTCATGGCAGCAGCTCAAAGTATCCAAGCACAGATCC

AGTTGGTGCAGTCTGGACCTGAGCTGAGGAAGCCTGGAGAGACAGTCAGGATCTCCTGCAAGG

CTTCTGGGTATCCCTTCACAACTGCTGGATTGCAGTGGGTACAGAAGATGTCAGGAAAGGGTTT

GAAATGGATTGGCTGGATGAACACCCAGTCTGAAGTGCCAAAATATGCAGAAGAGTTCAAGGGA

CGGATTGCCTTCTCTTTGGAAACCGCTGCCAGTACTGCATATTTACAGATAAACAACCTCAAAAC

TGAGGACACGGCAACGTATTTCTGTGCGAAATCGGTCTATTTTAACTGGAGATATTTCGATGTCT

GGGGTGCAGGGACCACGGTCACCGTCTCCTCAGCCAAAACGACACCCCCATCTGTCTATCCAC

TGGCC

VH1.2 Amino Acid Sequence:
(SEQ ID NO: 8)
MDWVWTLPFLMAAAQSIQAQIQLVQSGPELRKPGETVRISCKASGYPFTTAGLQWVQKMSGKGLK

WIGWMNTQSEVPKYAEEFKGRIAFSLETAASTAYLQINNLKTEDTATYFCAKSVYFNWRYFDVWGA

GTTVTVSSAKTTPPSVYPLA

VH2.3 DNA Sequence:
(SEQ ID NO: 21)
ATGGGTTGGGTGTGGAACTTGCCATTCCTCATGGCAGCAGCTCAAAGTATCCAAGCACAGATCC

AGTTGGTGCAGTCTGGACCTGAGCTGAGGAAGCCTGGAGAGACAGTCAGGATCTCCTGCAAGG

CTTCTGGGTATCCCTTCACAACTGCTGGATTGCAGTGGGTACAGAAGATGTCAGGAAAGGGTTT

GAAATGGATTGGCTGGATGAACACCCAGTCTGAAGTACCAAAATATGCAGAAGAGTTCAAGGGA

CGGATTGCCTTCTCTTTGGAAACCGCTGCCAGCACTGCATATTTACAGATAAACAACCTCAAAAC

TGAGGACACGGCAACGTATTTCTGTGCGAAATCGGTCTATTTTAACTGGAGATATTTCGATGTCT

GGGGTGCAGGGACCACGGTCACCGTCTCCTCAGCCAAAACGACACCCCCACCCGTCTATCCAT

TGGCC

VH2.3 Amino Acid Sequence:
(SEQ ID NO: 7)
MGWVWNLPFLMAAAQSIQAQIQLVQSGPELRKPGETVRISCKASGYPFTTAGLQWVQKMSGKGLK

WIGWMNTQSEVPKYAEEFKGRIAFSLETAASTAYLQINNLKTEDTATYFCAKSVYFNWRYFDVWGA

GTTVTVSSAKTTPPPVYPLA

VH2.4 DNA Sequence:
(SEQ ID NO: 22)
ATGGATTGGCTGTGGAACTTGCCATTCCTCATGGCAGCAGCTCAAAGTATCCAAGCACAGATCC

AGTTGGTGCAGTCTGGACCTGAGCTGAGGAAGCCTGGAGAGACAGTCAGGATCTCCTGCAAGG

CTTCTGGGTATCCCTTCACAACTGCTGGATTGCAGTGGGTACAGAAGATGTCAGGAAAGGGTTT

GAAATGGATTGGCTGGATGAACACCCAGTCTGAAGTGCCAAAATATGCAGAAGAGTTCAAGGGA

CGGATTGCCTTCTCTTTGGAAACCGCTGCCAGTACTGCATATTTACAGATAAACAACCTCAAAAC

TGAGGACACGGCAACGTATTTCTGTGCGAAATCGGTCTATTTTAACTGGAGATATTTCGATGTCT

GGGGTGCAGGGACCACGGTCACCGTCTCCTCAGCCAAAACGACACCCCCACCCGTCTATCCAC

TGGCC

-continued

VH2.4 Amino Acid Sequence:
(SEQ ID NO: 9)
MDWLWNLPFLMAAAQSIQAQIQLVQSGPELRKPGETVRISCKASGYPFTTAGLQWVQKMSGKGLK

WIGWMNTQSEVPKYAEEFKGRIAFSLETAASTAYLQINNLKTEDTATYFCAKSVYFNWRYFDVWGA

GTTVTVSSAKTTPPPVYPLA

VH2.5 DNA Sequence:
(SEQ ID NO: 23)
ATGGGTTGGGTGTGGACCTTGCCATTCCTCATGGCAGCAGCTCAAAGTATCCAAGCACAGATCC

AGTTGGTGCAGTCTGGACCTGAGCTGAGGAAGCCTGGAGAGACAGTCAGGATCTCCTGCAAGG

CTTCTGGGTATCCCTTCACAACTGCTGGATTGCAGTGGGTACAGAAGATGTCAGGAAAGGGTTT

GAAATGGATTGGCTGGATGAACACCCAGTCTGAAGTGCCAAAATATGCAGAAGAGTTCAAGGGA

CGGATTGCCTTCTCTTTGGAAACCGCTGCCAGTACTGCATATTTACAGATAAACAACCTCAAAAC

TGAGGACACGGCGACGTATTTCTGTGCGAAATCGGTCTATTTTAACTGGAGATATTTCGATGTCT

GGGGTGCAGGGACCACGGTCACCGTCTCCTCAGCCAAAACGACACCCCCACCCGTCTATCCCC

TGGTC

VH2.5 Amino Acid Sequence:
(SEQ ID NO: 6)
MGWVWTLPFLMAAAQSIQAQIQLVQSGPELRKPGETVRISCKASGYPFTTAGLQWVQKMSGKGLK

WIGWMNTQSEVPKYAEEFKGRIAFSLETAASTAYLQINNLKTEDTATYFCAKSVYFNWRYFDVWGA

GTTVTVSSAKTTPPPVYPLV

VL Sequencing Results:

VK1.1 DNA Sequence:
(SEQ ID NO: 24)
ATGAGGGCCCCTGCTCAGTTTCTTGGGCTTTTGCTTCTCTGGACTTCAGCCTCCAGATGTGACA

TTGTGATGACTCAGTCTCCAGCCACCCTGTCTGTGACTCCAGGAGATAGAGTCTCTCTTTCCTG

CAGGGCCAGCCAGAGTATTAGCGACTACTTATCCTGGTATCAACAAAGATCTCATGAGTCTCCA

AGGCTTATCATCAAATATGCTTCCCAATCCATCTCTGGGATCCCCTCCAGGTTCAGTGGCAGTG

GATCAGGGTCAGACTTCACTCTCAGTATCAACAGTGTGGAACCTGAAGATGTTGGAGTGTATTA

CTGTCAACATGGTCACAGCTTTCCGCTCACGTTCGGTTCTGGGACCAAGCTGGAGCTGAAACG

GGCTGATGCTGCACCAACTGTATCCATCTTCCCACCATCCAGTGAGCAGTTAACATCTGGAGGT

GCCTCAGTCGTGTGCTTCTTGAACAACTTCTACCCCAAAGA

VK1.1 Amino Acid Sequence:
(SEQ ID NO: 10)
MRAPAQFLGLLLLWTSASRCDIVMTQSPATLSVTPGDRVSLSCRASQSISDYLSWYQQRSHESPRLI

IKYASQSISGIPSRFSGSGSGSDFTLSINSVEPEDVGVYYCQHGHSFPLTFGSGTKLELKRADAAPTV

SIFPPSSEQLTSGGASVVCFLNNFYPK

VK1.3 DNA Sequence:
(SEQ ID NO: 25)
ATGAGGTCCCCTGCTCAGTTCCTTGGGCTTTTGCTTTTCTGGACTTCAGCCTCCAGATGTGACAT

TGTGATGACTCAGTCTCCAGCCACCCTGTCTGTGACTCCAGGAGATAGAGTCTCTCTTTCCTGC

AGGGCCAGCCAGAGTATTAGCGACTACTTATCCTGGTATCAACAAAGATCTCATGAGTCTCCAA

GGCTTATCATCAAATATGCTTCCCAATCCATCTCTGGGATCCCCTCCAGGTTCAGTGGCAGTGG

ATCAGGGTCAGACTTCACTCTCAGTATCAACAGTGTGGAACCTGAAGATGTTGGAGTGTATTACT

GTCAACATGGTCACAGCTTTCCGCTCACGTTCGGTTCTGGGACCAAGCTGGAGCTGAAACGGG

CTGATGCTGCACCAACTGTATCCATCTTCCCACCATCCAGTGAGCAGTTAACATCTGGAGGTGC

CTCAGTCGTGTGCTTCTTGAACAACTTCTACCCCAAA

VK1.3 Amino Acid Sequence:
(SEQ ID NO: 12)
MRSPAQFLGLLLFWTSASRCDIVMTQSPATLSVTPGDRVSLSCRASQSISDYLSWYQQRSHESPRLI

IKYASQSISGIPSRFSGSGSGSDFTLSINSVEPEDVGVYYCQHGHSFPLTFGSGTKLELKRADAAPTV

SIFPPSSEQLTSGGASVVCFLNNFYPK

VK1.4 DNA Sequence:
(SEQ ID NO: 26)
ATGAGGTCCCCAGCTCAGTTTCTGGGGCTTTTGCTTTTCTGGACTTCAGCCTCCAGATGTGACA

TTGTGATGACTCAGTCTCCAGCCACCCTGTCTGTGACTCCAGGAGATAGAGTCTCTCTTTCCTG

CAGGGCCAGCCAGAGTATTAGCGACTACTTATCCTGGTATCAACAAAGATCTCATGAGTCTCCA

AGGCTTATCATCAAATATGCTTCCCAATCCATCTCTGGGATCCCCTCCAGGTTCAGTGGCAGTG

GATCAGGGTCAGACTTCACTCTCAGTATCAACAGTGTGGAACCTGAAGATGTTGGAGTGTATTA

CTGTCAACATGGTCACAGCTTTCCGCTCACGTTCGGTTCTGGGACCAAGCTGGAGCTGAAACG

GGCTGATGCTGCACCAACTGTATCCATCTTCCCACCATCCAGTGAGCAGTTAACATCTGGAGGT

GCCTCAGTCGTGTGCTTCTTGAACAACTTCTACCCCAGAGA

VK1.4 Amino Acid Sequence:
(SEQ ID NO: 13)
MRSPAQFLGLLLFWTSASRCDIVMTQSPATLSVTPGDRVSLSCRASQSISDYLSWYQQRSHESPRLI

IKYASQSISGIPSRFSGSGSGSDFTLSINSVEPEDVGVYYCQHGHSFPLTFGSGTKLELKRADAAPTV

SIFPPSSEQLTSGGASVVCFLNNFYPR

VK1.5 DNA Sequence:
(SEQ ID NO: 27)
ATGAGGGCCCCTGCTCAGCTCCTGGGGCTTTTGCTTTTCTGGACTTCAGCCTCCAGATGTGACA

TTGTGATGACTCAGTCTCCAGCCACCCTGTCTGTGACTCCAGGAGATAGAGTCTCTCTTTCCTG

CAGGGCCAGCCAGAGTATTAGCGACTACTTATCCTGGTATCAACAAAGATCTCATGAGTCTCCA

AGGCTTATCATCAAATATGCTTCCCAATCCATCTCTGGGATCCCCTCCAGGTTCAGTGGCAGTG

GATCAGGGTCAGACTTCACTCTCAATATCAACAGTGTGGAACCTGAAGATGTTGGAGTGTATTAC

TGTCAACATGGTCACAGCTTTCCGCTCACGTTCGGTTCTGGGACCAAGCTGGAGCTGAAACGG

GCTGATGCTGCACCAACTGTATCCATCTTCCCACCATCCAGTGAGCAGTTAACATCTGGAGGTG

CCTCAGTCGTGTGCTTCTTGAACAACTTCTATCCCAAAGA

VK1.5 Amino Acid Sequence:
(SEQ ID NO: 11)
MRAPAQLLGLLLFWTSASRCDIVMTQSPATLSVTPGDRVSLSCRASQSISDYLSWYQQRSHESPRLI

IKYASQSISGIPSRFSGSGSGSDFTLNINSVEPEDVGVYYCQHGHSFPLTFGSGTKLELKRADAAPTV

SIFPPSSEQLTSGGASVVCFLNNFYPK

VK2.1 DNA Sequence:
(SEQ ID NO: 28)
ATGGTATCCTCAGCTCAGTTCCTTGGACTTTTGCTTTTCTGGACTTCAGCCTCCAGATGTGACAT

TGTGATGACTCAGTCTCCAGCCACCCTGTCTGTGACTCCAGGAGATAGAGTCTCTCTTTCCTGC

AGGGCCAGCCAGAGTATTAGCGACTACTTATCCTGGTATCAACAAAGATCTCATGAGTCTCCAA

GGCTTATCATCAAATATGCTTCCCAATCCATCTCTGGGATCCCCTCCAGGTTCAGTGGCAGTGG

ATCAGGGTCAGACTTCACTCTCAGTATCAACAGTGTGGAACCTGAAGATGTTGGAGTGTATTACT

GTCAACATGGTCACAGCTTTCCGCTCACGTTCGGTTCTGGGACCAAGCTGGAGCTGAAACGGG

CTGATGCTGCACCAACTGTATCCATCTTCCCACCATCCAGTGAGCAGTTAACATCTGGAGGTGC

CTCAGTCGTGTGCTTCTTGAACAACTTCTACCCCAAA

-continued

VK2.1 Amino Acid Sequence:
(SEQ ID NO: 14)
MVSSAQFLGLLLFWTSASRCDIVMTQSPATLSVTPGDRVSLSCRASQSISDYLSWYQQRSHESPRLI

IKYASQSISGIPSRFSGSGSGSDFTLSINSVEPEDVGVYYCQHGHSFPLTFGSGTKLELKRADAAPTV

SIFPPSSEQLTSGGASVVCFLNNFYPK

VK2.6 DNA Sequence:
(SEQ ID NO: 29)
ATGGTGTCCACAGCTCAGTTCCTTGGACTTTTGCTTTTCTGGACTTCAGCCTCCAGATGTGACAT

TGTGATGACTCAGTCTCCAGCCACCCTGTCTGTGACTCCAGGAGATAGAGTCTCTCTTTCCTGC

AGGGCCAGCCAGAGTATTAGCGACTACTTATCCTGGTATCAACAAAGATCTCATGAGTCTCCAA

GGCTTATCATCAAATATGCTTCCCAATCCATCTCTGGGATCCCCTCCAGGTTCAGTGGCAGTGG

ATCAGGGTCAGACTTCACTCTCAGTATCAACAGTGTGGAACCTGAAGATGTTGGAGTGTATTACT

GTCAACATGGTCACAGCTTTCCGCTCACGTTCGGTTCTGGGACCAAGCTGGAGCTGAAACGGG

CTGATGCTGCACCAACTGTATCCATCTTCCCACCATCCAGTGAGCAGTTAACATCTGGAGGTGC

CTCAGTCGTGTGCTTCTTGAACAACTTCTACCCCAGAGA

VK2.6 Amino Acid Sequence:
(SEQ ID NO: 15)
MVSTAQFLGLLLFWTSASRCDIVMTQSPATLSVTPGDRVSLSCRASQSISDYLSWYQQRSHESPRLII

KYASQSISGIPSRFSGSGSGSDFTLSINSVEPEDVGVYYCQHGHSFPLTFGSGTKLELKRADAAPTV

SIFPPSSEQLTSGGASVVCFLNNFYPR

Example 4—NLRP3 Antigen Synthesis

Design of a peptide (antigen) to NLRP3 that will generate an antibody response capable of inhibiting formation of the NLRP3 inflammasome.

The NLRP-3 inflammasome is a heterogenous protein complex that forms in mammalian cells in response to inflammatory stimulus, the ability to regulate and attenuate its formation could have important therapeutic potential for a range of inflammatory disorders. A peptide will be designed, derived from the NALP3 protein sequence which should generate antibodies capable of blocking the binding of NALP3 to the other protein components in the NLRP3 inflammasome complex.

NLRP3 activation occurs by the self-assembly of NLRP protein with ASC, which is a hetero-complex of CARD, PYD and Caspase-1 domains. NLRP3 and ASC interact through their respective PYD domains, which contain a large proportion of highly conserved charged amino acid residues which interact to form electrostatic interactions, which stabilize the complex—see FIG. 15.

FIG. 16 shows sequence alignment using CLUSTAL 0 (1.2.4) of the consensus sequences of C-terminal domains of human and mouse NALP (NLRP) proteins. Red indicates a residue recognized as essential for NLRP/ASC interaction by site-directed mutagenesis (Vajjhala et al, 2012).

Peptide selection was concentrated on the sequence region from 1-61 which has been studied extensively and is involved in the interaction with ASC (Vajjhala et al, 2012). The region has also been well modelled by crystallography, with a number of PDB structures available for this domain. PDB model 3QF2, which consists of the PYR domain of NLRP3 was selected as the most useful PDB structural reference. Initial peptide candidate sequences were selected on the basis of accessibility and visibility as potential epitopes, and also degree of similarity between mouse and human sequence, whilst maintaining difference with other NLRP variants. These initial 3 peptides were modelled into 3D structures using NovaFold.

NovaFold Analysis

NovaFold is a 3D protein modelling software that uses the I-TASSER algorithm, a combination of template based threading (from PDB) and ab initio methods to predict the folding of a protein or peptide. It is used in this context to predict the presence of secondary structural features within a peptide which are known to be exhibited by the sequence in situ within the parent protein. This can help optimise the selection of a peptide sequence which best reflects the folding and proximity based relationships within the parent protein, helping to maximize the potential of the immunogenic protein resulting in an antibody with full activity towards the corresponding epitope in the full length protein.

Modelling of Peptides and Alignment

Four distinct sequences were modelled using NovaFold, and the resulting highest scoring models were assessed and then aligned to the parent NLRP3 structure as represented by PDB: 3QF2.

TABLE 2

Comparison of alignment and structural features of peptide candidates modelled using Novafold 12.0 and aligned to NLRP3 structure PDB: 3QF2 using Protean 3D, version 14.0.1.

| Peptide ID | Location in Consensus sequence | Sequence | Secondary Structure |
|---|---|---|---|
| FUS_746_001 | 30-53 | EDYPPQKGCIPLPRGQTEKADHVD (SEQ ID NO: 30) | α-helix |
| FUS_746_002 | 35-53 | QKGCIPLPRGQTEKADHVD (SEQ ID NO: 31) | none |

TABLE 2-continued

Comparison of alignment and structural features of peptide candidates modelled using Novafold 12.0 and aligned to NLRP3 structure PDB: 3QF2 using Protean 3D, version 14.0.1.

| Peptide ID | Location in Consensus sequence | Sequence | Secondary Structure |
|---|---|---|---|
| FUS_746_003 | 35-49 | QKGCIPLPRGQTEKA (SEQ ID NO: 32) | none |

The modelling and comparison indicates that peptide FUS_746_001 is the preferred candidate for use as a peptide immunogen. In addition to demonstrating the greatest alignment with the model of the parent protein, it also demonstrates high similarity in prediction of secondary structure and is an accessible epitopic target.

Peptide FUS_746_001 Alignment using a Novafold predicted structure is shown in FIG. 17.

Conclusion

The modelling of the software should always be taken as advisory, rather than definitive and interpreted on this basis, particularly if strong secondary structural features are not known to be found within the parent molecule. With this in mind, however, the modelling suggests that peptide FUS_746_001, sequence EDYPPQKGCIPLPRGQTEKADHVD (SEQ ID NO: 30) would be a best candidate for selection as the immunogen for this project on the basis of alignment to the parent protein, and predicted antigenicity. The peptide also shows only a few points of difference between the mouse and human sequence, which supports the production of an antibody response in mice that may allow for cross reactivity between these species, which is also a desirable feature, whilst minimising cross reactivity to other NLRP types. Note: It is recommended to add an N-terminal Cys residue for cross-linking to KLH.

REFERENCES

Zhang, Y., 2008. I-TASSER server for protein 3D structure prediction. *BMC Bioinformatics,* 23 January9(40).

Vajjhala, P. R., Mirams, R. E., and Hill, J. M. (2012). Multiple binding sites on the pyrin domain of ASC protein allow self-association and interaction with NLRP3 protein. *J. Biol. Chem.* 287, 41732-41743

NLRP3 Antigen Synthesis

The NLRP3 peptide was synthesised by bioSynthesis Inc, Texas, conjugated to KLH using maleimide coupling through an additional C-terminal cysteine residue.

ELISA screening results of 1st bleed from mice immunised with NLRP3 immunogen—see FIG. 18.

Example 5—Generation of a Monoclonal Antibody Against NLRP3

A population of 5 mice were immunised and screened for positive immune responses. After selecting a suitable candidate for fusion, splenocytes were fused with partner cells to produce a population of hybridomas. This population underwent a series of limiting dilutions and screening assays to produce fully monoclonal cell lines.

Cell Line Nomenclature

The product name "F226 7A7-1E1-2D5" refers to one of the 10 chosen monoclonal hybridoma cell lines. The name is comprised of components describing the production pathway at each stage. Each hybridoma selected from the post-fusion screening and each limiting dilution was given a number corresponding to the plate number and well location on that plate for which the hybridoma was chosen (i.e. 7A7-1E1-2D5). This nomenclature traces the derivation of each individual hybridoma allowing for clear differentiation in the screening process.

Abbreviations

| | |
|---|---|
| Ab | Antibody |
| DMSO | Dimethyl Sulfoxide |
| FCS | Fetal Calf Serum |
| ELISA | Enzyme-Linked Immunosorbent Assay |
| RT | Room Temperature |
| OD | Optical Density |
| PBST | Phosphate-buffered saline + 1% Tween 20 |
| PBS | Phosphate-buffered saline |
| RPM | Revolutions per minute |
| NP, LP, RP, LRP, 2LP | Mouse Identification: No Punch, Left Punch, Right Punch Left/Right Punch, 2 Left Punches |
| HAT | Hypoxanthine, Aminopterin, Thymidine supplement |
| HATR Media[2] | DMEM supplemented with 2% Roche (HFCS), 2% HAT, 1% Pen/Strep, 1% L-Glutamine |
| SFM | Serum Free Medium |
| PEG | Polyethylene Glycol |
| GAM-HRP | Goat Anti-Mouse-Horse Radish Peroxidase |
| HT | Hypoxanthine and Thymidine |
| LD1 | First Limiting Dilution |
| LD2 | Second Limiting Dilution |

[1] This is the media that was used for all cultures following fusion and screening.

Materials

Reagents and Media

| Reagent | Supplier | Catalogue No. |
|---|---|---|
| L-glutamine | Gibco | 25030-024 |
| HAT Supplement | Gibco | 21060-017 |
| HFCS | Roche | 11363735001 |
| DMEM Glutamax | Gibco | 61965-059 |
| Penicillin/Streptomycin | Gibco | 15140-122 |
| FCS | Gibco | 16000.044 |
| DMSO | Sigma | D2650 |
| Trypan Blue | Sigma | T8154 |
| PEG | Sigma | 10783641001 |
| Freund's Adjuvant Complete | Sigma | F5881 |
| Freund's Adjuvant Incomplete | Sigma | F5506 |
| Sodium Hydrogen Carbonate | VWR | 27778.260 |
| Sodium Carbonate | Sigma | S2127-500G |
| Powdered Milk | Marvel | Original Dried Skimmed |
| Tween 20 (10%) | Sigma | P1379-1L |
| GAM-HRP (Fc Specific) | Sigma | A2554 |
| TMB | Biopanda | TMB-S-002 |
| Mr. Frosty | Nalgene | 55710-200 |

Disposables

| Name | Supplier | Catalogue No. |
|---|---|---|
| 25 cm$^2$ static flasks | Corning | 430639 |
| 75 cm$^2$ static flasks | Corning | 430641 |
| 96-well plate sterile | Corning | 3595 |
| 96-well plate sterile TPP | Primer | 92696T |

| Name | Supplier | Catalogue No. |
| --- | --- | --- |
| Cryovials | Scientific Fisher | 366656 |
| Maxi Sorb 96-well plates | Scientific Nunc | 442404 |

Equipment $CO_2$ Cell culture static incubators (SANYO)
Plate reader Sunrise (Tecan)
Centurion Scientific K40R Centrifuge
Grant-Bio Multishaker PSU 20

Methods

Antigen Preparation

Once the immunogen; NLRP3 peptide-KLH conjugate (bioSynthesis Inc, Texas) was received, these solutions were diluted to 400 µg/ml in sterile, EF-PBS and aliquoted in volumes of 600 µl for immunisation and 150 µl for boosts and ELISA screening. These aliquots were labelled and stored at −20° C.

Immunisations

A population of 5 BalbC mice were immunised subcutaneously with 200 µl of a 1:1 emulsion of Freund's Adjuvant Complete (Sigma) and a 600 µl aliquot of NLRP3 peptide-KLH conjugate prepared herein. Two weeks after the $1^{st}$ immunisation, the population was immunized with a $2^{nd}$ injection at the same volumes and concentrations as the original injection only using Freund's Adjuvant Incomplete (Sigma) instead. One week after the $2^{nd}$ immunisation, the mice were tagged by ear punches (NP, RP, LP, LRP, 2LP), and test bleeds were screened as described herein for preliminary results. Three weeks after the $2^{nd}$ immunisation, the population was immunised a $3^{rd}$ time using the same method as the $2^{nd}$ injection. One week after the $3^{rd}$ immunisation test bleeds were screened, and RP was then selected for fusion.

Test Bleed ELISAs

Tail bleeds were taken from the population of 5 BalbC mice and centrifuged at 8000 rpm for 10 min at RT. The blood serum from each mouse was collected, loaded onto the plate the same day as screening, and stored at −20° C. This screening was performed twice for the selection of a suitable mouse for fusion.

The day prior to screening, a Maxi Sorb plate was coated by adding 100 µl/well of 50 mM sodium carbonate coating buffer (pH 9.5) containing the free NLRP3 peptide at 1 µg/ml. A separate coating solution was prepared by diluting APO-A1 in the same coating buffer at 1 µg/ml. These solutions were loaded onto the plate in alternating rows so as to provide two wells to load each sample that demonstrates a positive and negative result. This plate was incubated overnight at 4° C. in static conditions.

The following morning coating buffer was removed, and 200 µl/well of blocking solution (4.0% w/v semi skim milk powder, 1×PBS) was added and agitated at 150 rpm for 2 hr at RT. The plate was washed three times with PBS-T (0.1% v/v Tween 20). PBS was loaded into each well at 100 µl/well, and 1 µl of each test bleed serum was loaded into each positive and negative well. The plate was incubated at 150 rpm (Grant Shaker) for 2 hrs at room temperature. These samples were then removed and washed four times with PBS-T. 100 µl/well GAM-HRP diluted 1:5000 (Sigma, UK) was added, and the plate was incubated for 1 hr with agitation at 150 rpm at RT. The secondary antibody was removed, and the plate was washed four times with PBS-T and once in PBS. 100 µl/well of TMB substrate solution was added and incubated at 37° C. for 10 minutes. 50 µl 1M HCl was added per well and the plate immediately read at 450 nm on a Tecan Sunrise plate reader.

After the second test bleed ELISA screening, RP was selected for fusion by expressing the most positive immune response.

Boost Injections

One week after the $3^{rd}$ and final immunization, a boost injection was given to BalbC mouse RP by injecting 100 µl of aliquoted IL-1R at 200 µg/ml without any adjuvant.

Fusion F226

One week before fusion, SP2 cells were broken out from liquid nitrogen and were passaged in 10% FCS DMEM supplemented with 1% Pen/Strep, 1% L-glutamine until 3×12 ml T75 flasks were 75%-90% confluent on the day of fusion. On the day of the fusion, SP2 cells were dislodged by tapping the flask and were centrifuged at 1000 rpm for 5 min at 37° C. The cells were resuspended in 20 ml SFM DMEM, centrifuged again, and resuspended in 10 ml SFM DMEM. SP2 cells were stored in a Sterilin tube in SFM at 37° C., 6% $CO_2$ until needed.

After euthanasia, the spleen was aseptically removed from the mouse that showed the strongest immune response. Splenocytes were extracted by puncturing both ends of the spleen with a fine gauge needle and flushing 10-15 ml SFM DMEM. Splenocytes were transferred to a sterilin tube and washed twice with 20 ml serum free DMEM by centrifugation at 1300 rpm for 5 min at 37° C. and gently removing the supernatant. The splenocytes were resuspended in 10 ml Serum free DMEM in a sterilin tube.

Using the SP2 cells stored at 37° C., the SP2 cells were added to the splenocytes. This SP2/splenocytes culture was centrifuged at 1300 rpm for 5 min at 37° C. After discarding the supernatant, 1 ml PEG was added to the SP2/splenocytes culture dropwise while stirring continuously over a period of 3 min. 1 ml SFM DMEM was added to the fusion mixture and stirred for 4 min. 10 ml SFM DMEM was added dropwise to the fresh culture and incubated for in 37° C. water bath for 5 min. The cells were then centrifuged at 1000 rpm for 5 min at 37° C. The pellet was resuspended in 200 mL HATR media and was plated at 200 µl/well in 10×96 well culture plates which were incubated 11 days at 37° C. in 6% $CO_2$ prior to screening.

Post-Fusion Screening and Post-LD Screening Eleven days after fusion, protoclones were screened by ELISA. 20× Maxi Sorb 96 well plates were coated as described in section 0 using APO-A1 at 1 µg/ml as the negative control for specificity. The coating solution was removed and the plates were blocked as described herein. Samples were prepared by removing 160 µl of supernatant from each well of the ten fusion plates, limiting dilution plates, or 24-well plates and transferring to fresh 96 well culture plates containing 50 µl 1×PBS. After 2 hours of blocking, the blocking solution was removed, and the plates were washed 3× with PBS-T. The samples from each dilution plate were loaded onto the ELISA plates at 100 µl/well by adding 1 row from each dilution plate per 2 rows on the ELISA plates to account for specificity of the coating antigens. Two wells per ELISA were incubated with 100 µl 1×PBS as a negative control. These samples were incubated at 150 rpm for 2 hours at room temperature.

Limiting Dilutions

Once the hybridoma populations were expanded in 24-well plates and growing well, a secondary screen was performed to select the most specific and highest producing populations for rounds of limiting dilutions.

Both limiting dilutions were performed for 1-3 protoclones each by seeding 2-4×96-well plates at 1 cell/well in 200 µl culture/well. The plates were prepared by counting each culture in the 24-well plate and were diluted 10× as an intermediate dilution, then were diluted to 200 cells in 40 ml. The culture was plated at 200 µl/well and left to incubate at 37° C., 6% $CO_2$ for 7-10 days until the wells were 80%-90% confluent. Each well for both limiting dilutions were screened by ELISA as described in section 0.

Final Clone Selection

Following the second limiting dilution, 10 clones were selected for expansion in a 24 well plate. Each clone was left to grow in 37° C., 6% $CO_2$ for 6 days until each well became 80%-90% confluent. When the clones were well established in the 24-well plates, each clone at 1 ml/well was transferred to a T25 flask containing 5 ml fresh 10% HATR DMEM for cryopreservation.

Cryopreservation of Monoclonal Cell Lines

Once the clones were well established (80%-90% confluency) in T25 flasks, each 5 ml culture was centrifuged at 1000 rpm for 5 min at 37° C. and was resuspended in 1 ml of fresh 10% DMEM HATR media. Each 1 ml culture was transferred to a cryovial containing 300 µl of a 1:1 ratio of FCS to DMSO. The vials were sealed and placed in a Mr. Frosty and transferred to the −70° C. freezer for short-term storage.

Cell Preparation for Sequencing

Anti-NLRP3 produced from clone F226 7A7-1E1-2D5 was selected for sequencing. Once the culture was confluent in the T25 flask, the supernatant was discarded. The cells were dislodged by cell scraping into 2 ml fresh media and were centrifuged at 7,600 rpm for 5 min at RT. The supernatant was then discarded and the pellet was flash frozen in liquid nitrogen and placed in −70° C. until ready for mRNA extraction.

Immunisation and Screening of Test Bleeds

A colony of mice were immunised with NLRP3 peptide-KLH conjugate (designed by bioinformatics and synthesised by bioSynthesis Inc, Texas) and regular test bleeds were taken over an 11 week period. Test bleeds were then screened against the antigen.

Upon identification of positive mice, a fusion was performed and supernatant from hybridoma clones were then validated. The specific antibodies then underwent limiting dilution and cloning to produce a stable hybridoma cell line against NLRP3.

The antibodies were screened using ELISA against the target protein—NLRP3—and clones with a signal of at least 3 times the background were selected. Antibodies from 24 clones were selected and further in house testing was performed to pick the best 6 clones.

Results

Test Bleed 1

One week after the $2^{nd}$ immunisation, a tail bleed was taken from each of the 5 mice and screened against unconjugated NLRP3 peptide and APO-A1 for determination of a suitable animal for fusion and a relative specificity of the polyclonal antibody produced—see FIG. 19.

Test Bleed 2

After screening sera from tail bleeds, 2RP was selected for the fusion of its splenocytes to fusion partner SP2 culture as it demonstrated the best immune response—see FIG. 20.

Post-Fusion Screening

Once the wells in each plate had reached 70%-80% confluency, the plates were screened by ELISA against NLRP3 peptide and APO-A1. The hybridoma population producing the highest responses were selected for expansion in a 24-well plate—see FIG. 21.

$1^{st}$ 24-Well Plate Screening

Clones were selected from the post-fusion screening and were arrayed into a 24 well plate for expansion followed by a secondary screening that determines suitable protoclones for the first round of limiting dilutions. 3 clones were selected and limiting dilutions prepared—see FIG. 22.

Limiting Dilution 1 Screening

Once the $1^{st}$ limiting dilution plates were confluent, the limiting dilution was screened by ELISA against NLRP3 Peptide and APO-A1. 31 hybridoma populations were selected from F226 5B7 and 7A7 that demonstrated the highest and most specific response. No clones from 3D4 were suitable—see FIG. 23.

$2^{nd}$ 24-Well Plate Screening

When the clones became confluent in the 24-well plate, each clone was screened by ELISA against NLRP3 peptide and APO-A1, F226 5B7-1E10, 5B7-1G2, 7A7-1C4 and 7A7-1E1 selected for the $2^{nd}$ round of limiting dilution over 2×96 well plates per clone—see FIG. 24.

Limiting Dilution 2 Screening

Once the wells in each plate had reached 70%-80% confluency, the plates were screened by ELISA against NLRP3 peptide and APO-A1. The 24 hybridoma populations producing the highest response and highest specificity were selected for expansion in a 24-well plate and cryopreservation—see FIG. 25.

Dot Blot analysis is shown in FIG. 26. Dot blots were performed using protein lysates from THP-1 macrophages to test supernatant containing the anti NLRP3 monoclonal antibody collected from the best 24 clones from a fusion hybridoma cell line (A25=positive control commercial anti NLRP3 monoclonal antibody (R&D Systems), A26=negative control PBS). Clones 6, 11, 15, 16, 18 and 20 were selected and further tested by Western blotting.

Western Blot Analysis is shown in FIG. 27. Western blots were performed using protein lysates from THP-1 macrophages to test supernatant containing anti-NLRP3 monoclonal antibody collected from the best 6 clones from a fusion hybridoma cell line untreated (lane 1) and stimulated with LPS and ATP (lane 2, (protein ladder lane 3)). Clone 18 was selected for sequencing and was used in the bispecific monoclonal antibody development.

Conclusions

The aim was to produce a range of antibodies against NLRP3 that were functional in preventing assembly of the NLRP3 inflammasome. Once the mice were immunised and screened, 2RP was selected for fusion. 24 monoclonal hybridoma cell lines were produced from two rounds of limiting dilutions. Each population was selected by highest production and highest specificity for NLRP3. The clone F226 7A7-1E1-2D5 was shown to be most active in preventing NLRP3 assembly in the in vitro assay. These final cell lines have been frozen down, and the antibody expressed by this 7A7-1E1-2D5 will be sequenced for the next stage in the production of the bi-specific, InflaMab.

Example 6—NLRP3 Monoclonal Sequencing mRNA was extracted from the hybridoma cell pellets on 23/02/16. Total RNA was extracted from the pellets using Fusion Antibodies Ltd in-house RNA extraction protocol (see Example 3).

RT-PCR cDNA was created from the RNA by reverse-transcription with an oligo(dT) primer. PCR reactions are set up using variable domain primers to amplify both the VH and $V_L$ regions of the monoclonal antibody DNA giving the following bands (see FIG. 28):

The VH and VL products were cloned into the Invitrogen sequencing vector pCR2.1 and transformed into TOP10 cells and screened by PCR for positive transformants. Selected colonies were picked and analyzed by DNA sequencing on an ABI3130xl Genetic Analyzer, the result may be seen below.

Sequencing Results

Heavy Chain $V_H$ Amino Acid Sequence Alignment:

```
                              1                                                  50
VH1.1       (1)   MNFGLSLVFLVLVLKGAQCEVQLVESGGGLVKPGGSLKLSCAASGFTFSD
VH3.7       (1)   -------FLVLVLKGVQCEVQLVESGGGLVKPGGSLKLSCAASGFTFSD
VH3.4       (1)   MDFGLSRVFLVLVLKGVQCEVQLVESGGGLVKPGGSLKLSCAASGFTFSD
VH3.1       (1)   MDFGLSWVFLVLVLKGVQCEVQLVESGGGLVKPGGSLKLSCAASGFTFSD
VH3.5       (1)   MDFGLSWVFLVLVLKGVQCEVQLVESGGGLVKPGGSLKLSCAASGFTFSD
VH3.8       (1)   MDFGLSWVFLVLVLKGVQCEVQLVESGGGLVKPGGSLKLSCAASGFTFSD
Consensus   (1)   MDFGLSRVFLVLVLKGVQCEVQLVESGGGLVKPGGSLKLSCAASGFTFSD 51                                                 100
VH1.1       (51)  YYMYWVRQTPEKRLEWVATISDGGTYTYYPDSVKGRFTISRDNAKNNLYL
VH3.7       (51)  YYMYWVRQTPEKRLEWVATISDGGTYTYYPDSVKGRFTISRDNAKNNLYL
VH3.4       (51)  YYMYWVRQTPEKRLEWVATISDGGTYTYYPDSVKGRFTISRDNAKNNLYL
VH3.1       (51)  YYMYWVRQTPEKRLEWVATISDGGTYTYYPDSVKGRFTISRDNAKNNLYL
VH3.5       (51)  YYMYWVRQTPEKRLEWVATISDGGTYTYYPDSVKGRFTISRDNAKNNLYL
VH3.8       (51)  YYMYWVRQTPEKRLEWVATISDGGTYTYYPDSVKGRFTISRDNAKNNLYL
Consensus   (51)  YYMYWVRQTPEKRLEWVATISDGGTYTYYPDSVKGRFTISRDNAKNNLYL 101                                                150
VH1.1       (101) QMNSLK--------------------------------------------
VH3.7       (101) QMNSLKSEDTAMYYCARGWVSTMVKLLSSFPYWGQGTLVTVSAAKTTPPS
VH3.4       (101) QMNSLKSEDTAMYYCARGWVSTMVKLLSSFPYWGQGTLVTVSAAKTTPPS
VH3.1       (101) QMNSLKSEDTAMYYCARGWVSTMVKLLSSFPYWGQGTLVTVSAAKTTPPS
VH3.5       (101) QMNSLKSEDTAMYYCARGWVSTMVKLLSSFPYWGQGTLVTVSAAKTTPPS
VH3.8       (101) QMNSLKSEDTAMYYCARGWVSTMVKLLSSFPYWGQGTLVTVSAAKTTPPS
Consensus   (101) QMNSLKSEDTAMYYCARGWVSTMVKLLSSFPYWGQGTLVTVSAAKTTPPS 151
VH1.1       (151) -----
VH3.7       (151) VYPLA
VH3.4       (151) VYPLA
VH3.1       (151) VYPLA
VH3.5       (151) VYPLA
VH3.8       (151) VYPLA
Consensus   (151) VYPLA VH1.1       (SEQ ID NO: 33)
VH3.7       (SEQ ID NO: 34)
VH3.4       (SEQ ID NO: 35)
VH3.1       (SEQ ID NO: 36)
VH3.5       (SEQ ID NO: 36)
VH3.8       (SEQ ID NO: 36)
Consensus   (SEQ ID NO: 36)

Key to amino acid shading:
Black       non-similar residues
Bold        consensus residue derived from a block of residues at
            a given position
Underlined  residues similar in structure to consensus residue or
            each other when no consensus found
Italicised  consensus residue derived from a completely conserved
            residue at a given position
Underlined/ residue weakly similar to consensus residue at given
italicized  position
```

V_H Consensus Amino Acid Sequence:

(SEQ ID NO: 35)
MDFGLSWVFLVLVLKGVQCEVQLVESGGGLVKPGGSLKLSCAASGFTFSD

YYMYWVRQTPEKRLEWVATISDGGTYTYYPDSVKGRFTISRDNAKNNLYL

QMNSLKSEDTAMYYCARGWVSTMVKLLSSFPYWGQGTLVTVSAAKTTPPS

VYPLA

The variable domain is highlighted in BOLD.

The Complementarity Determining Regions (CDRs) are underlined as determined by the IMGT numbering system (Lefranc, M.-P. et al., Nucleic Acids Research, 27, 209-212 (1999))—see FIG. 29.

Key to amino acid shading, in FIG. 29:

Blue shaded circles are hydrophobic (non-polar) residues in frameworks 1-3 at sites that are hydrophobic in the majority of antibodies.

Yellow shaded circles are proline residues.

Squares are key residues at the start and end of the CDR.

Red amino acids in the framework are structurally conserved amino acids.

Light Chain

V_L Amino Acid Sequence Alignment:

V_L Consensus Amino Acid Sequence:

V_L Consensus Amino Acid Sequence:
(SEQ ID NO: 43)
MAWISLLLSLLALSSGAISQAVVTQESALTTSPGETVTLTCRSSTGAVTT

SNYANWVQEKPDHLFTGLIGGTNNRAPGVPARFSGSLIGDKAALTITGAQ

TEDEAIYFCALWYSNYWVFGGGTKLTVLGQPKSSPSVTLFPPSTEELSL

The variable domain is highlighted in BOLD.

The Complementarity Determining Regions (CDRs) are underlined as determined by the IMGT numbering system (Lefranc, M.-P. et al., Nucleic Acids Research, 27, 209-212 (1999))—see FIG. 30.

Key to amino acid shading, in FIG. 30:

Blue shaded circles are hydrophobic (non-polar) residues in frameworks 1-3 at sites that are hydrophobic in the majority of antibodies.

Yellow shaded circles are proline residues.

Squares are key residues at the start and end of the CDR.

Red amino acids in the framework are structurally conserved amino acids.

```
                    1                                                50
VL1.1      (1)   MAWISLIFSLLALSSGAISQAVVTQESALTTSPGETVTLTCRSSTGAVTT
VL1.6      (1)   MAWISLIFSLLALSSGAISQAVVTQESALTTSPGETVTLTCRSSTGAVTT
VL1.2      (1)   MAWTSLLLSLLALSSGAISQAVVTQESALTTSPGETVTLTCRSSTGAVTT
VL1.7      (1)   MAWTSLLFSLLALSSGAISQAVVTQESALTTSPGETVTLTCRSSTGAVTT
VL1.4      (1)   MAWIPLLFSLLALSSGAISQAVVTQESALTTSPGETVTLTCRSSTGAVTT
VL1.5      (1)   MAWISLLLSLLALSSGAISQAVVTQESALTTSPGETVTLTCRSSTGAVTT
Consensus  (1)   MAWISLLFSLLALSSGAISQAVVTQESALTTSPGETVTLTCRSSTGAVTT 51                                              100
VL1.1     (51)   SNYANWVQEKPDHLFTGLVGGTNNRAPGVPARFSGSLIGDKAALTITGAQ
VL1.6     (51)   SNYANWVQEKPDHLFTGLIGGTSNRAPGVPARFSGSLIGDKAALTITGAQ
VL1.2     (51)   SNYANWVQEKPDHLFTGLIGGTNNRAPGVPARFSGSLIGDKAALTITGAQ
VL1.7     (51)   SNYANWVQEKPDHLFTGLIGGTNNRAPGVPARFSGSLIGDKAALTITGAQ
VL1.4     (51)   SNYANWVQEKPDHLFTGLIGGTNNRAPGVPARFSGSLIGDKAALTITGAQ
VL1.5     (51)   SNYANWVQEKPDHLFTGLIGGTNNRAPGVPARFSGSLIGDKAALTITGAQ
Consensus (51)   SNYANWVQEKPDHLFTGLIGGTNNRAPGVPARFSGSLIGDKAALTITGAQ 101                                             150
VL1.1    (101)   TEDEAIYFCALWYSNYWVFGGGTKLTVLGQPKSSPSVTLFPPSTEELSL
VL1.6    (101)   TEDEAIYFCALWYSNYWVFGGGTKLTVLGQPKSSPSVTLYPPSTKELSL
VL1.2    (101)   TEDEAIYFCALWYSNYWVFGGGTKLTVLGQPKSSPSVTLCPPSSEKLSL
VL1.7    (101)   TEDEAIYFCALWYSNYWVFGGGTKLTVLGQPKSSPSVTLCPPSTEKLSL
VL1.4    (101)   TEDEAIYFCALWYSNYWVFGGGTKLTVLGQPKSSPSVTLFPPSLEKLSL
VL1.5    (101)   TEDEAIYFCALWYSNYWVFGGGTKLTVLGQPKSSPSVTLFPPSTEELSL
Consensus(101)   TEDEAIYFCALWYSNYWVFGGGTKLTVLGQPKSSPSVTLFPPSTEKLSL VL1.1      (SEQ ID NO: 37)
VL1.6      (SEQ ID NO: 38)
VL1.2      (SEQ ID NO: 39)
VL1.7      (SEQ ID NO: 40)
VL1.4      (SEQ ID NO: 41)
VL1.5      (SEQ ID NO: 42)
Consensus  (SEQ ID NO: 43)
```

```
Key to amino acid shading:
Black       non-similar residues
Bold        consensus residue derived from a block of residues at
            a given position
Underlined  residues similar in structure to consensus residue or
            each other when no consensus found
Italicised  consensus residue derived from a completely conserved
            residue at a given position
Underlined/ residue weakly similar to consensus residue at given
italicized  position
```

VH Sequencing results:

VH1.1 DNA Sequence:
(SEQ ID NO: 44)
ATGAACTTCGGGTTGAGCTTGGTTTTCCTTGTCCTTGTTTTAAAAGGTGCCCAGTGTGAAGTGCA

GCTGGTGGAGTCTGGGGGAGGCTTAGTGAAGCCTGGAGGGTCCCTGAAACTCTCCTGTGCAGC

CTCTGGATTCACTTTCAGTGACTATTACATGTATTGGGTTCGCCAGACTCCGGAAAAGAGGCTG

GAGTGGGTCGCAACCATTAGTGATGGTGGTACTTACACCTACTATCCAGACAGTGTGAAGGGGC

GATTCACCATCTCCAGAGACAATGCCAAGAACAACCTTTACCTGCAAATGAACAGTCTGAAG

VH1.1 Amino Acid Sequence:
(SEQ ID NO: 33)
MNFGLSLVFLVLVLKGAQCEVQLVESGGGLVKPGGSLKLSCAASGFTFSDYYMYWVRQTPEKRLE

WVATISDGGTYTYYPDSVKGRFTISRDNAKNNLYLQMNSLK

VH3.1 DNA Sequence:
(SEQ ID NO: 45)
ATGGACTTCGGGTTGAGCTGGGTTTTCCTTGTCCTTGTTTTAAAAGGTGTCCAGTGTGAAGTGCA

GCTGGTGGAGTCTGGGGGAGGCTTAGTGAAGCCTGGAGGGTCCCTGAAACTCTCCTGTGCAGC

CTCTGGATTCACTTTCAGTGACTATTACATGTATTGGGTTCGCCAGACTCCGGAAAAGAGGCTG

GAGTGGGTCGCAACCATTAGTGATGGTGGTACTTACACCTACTATCCAGACAGTGTGAAGGGGC

GATTCACCATCTCCAGAGACAATGCCAAGAACAACCTTTACCTGCAAATGAACAGTCTGAAGTCT

GAGGACACAGCCATGTATTACTGTGCAAGAGGATGGGTTTCTACTATGGTTAAACTTCTTTCCTC

CTTTCCTTACTGGGGCCAAGGGACTCTGGTCACTGTCTCTGCAGCCAAAACGACACCCCCATCT

GTCTATCCACTGGCC

VH3.1 Amino Acid Sequence:
(SEQ ID NO: 36)
MDFGLSWVFLVLVLKGVQCEVQLVESGGGLVKPGGSLKLSCAASGFTFSDYYMYWVRQTPEKRLE

WVATISDGGTYTYYPDSVKGRFTISRDNAKNNLYLQMNSLKSEDTAMYYCARGWVSTMVKLLSSFP

YWGQGTLVTVSAAKTTPPSVYPLA

VH3.4 DNA Sequence:
(SEQ ID NO: 46)
ATGGACTTCGGGCTGAGCAGGGTTTTCCTTGTCCTTGTTTTAAAAGGTGTCCAGTGTGAAGTGC

AGCTGGTGGAGTCTGGGGGAGGCTTAGTGAAGCCTGGAGGGTCCCTGAAACTCTCCTGTGCAG

CCTCTGGATTCACTTTCAGTGACTATTACATGTATTGGGTTCGCCAGACTCCGGAAAAGAGGCT

GGAGTGGGTCGCAACCATTAGTGATGGTGGTACTTACACCTACTATCCAGACAGTGTGAAGGG

GCGATTCACCATCTCCAGAGACAATGCCAAGAACAACCTTTACCTGCAAATGAACAGTCTGAAG

TCTGAGGACACAGCCATGTATTACTGTGCAAGAGGATGGGTTTCTACTATGGTTAAACTTCTTTC

CTCCTTTCCTTACTGGGGCCAAGGGACTCTGGTCACTGTCTCTGCAGCCAAAACGACACCCCCA

TCTGTCTATCCACTGGCC

VH3.4 Amino Acid Sequence:
(SEQ ID NO: 35)
MDFGLSRVFLVLVLKGVQCEVQLVESGGGLVKPGGSLKLSCAASGFTFSDYYMYWVRQTPEKRLE

WVATISDGGTYTYYPDSVKGRFTISRDNAKNNLYLQMNSLKSEDTAMYYCARGWVSTMVKLLSSFP

YWGQGTLVTVSAAKTTPPSVYPLA

VH3.5 DNA Sequence:
(SEQ ID NO: 47)
ATGGACTTCGGGCTGAGCTGGGTTTTCCTTGTCCTTGTTTTAAAAGGTGTCCAGTGTGAAGTGC

AGCTGGTGGAGTCTGGGGGAGGCTTAGTGAAGCCTGGAGGGTCCCTGAAACTCTCCTGTGCAG

CCTCTGGATTCACTTTCAGTGACTATTACATGTATTGGGTTCGCCAGACTCCGGAAAAGAGGCT

GGAGTGGGTCGCAACCATTAGTGATGGTGGTACTTACACCTACTATCCAGACAGTGTGAAGGG

-continued

```
GCGATTCACCATCTCCAGAGACAATGCCAAGAACAACCTTTACCTGCAAATGAACAGTCTGAAG

TCTGAGGACACAGCCATGTATTACTGTGCAAGAGGATGGGTTTCTACTATGGTTAAACTTCTTTC

CTCCTTTCCTTACTGGGGCCAAGGGACTCTGGTCACTGTCTCTGCAGCCAAAACGACACCCCCA

TCTGTCTATCCACTGGCC
```

VH3.5 Amino Acid Sequence:
(SEQ ID NO: 36)
```
MDFGLSWVFLVLVLKGVQCEVQLVESGGGLVKPGGSLKLSCAASGFTFSDYYMYWVRQTPEKRLE

WVATISDGGTYTYYPDSVKGRFTISRDNAKNNLYLQMNSLKSEDTAMYYCARGWVSTMVKLLSSFP

YWGQGTLVTVSAAKTTPPSVYPLA
```

VH3.7 DNA Sequence:
(SEQ ID NO: 48)
```
TTTTCCTTGTCCTTGTTTTAAAAGGTGTCCAGTGTGAAGTGCAGCTGGTGGAGTCTGGGGGAGG

CTTAGTGAAGCCTGGAGGGTCCCTGAAACTCTCCTGTGCAGCCTCTGGATTCACTTTCAGTGAC

TATTACATGTATTGGGTTCGCCAGACTCCGGAAAAGAGGCTGGAGTGGGTCGCAACCATTAGTG

ATGGTGGTACTTACACCTACTATCCAGACAGTGTGAAGGGGCGATTCACCATCTCCAGAGACAA

TGCCAAGAACAACCTTTACCTGCAAATGAACAGTCTGAAGTCTGAGGACACAGCCATGTATTACT

GTGCAAGAGGATGGGTTTCTACTATGGTTAAACTTCTTTCCTCCTTTCCTTACTGGGGCCAAGGG

ACTCTGGTCACTGTCTCTGCAGCCAAAACGACACCCCCATCTGTCTATCCACTGGCC
```

VH3.7 Amino Acid Sequence:
(SEQ ID NO: 33)
```
FLVLVLKGVQCEVQLVESGGGLVKPGGSLKLSCAASGFTFSDYYMYWVRQTPEKRLEWVATISDGG

TYTYYPDSVKGRFTISRDNAKNNLYLQMNSLKSEDTAMYYCARGWVSTMVKLLSSFPYWGQGTLVT

VSAAKTTPPSVYPLA
```

VH3.8 DNA Sequence:
(SEQ ID NO: 49)
```
ATGGACTTCGGGCTGAGCTGGGTTTTCCTTGTCCTTGTTTTAAAAGGTGTCCAGTGTGAAGTGC

AGCTGGTGGAGTCTGGGGGAGGCTTAGTGAAGCCTGGAGGGTCCCTGAAACTCTCCTGTGCAG

CCTCTGGATTCACTTTCAGTGACTATTACATGTATTGGGTTCGCCAGACTCCGGAAAAGAGGCT

GGAGTGGGTCGCAACCATTAGTGATGGTGGTACTTACACCTACTATCCAGACAGTGTGAAGGG

GCGATTCACCATCTCCAGAGACAATGCCAAGAACAACCTTTACCTGCAAATGAACAGTCTGAAG

TCTGAGGACACAGCCATGTATTACTGTGCAAGAGGATGGGTTTCTACTATGGTTAAACTTCTTTC

CTCCTTTCCTTACTGGGGCCAAGGGACTCTGGTCACTGTCTCTGCAGCCAAAACGACACCCCCA

TCTGTCTATCCACTGGCC
```

VH3.8 Amino Acid Sequence:
(SEQ ID NO: 36)
```
MDFGLSWVFLVLVLKGVQCEVQLVESGGGLVKPGGSLKLSCAASGFTFSDYYMYWVRQTPEKRLE

WVATISDGGTYTYYPDSVKGRFTISRDNAKNNLYLQMNSLKSEDTAMYYCARGWVSTMVKLLSSFP

YWGQGTLVTVSAAKTTPPSVYPLA
```

VL Sequencing Results:

VL1.1 DNA Sequence:
(SEQ ID NO: 50)
```
ATGGCCTGGATTTCTCTTATATTCTCTCCTGGCTCTCAGCTCAGGGGCCATTTCCCAGGCTGT

TGTGACTCAGGAATCTGCACTCACCACATCACCTGGTGAAACAGTCACACTCACTTGTCGCTCA

AGTACTGGGGCTGTTACAACTAGTAACTATGCCAACTGGGTCCAAGAAAAACCAGATCATTTATT

CACTGGTCTAGTAGGTGGTACCAACAACCGAGCTCCAGGTGTTCCTGCCAGATTCTCAGGCTCC
```

CTGATTGGAGACAAGGCTGCCCTCACCATCACAGGGGCACAGACTGAGGATGAGGCAATATAT

TTCTGTGCTCTATGGTACAGCAATTATTGGGTGTTCGGTGGAGGAACCAAACTGACTGTCCTAG

GCCAGCCCAAGTCTTCGCCATCAGTCACCCTGTTCCCACCCTCCACTGAAGAGCTAAGCTTGGG

VL1.1 Amino Acid Sequence:
(SEQ ID NO: 37)
MAWISLIFSLLALSSGAISQAVVTQESALTTSPGETVTLTCRSSTGAVTTSNYANWVQEKPDHLFTGL

VGGTNNRAPGVPARFSGSLIGDKAALTITGAQTEDEAIYFCALWYSNYWVFGGGTKLTVLGQPKSSP

SVTLFPPSTEELSL

VL1.2 DNA Sequence:
(SEQ ID NO: 51)
ATGGCCTGGACTTCACTCTTACTCTCTCTCCTGGCTCTCAGCTCAGGGGCCATTTCCCAGGCTG

TTGTGACTCAGGAATCTGCACTCACCACATCACCTGGTGAAACAGTCACACTCACTTGTCGCTC

AAGTACTGGGGCTGTTACAACTAGTAACTATGCCAACTGGGTCCAAGAAAAACCAGATCATTTAT

TCACTGGTCTAATAGGTGGTACCAACAACCGAGCTCCAGGTGTTCCTGCCAGATTCTCAGGCTC

CCTGATTGGAGACAAGGCTGCCCTCACCATCACAGGGGCACAGACTGAGGATGAGGCAATATA

TTTCTGTGCTCTATGGTACAGCAATTATTGGGTGTTCGGTGGAGGAACCAAACTGACTGTCCTA

GGCCAGCCCAAGTCTTCGCCATCAGTCACCCTGTGCCCGCCCTCCTCAGAGAAGCTAAGCTTG

GG

VL1.2 Amino Acid Sequence:
(SEQ ID NO: 39)
MAWTSLLLSLLALSSGAISQAVVTQESALTTSPGETVTLTCRSSTGAVTTSNYANWVQEKPDHLFTG

LIGGTNNRAPGVPARFSGSLIGDKAALTITGAQTEDEAIYFCALWYSNYWVFGGGTKLTVLGQPKSS

PSVTLCPPSSEKLSL

VL1.4 DNA Sequence:
(SEQ ID NO: 52)
ATGGCCTGGATTCCTCTTTTATTCTCTCTCCTGGCTCTCAGCTCAGGGGCCATTTCCCAGGCTGT

TGTGACTCAGGAATCTGCACTCACCACATCACCTGGTGAAACAGTCACACTCACTTGTCGCTCA

AGTACTGGGGCTGTTACAACTAGTAACTATGCCAACTGGGTCCAAGAAAAACCAGATCATTTATT

CACTGGTCTAATAGGTGGTACCAACAACCGAGCTCCAGGTGTTCCTGCCAGATTCTCAGGCTCC

CTGATTGGAGACAAGGCTGCCCTCACCATCATAGGGGCACAGACTGAGGATGAGGCAATATATT

TCTGTGCTCTATGGTACAGCAATTATTGGGTGTTCGGTGGAGGAACCAAACTGACTGTCCTAGG

CCAGCCCAAGTCTTCGCCATCAGTCACCCTGTTCCCGCCCTCCTTAGAAAAGCTTAGCTTGGG

VL1.4 Amino Acid Sequence:
(SEQ ID NO: 41)
MAWIPLLFSLLALSSGAISQAVVTQESALTTSPGETVTLTCRSSTGAVTTSNYANWVQEKPDHLFTGL

IGGTNNRAPGVPARFSGSLIGDKAALTIIGAQTEDEAIYFCALWYSNYWVFGGGTKLTVLGQPKSSPS

VTLFPPSLEKLSL

VL1.5 DNA Sequence:
(SEQ ID NO: 53)
ATGGCCTGGATTTCACTTTTACTCTCTCTCCTGGCTCTCAGCTCAGGGGCCATTTCCCAGGCTG

TTGTGACTCAGGAATCTGCACTCACCACATCACCTGGTGAAACAGTCACACTCACTTGTCGCTC

AAGTACTGGGGCTGTTACAACTAGTAACTATGCCAACTGGGTCCAAGAAAAACCAGATCATTTAT

TCACTGGTCTAATAGGTGGTACCAACAACCGAGCTCCAGGTGTTCCTGCCAGATTCTCAGGCTC

CCTGATTGGAGACAAGGCTGCCCTCACCATCACAGGGGCACAGACTGAGGATGAGGCAATATA

TTTCTGTGCTCTATGGTACAGCAATTATTGGGTGTTCGGTGGAGGAACCAAACTGACTGTCCTA

GGCCAGCCCAAGTCTTCGCCATCAGTCACCCTGTTTCCACCCTCCACAGAAGAGCTAAGCTTGG

G

VL1.5 Amino Acid Sequence:
(SEQ ID NO: 42)
MAWISLLLSLLALSSGAISQAVVTQESALTTSPGETVTLTCRSSTGAVTTSNYANWVQEKPDHLFTGL

IGGTNNRAPGVPARFSGSLIGDKAALTITGAQTEDEAIYFCALWYSNYWVFGGGTKLTVLGQPKSSP

SVTLFPPSTEELSL

VL1.6 DNA Sequence:
(SEQ ID NO: 54)
ATGGCCTGGATTTCACTTATCTTCTCTCTCCTGGCTCTCAGCTCAGGGGCCATTTCCCAGGCTG

TTGTGACTCAGGAATCTGCACTCACCACATCACCTGGTGAAACAGTCACACTCACTTGTCGCTC

AAGTACTGGGGCTGTTACAACTAGTAACTATGCCAACTGGGTCCAAGAAAAACCAGATCATTTAT

TCACTGGTCTAATAGGTGGTACCAGCAACCGAGCTCCAGGTGTTCCTGCCAGATTCTCAGGCTC

CCTGATTGGAGACAAGGCTGCCCTCACCATCACAGGGGCACAGACTGAGGATGAGGCAATATA

TTTCTGTGCTCTATGGTACAGCAATTATTGGGTGTTCGGTGGAGGAACCAAACTGACTGTCCTA

GGCCAGCCCAAGTCTTCGCCATCAGTCACCCTGTACCCGCCCTCTACAAAGGAGCTTAGCTTG

GG

VL1.6 Amino Acid Sequence:
(SEQ ID NO: 38)
MAWISLIFSLLALSSGAISQAVVTQESALTTSPGETVTLTCRSSTGAVTTSNYANWVQEKPDHLFTGLI

GGTSNRAPGVPARFSGSLIGDKAALTITGAQTEDEAIYFCALWYSNYWVFGGGTKLTVLGQPKSSPS

VTLYPPSTKELSL

VL1.7 DNA Sequence:
(SEQ ID NO: 55)
ATGGCCTGGACTTCTCTCTTATTCTCTCTCCTGGCTCTCAGCTCAGGGGCCATTTCCCAGGCTG

TTGTGACTCAGGAATCTGCACTCACCACATCACCTGGTGAAACAGTCACACTCACTTGTCGCTC

AAGTACTGGGGCTGTTACAACTAGTAACTATGCCAACTGGGTCCAAGAAAAACCAGATCATTTAT

TCACTGGTCTAATAGGTGGTACCAACAACCGAGCTCCAGGTGCTCCTGCCAGATTCTCAGGCTC

CCTGATTGGAGACAAGGCTGCCCTCACCATCACAGGGGCACAGACTGAGGATGAGGCAATATA

TTTCTGTGCTCTATGGTACAGCAATTATTGGGTGTTCGGTGGAGGAACCAAACTGACTGTCCTA

GGCCAGCCCAAGTCTTCGCCATCAGTCACCCTGTGCCCGCCCTCTACAGAAAAGCTAAGCTTG

GG

VL1.7 Amino Acid Sequence:
(SEQ ID NO: 40)
MAWTSLLFSLLALSSGAISQAVVTQESALTTSPGETVTLTCRSSTGAVTTSNYANWVQEKPDHLFTG

LIGGTNNRAPGAPARFSGSLIGDKAALTITGAQTEDEAIYFCALWYSNYWVFGGGTKLTVLGQPKSS

PSVTLCPPSTEKLSL

Example 7—InflaMab Design—Development of a Bi-Specific Antibody Against Both of IL-1R1 and NLRP3

The variable domain sequences of the monoclonal antibodies IL-1R1 and NLRP3 were sequenced.

The antibody was constructed using the IL-1R1 antibody with an IgG2a mouse constant domain sequence. A short linker was added to the C-terminal end of the heavy chain and the NLPR3 variable domains in an ScFv format with the linker (GGGGS)₃ was attached to create the bispecific. The DNA and amino acid sequences can be found below.

The constructs were cloned into ATUM vector pD2610-v5 and verified by sequencing. FIG. 31 illustrates the bispecific design and the plasmid map of InflaMab.

Designed Bispecific Antibody Sequences

Light Chain DNA Sequence:
(SEQ ID NO: 56)
ATGGTCAGCTCTGCTCAATTTCTCGGACTCCTTCTTCTGTGCTTTCAAGGAACACGCTGCGATAT

TGTGATGACCCAGTCCCCCGCCACCCTGTCCGTGACTCCGGGCGACCGGGTGTCCCTGTCGTG

CCGGGCATCACAGAGCATCTCCGACTACCTGTCGTGGTACCAGCAGAGATCACACGAGAGCCC

-continued

```
TCGCCTGATCATCAAATACGCCAGCCAGTCAATCTCCGGCATCCCCTCGCGGTTCTCCGGGTCC

GGTTCCGGCTCCGACTTCACACTGTCCATTAACTCCGTGGAACCTGAGGACGTGGGAGTGTACT

ACTGTCAACACGGCCATTCGTTCCCGCTGACTTTCGGGTCGGGAACCAAGCTGGAATTGAAGA

GGGCGGACGCGGCCCCTACCGTGTCAATTTTCCCACCGAGCTCCGAACAGCTCACCAGCGGC

GGTGCCTCGGTCGTGTGCTTCCTCAACAACTTCTATCCAAAAGACATTAACGTCAAGTGGAAGA

TCGATGGATCGGAGAGACAGAACGGAGTGCTGAACAGCTGGACTGATCAGGACTCCAAGGATT

CGACCTACTCCATGAGCTCCACTCTGACCCTGACCAAGGACGAATACGAGCGGCACAATTCCTA

CACTTGCGAAGCCACCCACAAGACCTCAACGTCCCCCATCGTGAAGTCCTTCAACCGCAACGA

GTGTTGATAA
```

Light Chain Amino Acid Sequence:
(SEQ ID NO: 57)

```
MVSSAQFLGLLLLCFQGTRCDIVMTQSPATLSVTPGDRVSLSCRASQSISDYLSWYQQRSHESPRLII

KYASQSISGIPSRFSGSGSGSDFTLSINSVEPEDVGVYYCQHGHSFPLTFGSGTKLELKRADAAPTV

SIFPPSSEQLTSGGASVVCFLNNFYPKDINVKWKIDGSERQNGVLNSWTDQDSKDSTYSMSSTLTLT

KDEYERHNSYTCEATHKTSTSPIVKSFNRNEC**
```

Heavy Chain DNA Sequence:
(SEQ ID NO: 58)

```
ATGGGCTGGACCCTCGTGTTCCTGTTCCTGCTGAGCGTGACGGCGGGCGTGCACTCCCAAATC

CAGCTTGTGCAGTCCGGACCCGAGCTCAGGAAGCCGGGCGAAACTGTGCGCATCAGCTGCAA

GGCTTCAGGGTACCCTTTCACCACCGCCGGGCTGCAATGGGTGCAGAAGATGTCCGGGAAGG

GTCTGAAGTGGATCGGATGGATGAACACCCAGTCCGAAGTGCCTAAATACGCCGAAGAATTCAA

GGGCCGCATTGCGTTCAGCCTGGAGACAGCCGCCTCGACCGCGTACCTTCAGATCAACAATCT

CAAGACTGAGGACACTGCCACCTACTTCTGTGCCAAGAGCGTGTACTTCAACTGGAGATACTTC

GACGTGTGGGGCGCCGGAACCACCGTGACCGTGTCCAGCGCCAAGACTACCGCCCCGAGCGT

GTACCCTCTGGCGCCAGTGTGCGGCGACACGACTGGCAGCTCGGTGACCTTGGGCTGCCTCG

TGAAGGGTTACTTCCCCGAGCCCGTGACTCTGACTTGGAACTCGGGCTCACTGTCGTCCGGAG

TGCATACCTTCCCGGCTGTGCTGCAAAGCGACCTCTATACCTTGTCATCGTCCGTGACTGTGAC

CTCCTCCACCTGGCCGTCCCAGAGCATCACCTGTAATGTCGCCCACCCTGCTTCATCGACTAAG

GTCGACAAGAAGATCGAGCCCAGAGGACCTACCATCAAGCCCTGCCCGCCCTGCAAATGCCCG

GCCCCAAACTTGCTGGGAGGGCCTTCCGTGTTCATCTTCCCTCCGAAAATCAAGGACGTGCTGA

TGATCTCCCTGAGCCCAATTGTCACTTGCGTGGTGGTGGATGTGTCCGAAGATGACCCAGATGT

GCAGATTTCATGGTTCGTGAACAACGTCGAAGTCCATACCGCACAGACCCAGACCCACCGCGA

GGATTACAACTCGACGCTGCGCGTCGTCAGCGCCCTGCCGATTCAGCACCAGGATTGGATGAG

CGGAAAGGAATTCAAGTGCAAAGTCAACAACAAGGACCTTCCGGCGCCGATCGAACGGACCAT

CTCGAAGCCTAAGGGATCAGTGCGGGCGCCTCAGGTCTACGTGCTCCCGCCTCCGGAAGAGG

AAATGACCAAGAAACAAGTCACCCTGACTTGCATGGTCACCGACTTCATGCCTGAGGACATCTA

TGTGGAGTGGACTAACAACGGAAAGACTGAACTGAACTACAAAAACACCGAACCAGTGCTGGAC

TCTGACGGCTCCTACTTCATGTACTCGAAGCTGCGGGTGGAGAAGAAAAACTGGGTGGAACGA

AACTCCTACTCGTGTTCCGTGGTGCACGAGGGTCTGCACAACCACCATACCACCAAGTCCTTCT
```

```
-continued
CCCGGACCCCCGGAAAGGGATCCGCCGGGGGATCCGGAGGGGACTCCGAAGTGCAACTGGT

GGAGTCGGGTGGCGGACTCGTGAAGCCCGGGGGGTCATTGAAGCTTTCCTGTGCTGCCTCCG

GTTTCACTTTCTCCGACTATTACATGTACTGGGTCAGACAGACCCCGGAGAAGCGGCTCGAATG

GGTGGCCACCATTTCGGACGGTGGAACCTACACTTACTACCCTGACTCCGTCAAGGGCCGGTT

TACTATCTCCCGCGACAACGCGAAGAACAATCTGTACCTCCAAATGAACTCCCTGAAGTCCGAG

GACACCGCCATGTACTATTGCGCAAGGGGATGGGTCAGCACTATGGTCAAGCTGCTGTCATCCT

TCCCTTACTGGGGACAGGGAACCCTTGTGACTGTGTCAGCCGGTGGCGGGGGGTCGGGCGGC

GGCGGTTCCGGTGGAGGGGGATCCCAGGCCGTCGTGACCCAAGAGTCGGCTCTGACTACTTC

ACCCGGAGAAACCGTGACCCTGACATGCCGCTCCTCCACTGGCGCAGTGACCACGAGCAATTA

CGCCAACTGGGTGCAGGAAAAGCCCGATCACCTGTTCACTGGACTCATTGGGGGAACCAACAA

CCGGGCGCCGGGCGTGCCCGCTCGGTTTAGCGGCTCCCTGATTGGAGACAAGGCCGCCCTGA

CTATCACCGGAGCCCAGACCGAAGATGAAGCCATCTACTTTTGCGCACTCTGGTACTCTAACTA

CTGGGTGTTTGGCGGCGGAACCAAGCTGACTGTGCTCGGACAGCCGAAGTGATAAAA
Heavy Chain Amino Acid Sequence:
                                                      (SEQ ID NO: 59)
MGWTLVFLFLLSVTAGVHSQIQLVQSGPELRKPGETVRISCKASGYPFTTAGLQWVQKMSGKGLKW

IGWMNTQSEVPKYAEEFKGRIAFSLETAASTAYLQINNLKTEDTATYFCAKSVYFNWRYFDVWGAGT

TVTVSSAKTTAPSVYPLAPVCGDTTGSSVTLGCLVKGYFPEPVTLTWNSGSLSSGVHTFPAVLQSDL

YTLSSSVTVTSSTWPSQSITCNVAHPASSTKVDKKIEPRGPTIKPCPPCKCPAPNLLGGPSVFIFPPKI

KDVLMISLSPIVTCVVVDVSEDDPDVQISWFVNNVEVHTAQTQTHREDYNSTLRVVSALPIQHQDWM

SGKEFKCKVNNKDLPAPIERTISKPKGSVRAPQVYVLPPPEEEMTKKQVTLTCMVTDFMPEDIYVEW

TNNGKTELNYKNTEPVLDSDGSYFMYSKLRVEKKNWVERNSYSCSVVHEGLHNHHTTKSFSRTPG

KGSAGGSGGDSEVQLVESGGGLVKPGGSLKLSCAASGFTFSDYYMYWVRQTPEKRLEWVATISDG

GTYTYYPDSVKGRFTISRDNAKNNLYLQMNSLKSEDTAMYYCARGVVVSTMVKLLSSFPYWGQGTL

VTVSAGGGGSGGGGSGGGGSQAVVTQESALTTSPGETVTLTCRSSTGAVTTSNYANWVQEKPDH

LFTGLIGGTNNRAPGVPARFSGSLIGDKAALTITGAQTEDEAIYFCALWYSNYWVFGGGTKLTVLGQ

PK**
```

Example 8—InflaMab (Bispecific Against IL-1R1 and NLRP3) Transient Expression The aim was to carry out transient transfections of InflaMab vector DNA in ExpiCHO cells. Following culture, expressed InflaMab was purified from the culture supernatant and QC analysis carried out on the purified protein.

InflaMab is a 210 kiloDalton (kDa) bispecific mouse antibody composed of two pairs of light chain and two pairs of heavy chains with ScFv domains fused to the N-terminal, complexed together via disulphide bonds. A mammalian expression vector encoding InflaMab was transfected into ExpiCHO cells. The expressed antibody was subsequently purified from clarified culture supernatant via protein A affinity chromatography. The concentration of purified antibody was measured using a NanoDrop Lite, Thermofisher and purity was evaluated using SDS-PAGE.

Sequence

DNA coding for the amino acid sequences of InflaMab was synthesised and cloned into the mammalian transient expression plasmid pD2610-v5 (Atum).

Plasmid InflaMab:

```
Plasmid InflaMab:
>InflaMab Light chain (Theoretical MW = 26.7 kDa)
                                           (SEQ ID NO: 57)
MVSSAQFLGLLLLCFQGTRCDIVMTQSPATLSVTPGDRVSLSCRASQSI

SDYLSWYQQRSHESPRLIIKYASQSISGIPSRFSGSGSGSDFTLSINSV

EPEDVGVYYCQHGHSFPLTFGSGTKLELKRADAAPTVSIFPPSSEQLTS

GGASVVCFLNNFYPKDINVKWKIDGSERQNGVLNSWTDQDSKDSTYSMS

STLTLTKDEYERHNSYTCEATHKTSTSPIVKSFNRNEC

>InflaMab Heavy Chain (Theoretical MW = 79.3 kDa)
                                           (SEQ ID NO: 59)
MGWTLVFLFLLSVTAGVHSQIQLVQSGPELRKPGETVRISCKASGYPFT

TAGLQWVQKMSGKGLKWIGWMNTQSEVPKYAEEFKGRIAFSLETAASTA

YLQINNLKTEDTATYFCAKSVYFNWRYFDVWGAGTTVTVSSAKTTAPSV

YPLAPVCGDTTGSSVTLGCLVKGYFPEPVTLTWNSGSLSSGVHTFPAVL

QSDLYTLSSSVTVTSSTWPSQSITCNVAHPASSTKVDKKIEPRGPTIKP
```

-continued

CPPCKCPAPNLLGGPSVFIFPPPKIKDVLMISLSPIVTCVVVDVSEDDPD

VQISWFVNNVEVHTAQTQTHREDYNSTLRVVSALPIQHQDWMSGKEFKC

KVNNKDLPAPIERTISKPKGSVRAPQVYVLPPPEEEMTKKQVTLTCMVT

DFMPEDIYVEWTNNGKTELNYKNTEPVLDSDGSYFMYSKLRVEKKNWVE

RNSYSCSVVHEGLHNHHTTKSFSRTPGKGSAGGSGGDSEVQLVESGGGL

VKPGGSLKLSCAASGFTFSDYYMYWVRQTPEKRLEWVATISDGGTYTYY

PDSVKGRFTISRDNAKNNLYLQMNSLKSEDTAMYYCARGWVSTMVKLLS

SFPYWGQGTLVTVSAGGGGSGGGGSGGGGSQAVVTQESALTTSPGETVT

LTCRSSTGAVTTSNYANWVQEKPDHLFTGLIGGTNNRAPGVPARFSGSL

IGDKAALTITGAQTEDEAIYFCALWYSNYWVFGGGTKLTVLGQPK

Transient Transfection of CHO Cells

Suspension adapted ExpiCHO cells (Thermo Fisher, UK) were routinely cultured at $1.0$-$3.0 \times 10^5$ cells/ml every 2-3 days in 500 ml vented Erlenmeyer flasks (Corning, Netherlands) agitated at 135 rpm at 37° C. 8% $CO_2$. Plasmid DNA for transfection was isolated using a Purelink Hipure plasmid filter maxiprep kit (Thermo Fisher, UK) as per the manufacturer instructions. DNA was quantified using a Nano Drop lite spectrophotometer as per the manufacturer instructions.

Twenty-four hours prior to transfection, ExpiCHO cells were seeded at a concentration of $4.0 \times 10^6$ cells/ml in ExpiCHO expression medium and grown overnight at 135 rpm, 37° C. 8% $CO_2$. On the day of transfection, 250 ml ExpiCHO cells were diluted to a final density of $6.0 \times 10^6$ cells/ml in ExpiCHO expression medium. 1.0 µg/ml of plasmid DNA and 0.32% (v/v) Expifectamine CHO reagent (Thermo Fisher) were diluted separately in 4% (v/v) OptiPro SFM (Thermo Fisher). The Expifectamine CHO/Optipro complex was added to the Plasmid DNA/Optipro complex dropwise. The transfection mixture was immediately added to the ExpiCHO cells. Transfected cells were incubated overnight at 135 rpm, 37° C., 8% $CO_2$.

Twenty hours post transfection, cultures were supplemented with 0.6% (v/v) Expi CHO enhancer (Thermo Fisher, UK) and 24% ExpiCHO feed (Thermo Fisher, UK). The viability of the cells were closely monitored and cultures were harvested on day 8 by centrifugation at 4000 rpm for 40 minutes at room temperature.

Purification of InflaMab

Purifications were performed using AKTA (GE Healthcare) chromatography equipment. Prior to use, all AKTA equipment was thoroughly sanitized using 1M NaOH. Following centrifugation, filtered (0.22 µm) cell culture supernatant was applied to an AKTA system fitted with a 1 ml HiTrap Protein A column (equilibrated with wash buffer). Following loading, the column was washed with 20 column volumes of wash buffer. Bound antibody was step eluted with 10 column volumes of elution buffer. All eluted fractions were neutralised with Tris pH 9.0 buffer. Eluted fractions corresponding to elution peak were selected for overnight dialysis into PBS. The purity of the antibody was >95%, as judged by SDS-polyacrylamide midi gels.

SDS-PAGE analysis—see FIG. 32

Sodium Dodecyl Sulphate Polyacrylamide Electrophoresis (SDS PAGE) was carried out on purified antibody using standard methods.

Molecular weight marker shown in kilodaltons. Lanes, in FIG. 32, are as follows:

| Lane Number | Sample | Batch | Amount (µg) | Conditions |
|---|---|---|---|---|
| 1 | PageRuler Plus (Thermo Fisher) | NA | NA | Reducing |
| 2 | InflaMab | 1 | 5 | Reducing |
| 3 | Blank | NA | NA | Reducing |
| 4 | InflaMab | 1 | 5 | Non-reducing |

InflaMab is ≥95% pure as judged by analysis of SDS-polyacrylamide gels. Under reducing conditions, both heavy and the light chains of the antibody are visible and are observed at the expected molecular weight of approximately 80 and 27 kDa, respectively. Under non-reducing conditions, a single major band and several minor bands are observed. The additional bands (impurities) are likely the result of non-glycosylated IgG and IgG degradation products (e.g. a single [partial] light chain, a combination of two heavy and one light chain, two heavy chains, two heavy and one light chain).

Evaluation of Purified InflaMab

Purified InflaMab was quantified using a Nanodrop Lite spectrophotometer and the extinction coefficient 330,685 $M^{-1}$ $cm^{-1}$ (or 1.0 mg/ml=A280 of 1.7 [assuming a MW=184,276 Da]), as per the manufacturer instructions. A total of 17.5 mg of InflaMab was purified from 0.3 litres of transfected cell culture supernatant.

TABLE 3

Concentration and yield of Antibody InflaMab from a 250 ml transfection.

| Sample | Batch | Vol. of culture Super. (L) | Concentration (mg/ml) | Volume (ml) | Total (mg) | Yield (mg/L) | Endotoxin (EU/mg) |
|---|---|---|---|---|---|---|---|
| InflaMab | 1 | 0.3 | 3.15 | 5.57 | 17.55 | 58.49 | ND |

Summary: InflaMab
Material: Purified Antibody
Origin: Produced in a Chinese Hamster (*Cricetulus griseus*) Ovary cell line (no hamster or animal component added)

| Results | |
|---|---|
| Purity: | ≥95% pure (as determined by SDS-polyacrylamide gels [FIG. 1]) |
| Endotoxin (EU/mg): | Not determined |
| Concentration (mg/ml): | 3.15 (as determined by measurement of absorbance at 280 nm) |
| Mycoplasma: | Not determined |
| Package contents and storage recommendations | |
| Volume (ml): | 5.57 |
| Total (mg): | 17.55 |
| Container: | 2 ml tube × 3 |
| Volume per container: | 2.0 ml × 2; 1.57 ml × 1 |

| Net weight: | Not determined |
| --- | --- |
| Formulation: | Provided as a 0.2 μm sterile-filtered solution in PBS. |
| Shipped: | Ice packs (+4° C.) |
| Storage: | 4° C. refrigerated |

Non-hazardous, non-infectious. For research use only.

Figure 33A:
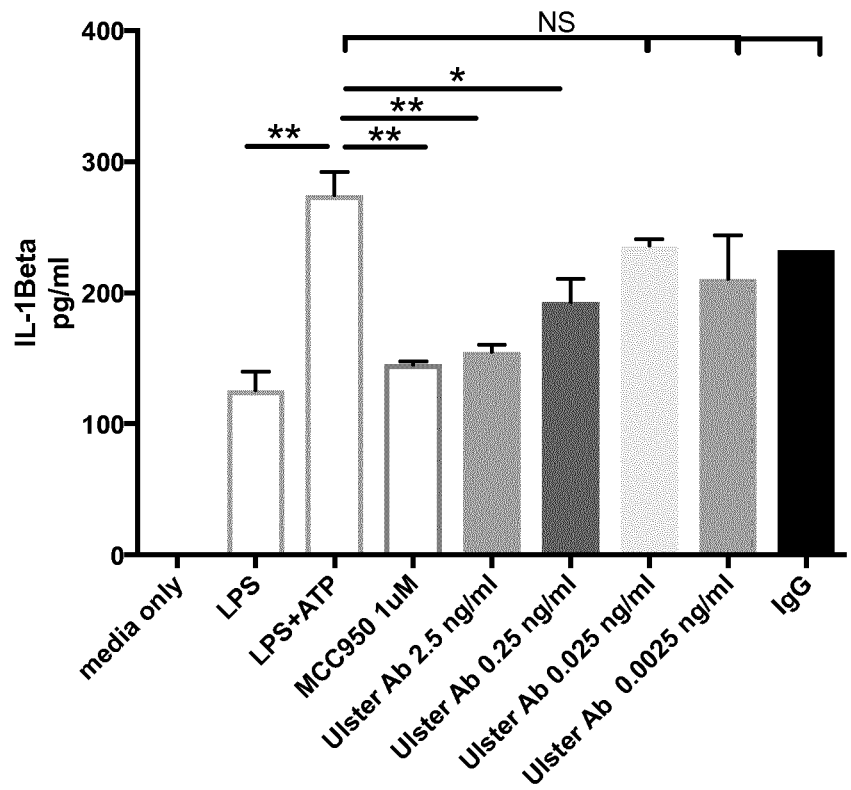
Figure 33B:
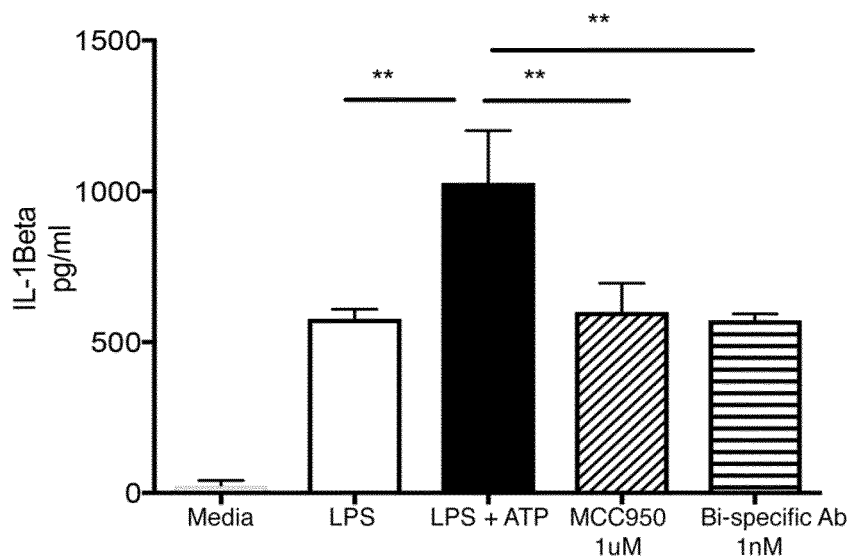

Inflamab prevents IL-1β release—see FIGS. 33a and b. THP1 cells, for FIGS. 33a and b, were cultured in 96-well plates at 100,000 cells/200 μl complete media. PMA (100 μg/ml for 72 hours) was used to differentiate THP-1 cells into macrophages. Following 24 hours of rest, differentiated THP1 cells were stimulated with LPS (1 μg/ml) for 3 hours, treated with MCC950 (1 μM) or the IL-1R1/NLRP3 Ab in a dose dependent fashion from 0.0025 ng/ml to 2.5 ng/ml for FIG. 33a or with IL-1R1/NLRP3 Ab (1 nM) for FIG. 33b or with IgG control antibody for 30 minutes, followed by ATP (5 mM) for 1 hour. IL-1β release was measured in the supernatant by ELISA.

Inflamab prevents caspase-1 activation in THP1 cells—see FIG. 34. THP1 cells, for FIG. 34, were cultured in 96-well plates at 100,000cells/200 ul complete media. PMA (100 ug/ml for 72 hours) was used to differentiated THP-1 cells into macrophages. Following 24 hours of rest, differentiated THP1 cells were stimulated with LPS (1 ug/ml) for 3 hours, treated with the IL-1R1/NLRP3 Ab (1 μg/ml) for 30 minutes, followed by ATP (5 mM) for 1 hour. Caspase-1 activation was assessed by staining cells with a non-cytotoxic Fluorescent Labelled Inhibitor of Caspase-1 (FAM-FLICA) and DAPI (nuclear stain). Cells were treated with LPS alone (negative control), LPS+ATP (positive control), mouse IgG2a (1 ug/ml, Ab control), or IL-1r/NLRP3 bi-specific Ab (1 ug/ml, experimental). Representative confocal images are shown for each group. Green=active caspae-1 and blue=Dapi/nuclear stain.

Internalization of Inflamab—see FIG. 35. THP1 cells, for FIG. 35, were cultured in 96-well plates at 100,000cells/200 ul complete media. Differentiation of THP1 cells was induced by PMA (100 ug/ml for 72 hours). Following 24 hours of rest, differentiated THP1 cells were stimulated with LPS (1 ug/ml) for 3 hours, treated with a pHrodo red labelled IL-1r/NLRP3 Ab (1 ug/ml) for 30 minutes, followed by ATP (5 mM) for 1 hour. The internalization of the Ab was tracked using a pHrodo red labelled bi-specific Ab that only fluoresces when internalized. (A) A representative confocal image shows the internalization of the pHrodo red labelled bi-specific Ab in a differentiated THP1 cell. (B) A representative confocal image shows significant reduction of caspase-1 activation (green) in THP1 cells that have internalized the bi-specific Ab (red, white arrow) as compared to THP1 cells that did not internalize the Ab (green only).

Example 9—InflaMab for Atherosclerosis/Coronary Artery Disease

Materials and Methods

BMDM In Vitro Culture

Bone marrow cells were isolated from the tibias and femurs of C57BL/6 mice. To obtain bone marrow-derived dendritic cells (BMDCs), cells were cultured for 7 days at 37° C. and 5% $CO_2$ in Iscove's modified Dulbecco's medium (IMDM) supplemented with 8% fetal calf serum (FCS), 1% penicillin/streptomycin (GE Healthcare Life Sciences, Marlborough, MA, USA), 1% glutamax (Thermo Fisher Scientific, Waltham, MA, USA) and 20 μM β-mercaptoethanol (Sigma-Aldrich, St. Louis, MO, USA) in the presence of 20 ng/mL gm-CSF (Preprotech, Rocky Hill, NJ, USA). To obtain bone marrow-derived macrophages (BMDMs), cells were cultured for 7 days in Roswell Park Memorial Institute medium (RPMI) supplemented with 10% FCS, 100 U/mL penicillin/streptomycin, 0.1 mM nonessential amino acids, 1% pyruvate and 2 mM L-glutamine (Thermo Fisher Scientific) in the presence of 20 ng/mL m-CSF (eBioscience)

Inflammasome Activation Assay

For in vitro stimulation, $0.1 \times 10^6$ cells per well were added to 96-well flat-bottom plates (Greiner Bio-One, Kremsmünster, Austria). Cells were first primed with LPS (50 ng/mL) for 2 hours, after which cholesterol crystals (2 mg/mL) were added in the presence or absence of MCC950 (1 μM, Adipogen, San Diego, US) for an additional 4 hours. The supernatant was used for analysis of cytokine production by enzyme-linked immunosorbent assay (ELISA) according to the manufacturer's protocol.

In Vivo LPS Challenge

Female apoE-/- mice were fed a Western-type diet containing 0.25% cholesterol and 15% cacao butter (SDS, Sussex, UK) starting 1 week prior to treatment and throughout the experiment. Diet and water were provided ad libitum. After 1 week of diet feeding, mice were injected intraperitoneally with PBS or InflaMab (100 μg or 200 μg) administrated on day 10 and day 14. After 2 weeks of diet and a 1-week treatment mice were challenged intravenously with LPS (50 μg/kg, *Salmonella minnesota* R595, List Biological Laboratories Inc.) and blood was collected after 0.5, 1, 2 and 4 hours. After 4 hours mice were sacrificed and serum levels of IL-1β and TNF-α were measured by ELISA.

Atherosclerosis

Female apoE-/- mice were fed a Western-type diet, containing 0.25% cholesterol and 15% cacao butter (SDS, Sussex, UK) starting two weeks prior to surgery and throughout the experiment. After 2 weeks of diet feeding, carotid artery plaque formation was induced by perivascular collar placement in these mice as described previously (von der Thusen et al, Circulation. 2001; 103(8):1164-1170). During 4 weeks of lesion development, mice were injected 3 times per week with either PBS (control) or InflaMab (100 μg). Through the experiment, mice were weighed weekly and blood samples were obtained via the tail vein. Total cholesterol levels were determined in the serum using enzymatic colorimetric procedures (Roche/Hitachi, Mannheim, Germany). Precipath (Roche/Hitachi) was used as an internal standard. Fasting glucose levels were determined in mice at 2 weeks after starting the treatment with InflaMab and were measured with an Accu-Check glucometer (Roche Diagnostics, Almere, The Netherlands). For lipid profiling, serum samples pooled from 3 mice were used (n=3 samples per group) which were diluted 6 times, and fractionation of plasma lipoproteins was performed using an AKTA-FPLC. In each fraction, the total cholesterol levels were determined by incubation with cholesterol CHOD-PAP Reagent (Roche, Woerden, The Netherlands). Absorbance was measured at 492 nm.

After 4 weeks of treatment, the mice were anesthetized and in situ perfused, after which the carotid arteries were collected, frozen in OCT compound (TissueTek; Sakura Finetek, The Netherlands) and stored at −80° C. Transverse 10 μm cryosections were prepared on a Leica CM 3050S Cryostat (Leica Instruments) in a proximal direction for (immuno)histochemical analysis.

Histology and Morphometry

Cryosections were routinely stained with hematoxylin (Sigma-Aldrich, Zwijndrecht, The Netherlands) and eosin (Merck Diagnostica, Darmstadt, Germany). Morphometric analysis (Leica Qwin image analysis software) was performed on hematoxylin-eosin stained sections of the carotid arteries. For each carotid, lesion size was quantified every 100 µm, from the first appearance of the lesion proximal to the collar up to complete disappearance of the lesion from the artery. The number of sections analyzed ranged from 5 to 15 sections per mouse, from which average plaque size and plaque volume were calculated. The section with the largest plaque size was annotated as the plaque with maximum stenosis. For the quantification of lesion content in the carotid artery, four consecutive cross-sections containing the largest lesions were used. To determine lipid content, sections were stained with Oil-Red-O (Sigma-Aldrich). Macrophage content of the lesions was assessed using a rat monoclonal MOMA-2 antibody (Serotec, Kidlington, Oxford, UK). Collagen was visualized using a Sirius Red staining (Sigma-Aldrich). Mast cells and neutrophils were visualized by staining of cryosections with naphthol AS-D chloroacetate esterase (Sigma-Aldrich). The number of mast cells and neutrophils was assessed manually in two consecutive cross-sections containing the largest lesions. MOMA-2 and collagen positive areas were quantified by Leica Qwin image analysis software using a Leica DM-RE microscope (Leica Microsystems Inc., Wetzlar, Germany). All morphometric analyses were performed by a blinded operator (T.v.d.H.).

Flow Cytometry

At sacrifice, blood and spleen were isolated and single-cell suspensions were obtained by mashing the organs through a 70 µm cell strainer. Red blood cells were removed from blood and splenocyte suspensions using ACK lysis buffer (0.15 M NH4Cl, 1 mM KHCO3, 0.1 mM Na2EDTA, pH 7.3). The immune cell populations were analyzed using flow cytometry with the relevant antibodies (Table 4). Cells were incubated with antibodies against the indicated markers and fixable viability dye 780 for live/dead cell determination. All antibodies were purchased from eBioscience and BD Biosciences. Flow cytometry analysis was performed on an FACSCanto II (Beckton Dickinson, Mountain View, CA), and the acquired data were analyzed using FlowJo software.

TABLE 4

Antibodies used for flow cytometry.

| Antibody | Clone | Company |
|---|---|---|
| CD11b | M1/70 | eBioscience |
| Ly6G | 1A8 | BD Biosciences |
| NK1.1 | PK136 | eBioscience |
| CD4 | GK1.5 | eBioscience |
| CD8a | 53-6.7 | BD Biosciences |

Results

In this study, InflaMab was demonstrated to specifically and dose-dependently inhibit IL-1beta secretion from murine bone marrow derived macrophages. Specificity was confirmed by observing no effect the secretion of TNFalpha in these same cells (see FIG. 36). InflaMab was also demonstrated to specifically inhibit IL-1beta secretion in vivo as demonstrated in apoe−/− mice. Specificity was confirmed by observing no effect the secretion of TNFalpha in these mice (see FIG. 37).

InflaMab was further demonstrated to have disease modifying effects in atherosclerosis/coronary artery disease. InflaMab wa found to inhibit the size of plaque development in vivo in an apoe−/− mouse model of atherosclerosis. In this study, cross-sections of the carotid plaques were made every 80 µm, from start of the plaque until the end. The size each of these plaques was measured in square µm, and the biggest lesion from each plaque (maximum stenosis), but also the average the size of these plaques throughout the carotids (average plaque size), was plotted (see FIG. 38). FIG. 38a demonstrates a trend towards a reduction in lesion size, FIG. 38 demonstrates a significant reduction in lesion size (−35%).

Tables 5 and 6 below include columns showing media size (which is the size of the medial smooth muscle layer) on which no effect is demonstrated, as expected. Lumen size is the area of the artery that is still open for blood flow, which is almost significantly larger in the InflammAb (InflaMab) group compared to the Control IgG. This makes sense since the plaques are smaller in the InflammAb group (see "Plaque" column). Total vessel area is area of the plaque+media+lumen, thus total vessel surface, which is not different between the InflammAb group and the Control IgG. From this we can conclude that there is no outward remodelling of the arteries, which is a positive finding.

TABLE 5

Comparison of plaque size at site of maximal stenosis (µm$^2$) in mice treated with Control IgG or InflammAb (InflaMab).

| mouse nr | Plaque | Media | Lumen size | total vessel area |
|---|---|---|---|---|
| Plaque size at site of maximal stenosis (um2) Control IgG | | | | |
| 1 | 120600 | 21755 | 121 | 142476 |
| 3 | 81859 | 46628 | 8294 | 136781 |
| 5 | 56207 | 42972 | 8103 | 107282 |
| 7 | 44950 | 39593 | 1058 | 85601 |
| 9 | 102500 | 55718 | 412 | 158629 |
| 11 | 66908 | 24314 | 9471 | 100693 |
| 13 | 146100 | 50968 | 1774 | 198842 |
| 17 | 23530 | 23144 | 778 | 47453 |
| 19 | 142900 | 44059 | 286 | 187245 |
| 21 | 61847 | 35578 | 186 | 97611 |
| 23 | 51154 | 30045 | 205 | 81404 |
| 25 | 84771 | 38873 | 20928 | 144572 |
| 27 | 119900 | 40254 | 0 | 160154 |
| Average | 84863 | 37992 | 3971 | 126826 |
| Stdev | 38845 | 10675 | 6208 | 44346 |
| SEM | 10774 | 2961 | 1722 | 12300 |
| InflammAb | | | | |
| 2 | 60234 | 37642 | 22733 | 120609 |
| 4 | 79486 | 36514 | 7574 | 123574 |
| 6 | 70095 | 33475 | 10940 | 114510 |
| 10 | 68309 | 54740 | 68 | 123117 |
| 12 | 57655 | 39339 | 3680 | 100673 |
| 14 | 21550 | 40801 | 18730 | 81080 |
| 16 | 84293 | 51894 | 4343 | 140531 |
| 18 | 82227 | 29970 | 8934 | 121131 |
| 20 | 42772 | 42355 | 476 | 85602 |
| 24 | 22193 | 43241 | 36674 | 102108 |
| Average | 58881 | 40997 | 11415 | 111293 |
| Stdev | 23172 | 7651 | 11542 | 18587 |
| SEM | 6987 | 2307 | 3480 | 5604 |
| t-test | 0.076 | 0.460 | 0.060 | 0.312 |
| % reduction | 30.6164 | | | |

TABLE 6

Comparison of average plaque
size (μm²) in mice treated with
Control IgG or InflammAb (InflaMab).

| mouse nr | Plaque |
|---|---|
| Average plaque size (um2) Control | |
| 1 | 94711 |
| 3 | 55661 |
| 5 | 31412 |
| 7 | 33759 |
| 9 | 64496 |
| 11 | 46211 |
| 13 | 118451 |
| 17 | 19165 |
| 19 | 92566 |
| 21 | 37824 |
| 23 | 40854 |
| 25 | 50849 |
| 27 | 79193 |
| Average | 58858 |
| Stdev | 29408 |
| SEM | 8156 |
| InflammAb | |
| 2 | 30602 |
| 4 | 54443 |
| 6 | 44635 |
| 10 | 46974 |
| 12 | 31493 |
| 14 | 15836 |
| 16 | 41036 |
| 18 | 61429 |
| 20 | 25617 |
| 24 | 13977 |
| Average | 36604 |
| Stdev | 15820 |
| SEM | 4770 |
| t-test | 0.043 |

The hearts of these mice are sectioned for aortic root plaque analysis, and histology, e.g. macrophage content, examined. At the sacrifice, flow cytometric analysis is carried out on blood, spleen and peritoneal cells for monocyte subsets. Other measurements are carried out including plasma cholesterol levels. Mouse weight and general white blood cell levels (hematology analysis) was measured and no difference between the InflaMab and control groups was found.

In summary, these results provide evidence to support the use of InflaMab to prevent/treat atherosclerosis/coronary artery disease. Indeed, these data suggest that InflaMab may also reduce the risk of plaque rupture preventing acute coronary syndromes and/or myocardial infarction.

The NLRP3 inflammasome has long been implicated in atherosclerosis and hence coronary artery disease, plaque rupture and acute coronary syndrome/myocardial infarciton (see supporting literature below). It is associated with specialized forms of cell death, pyronecrosis (Bergsbaken et al. 2009) (caspase 1 independent) and pyroptosis (Willingham et al. 2007), which may occur in cases of exacerbated inflammation. Therefore, an anti NLRP3 therapy will also decrease such death pathways, which are known to be involved in the pathogenesis of certain diseases such as atherosclerosis. Pyroptosis is a risk factor for plaque disruption in this disease in response to oxidized LDL leading to a cardiac event (Lin et al. 2013). Targeting the NLRP3 inflammasome for reducing plaque size, possible plaque rupture and possible cardiac events is therefore warranted.

InflaMab inhibits IL-1beta secretion in BMDMs—see FIG. 36. InflaMab, the bispecific IL-1RI/NLRP3 antibody, dose dependently inhibits IL-1beta from Bone Marrow Derived Macrophages (BMDMs). BMDMs were stimulated with LPS (50 ng/ml) for 3 hours, treated with or without MCC950 or Inflamab for 30 minutes, followed by Alum (50 μg/ml) for 1 hour. IL-1β release was measured in the supernatant by ELISA.

IL-1beta, but not TNFalpha, is inhibited in vivo via LPS challenge—see FIG. 37. Female apoE-/- mice, after 1 week on WTD, were injected intraperitoneally with PBS or InflaMab (100 μg or 200 μg) administrated on day 10 and day 14. After 2 weeks of diet and a 1-week treatment mice were challenged intravenously with LPS (50 μg/kg) and (a) IL-1β and (b) TNF-α were measured by ELISA.

Atherosclerosis study: InflaMab reduces plaque size in an in vivo apoe-/- model of atherosclerosis—see FIG. 38. After 2 weeks of western type diet feeding in female apoE-/- mice, carotid artery plaque formation was induced by perivascular collar placement. Mice were injected intraperitoneally with PBS or InflaMab (100 μg or 200 μg) at 3 times per week for 4 weeks. Carotid arteries then collected for cyrosections. For each carotid, lesion size was quantitated every 80 μm, from the first appearance of the lesion proximal to the collar up to complete disappearance of the lesion from the artery.

The invention is not limited to the embodiments described herein but can be amended or modified without departing from the scope of the present invention.

SEQUENCE LISTING

```
<160> NUMBER OF SEQ ID NOS: 69

<210> SEQ ID NO 1
<211> LENGTH: 550
<212> TYPE: PRT
<213> ORGANISM: Artificial Sequence
<220> FEATURE:
<223> OTHER INFORMATION: Synthetic

<400> SEQUENCE: 1

Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Glu Lys Ile Ile Leu
            20                  25                  30

Val Ser Ser Ala Asn Glu Ile Asp Val Arg Pro Cys Pro Leu Asn Pro
```

```
                35                  40                  45
Asn Glu His Lys Gly Thr Ile Thr Trp Tyr Lys Asp Asp Ser Lys Thr
             50                  55                  60
Pro Val Ser Thr Glu Gln Ala Ser Arg Ile His Gln His Lys Glu Lys
 65                  70                  75                  80
Leu Trp Phe Val Pro Ala Lys Val Glu Asp Ser Gly His Tyr Tyr Cys
                 85                  90                  95
Val Val Arg Asn Ser Ser Tyr Cys Leu Arg Ile Lys Ile Ser Ala Lys
             100                 105                 110
Phe Val Glu Asn Glu Pro Asn Leu Cys Tyr Asn Ala Gln Ala Ile Phe
         115                 120                 125
Lys Gln Lys Leu Pro Val Ala Gly Asp Gly Gly Leu Val Cys Pro Tyr
     130                 135                 140
Met Glu Phe Phe Lys Asn Glu Asn Asn Glu Leu Pro Lys Leu Gln Trp
145                 150                 155                 160
Tyr Lys Asp Cys Lys Pro Leu Leu Leu Asp Asn Ile His Phe Ser Gly
                 165                 170                 175
Val Lys Asp Arg Leu Ile Val Met Asn Val Ala Glu Lys His Arg Gly
             180                 185                 190
Asn Tyr Thr Cys His Ala Ser Tyr Thr Tyr Leu Gly Lys Gln Tyr Pro
         195                 200                 205
Ile Thr Arg Val Ile Glu Phe Ile Thr Leu Glu Glu Asn Lys Pro Thr
     210                 215                 220
Arg Pro Val Ile Val Ser Pro Ala Asn Glu Thr Met Glu Val Asp Leu
225                 230                 235                 240
Gly Ser Gln Ile Gln Leu Ile Cys Asn Val Thr Gly Gln Leu Ser Asp
                 245                 250                 255
Ile Ala Tyr Trp Lys Trp Asn Gly Ser Val Ile Asp Glu Asp Asp Pro
             260                 265                 270
Val Leu Gly Glu Asp Tyr Tyr Ser Val Glu Asn Pro Ala Asn Lys Arg
         275                 280                 285
Arg Ser Thr Leu Ile Thr Val Leu Asn Ile Ser Glu Ile Glu Ser Arg
     290                 295                 300
Phe Tyr Lys His Pro Phe Thr Cys Phe Ala Lys Asn Thr His Gly Ile
305                 310                 315                 320
Asp Ala Ala Tyr Ile Gln Leu Ile Tyr Pro Val Thr Asn Phe Gln Lys
                 325                 330                 335
Leu Glu Gly Gly Pro Ser Val Phe Ile Phe Pro Pro Asn Ile Lys Asp
             340                 345                 350
Val Leu Met Ile Ser Leu Thr Pro Lys Val Thr Cys Val Val Val Asp
         355                 360                 365
Val Ser Glu Asp Asp Pro Asp Val Gln Ile Ser Trp Phe Val Asn Asn
     370                 375                 380
Val Glu Val His Thr Ala Gln Thr Gln Thr His Arg Glu Asp Tyr Asn
385                 390                 395                 400
Ser Thr Ile Arg Val Val Ser His Leu Pro Ile Gln His Gln Asp Trp
                 405                 410                 415
Met Ser Gly Lys Glu Phe Lys Cys Lys Val Asn Asn Lys Asp Leu Pro
             420                 425                 430
Ser Pro Ile Glu Arg Thr Ile Ser Lys Pro Lys Gly Leu Val Arg Ala
         435                 440                 445
Pro Gln Val Tyr Thr Leu Pro Pro Pro Ala Glu Gln Leu Ser Arg Lys
     450                 455                 460
```

```
Asp Val Ser Leu Thr Cys Leu Val Val Gly Phe Asn Pro Gly Asp Ile
465                 470                 475                 480

Ser Val Glu Trp Thr Ser Asn Gly His Thr Glu Glu Asn Tyr Lys Asp
                485                 490                 495

Thr Ala Pro Val Leu Asp Ser Asp Gly Ser Tyr Phe Ile Tyr Ser Lys
            500                 505                 510

Leu Asn Met Lys Thr Ser Lys Trp Glu Lys Thr Asp Ser Phe Ser Cys
        515                 520                 525

Asn Val Arg His Glu Gly Leu Lys Asn Tyr Tyr Leu Lys Lys Thr Ile
    530                 535                 540

Ser Arg Ser Pro Gly Lys
545                 550

<210> SEQ ID NO 2
<211> LENGTH: 151
<212> TYPE: PRT
<213> ORGANISM: Artificial Sequence
<220> FEATURE:
<223> OTHER INFORMATION: Synthetic

<400> SEQUENCE: 2

Met Glu Trp Ser Cys Val Met Leu Phe Leu Met Ala Ala Ala Gln Ser
1               5                   10                  15

Ile Gln Ala Gln Ile Gln Leu Val Gln Ser Gly Pro Glu Leu Arg Lys
            20                  25                  30

Pro Gly Glu Thr Val Arg Ile Ser Cys Lys Ala Ser Gly Tyr Pro Phe
        35                  40                  45

Thr Thr Ala Gly Leu Gln Trp Val Gln Lys Met Ser Gly Lys Gly Leu
    50                  55                  60

Lys Trp Ile Gly Trp Met Asn Thr Gln Ser Glu Val Pro Lys Tyr Ala
65                  70                  75                  80

Glu Glu Phe Lys Gly Arg Ile Ala Phe Ser Leu Glu Thr Ala Ala Ser
                85                  90                  95

Thr Ala Tyr Leu Gln Ile Asn Asn Leu Lys Thr Glu Asp Thr Ala Thr
            100                 105                 110

Tyr Phe Cys Ala Lys Ser Val Tyr Phe Asn Trp Arg Tyr Phe Asp Val
        115                 120                 125

Trp Gly Ala Gly Thr Thr Val Thr Val Ser Ser Ala Lys Thr Thr Pro
    130                 135                 140

Pro Pro Val Tyr Pro Leu Ala
145                 150

<210> SEQ ID NO 3
<211> LENGTH: 153
<212> TYPE: PRT
<213> ORGANISM: Artificial Sequence
<220> FEATURE:
<223> OTHER INFORMATION: Synthetic

<400> SEQUENCE: 3

Val His Met Glu Cys Ser Cys Val Met Leu Phe Leu Met Ala Ala Ala
1               5                   10                  15

Gln Ser Ile Gln Ala Gln Ile Gln Leu Val Gln Ser Gly Pro Glu Leu
            20                  25                  30

Arg Lys Pro Gly Glu Thr Val Arg Ile Ser Arg Lys Ala Ser Gly Tyr
        35                  40                  45

Pro Phe Thr Thr Ala Gly Leu Gln Trp Val Gln Lys Met Ser Gly Lys
```

```
                 50                  55                  60
Gly Leu Lys Trp Ile Gly Trp Met Asn Thr Gln Ser Glu Val Pro Lys
 65                  70                  75                  80

Tyr Ala Glu Glu Phe Lys Gly Arg Ile Ala Phe Ser Leu Glu Thr Ala
                 85                  90                  95

Ala Ser Thr Ala Tyr Leu Gln Ile Asn Asn Leu Lys Thr Glu Asp Thr
                100                 105                 110

Ala Thr Tyr Phe Cys Ala Lys Ser Val Tyr Phe Asn Trp Arg Tyr Phe
                115                 120                 125

Asp Val Trp Gly Ala Gly Thr Thr Val Thr Val Ser Ser Ala Lys Thr
                130                 135                 140

Thr Pro Pro Ser Val Phe Pro Leu Ala
145                 150

<210> SEQ ID NO 4
<211> LENGTH: 153
<212> TYPE: PRT
<213> ORGANISM: Artificial Sequence
<220> FEATURE:
<223> OTHER INFORMATION: Synthetic

<400> SEQUENCE: 4

Val His Met Gly Trp Ser Trp Val Met Leu Phe Leu Met Ala Ala Ala
  1               5                  10                  15

Gln Ser Ile Gln Ala Gln Ile Gln Leu Val Gln Ser Gly Pro Glu Leu
                 20                  25                  30

Arg Lys Pro Gly Glu Thr Val Arg Ile Ser Cys Lys Ala Ser Gly Tyr
                 35                  40                  45

Pro Phe Thr Thr Ala Gly Leu Gln Trp Val Gln Lys Met Ser Gly Lys
 50                  55                  60

Gly Leu Lys Trp Ile Gly Trp Met Asn Thr Gln Ser Glu Val Pro Lys
 65                  70                  75                  80

Tyr Ala Glu Glu Phe Lys Gly Arg Ile Ala Phe Ser Leu Glu Thr Ala
                 85                  90                  95

Ala Ser Thr Ala Tyr Leu Gln Ile Asn Asn Leu Lys Thr Glu Asp Thr
                100                 105                 110

Ala Thr Tyr Phe Cys Ala Lys Ser Val Tyr Phe Asn Trp Arg Tyr Phe
                115                 120                 125

Asp Val Trp Gly Ala Gly Thr Thr Val Thr Val Ser Ser Ala Lys Thr
                130                 135                 140

Thr Pro Pro Pro Val Tyr Pro Leu Ala
145                 150

<210> SEQ ID NO 5
<211> LENGTH: 151
<212> TYPE: PRT
<213> ORGANISM: Artificial Sequence
<220> FEATURE:
<223> OTHER INFORMATION: Synthetic

<400> SEQUENCE: 5

Met Gly Trp Val Trp Asn Leu Leu Phe Leu Met Ala Ala Ala Gln Ser
  1               5                  10                  15

Ile Gln Ala Gln Ile Gln Leu Val Gln Ser Gly Pro Glu Leu Arg Lys
                 20                  25                  30

Pro Gly Glu Thr Val Arg Ile Ser Cys Lys Ala Ser Gly Tyr Pro Phe
                 35                  40                  45
```

Thr Thr Ala Gly Leu Gln Trp Val Gln Lys Met Ser Gly Lys Gly Leu
     50                  55                  60

Lys Trp Ile Gly Trp Met Asn Thr Gln Ser Glu Val Pro Lys Tyr Ala
 65              70                  75                  80

Glu Glu Phe Lys Gly Arg Ile Ala Phe Ser Leu Glu Thr Ala Ala Ser
                 85                  90                  95

Thr Ala Tyr Leu Gln Ile Asn Asn Leu Lys Thr Glu Asp Thr Ala Thr
            100                 105                 110

Tyr Phe Cys Ala Lys Ser Val Tyr Phe Asn Trp Arg Tyr Phe Asp Val
        115                 120                 125

Trp Gly Ala Gly Thr Thr Val Thr Val Ser Ser Ala Lys Thr Thr Pro
    130                 135                 140

Pro Pro Val Tyr Pro Leu Val
145             150

<210> SEQ ID NO 6
<211> LENGTH: 151
<212> TYPE: PRT
<213> ORGANISM: Artificial Sequence
<220> FEATURE:
<223> OTHER INFORMATION: Synthetic

<400> SEQUENCE: 6

Met Gly Trp Val Trp Thr Leu Pro Phe Leu Met Ala Ala Ala Gln Ser
1               5                   10                  15

Ile Gln Ala Gln Ile Gln Leu Val Gln Ser Gly Pro Glu Leu Arg Lys
            20                  25                  30

Pro Gly Glu Thr Val Arg Ile Ser Cys Lys Ala Ser Gly Tyr Pro Phe
        35                  40                  45

Thr Thr Ala Gly Leu Gln Trp Val Gln Lys Met Ser Gly Lys Gly Leu
     50                  55                  60

Lys Trp Ile Gly Trp Met Asn Thr Gln Ser Glu Val Pro Lys Tyr Ala
 65              70                  75                  80

Glu Glu Phe Lys Gly Arg Ile Ala Phe Ser Leu Glu Thr Ala Ala Ser
                 85                  90                  95

Thr Ala Tyr Leu Gln Ile Asn Asn Leu Lys Thr Glu Asp Thr Ala Thr
            100                 105                 110

Tyr Phe Cys Ala Lys Ser Val Tyr Phe Asn Trp Arg Tyr Phe Asp Val
        115                 120                 125

Trp Gly Ala Gly Thr Thr Val Thr Val Ser Ser Ala Lys Thr Thr Pro
    130                 135                 140

Pro Pro Val Tyr Pro Leu Val
145             150

<210> SEQ ID NO 7
<211> LENGTH: 151
<212> TYPE: PRT
<213> ORGANISM: Artificial Sequence
<220> FEATURE:
<223> OTHER INFORMATION: Synthetic

<400> SEQUENCE: 7

Met Gly Trp Val Trp Asn Leu Pro Phe Leu Met Ala Ala Ala Gln Ser
1               5                   10                  15

Ile Gln Ala Gln Ile Gln Leu Val Gln Ser Gly Pro Glu Leu Arg Lys
            20                  25                  30

Pro Gly Glu Thr Val Arg Ile Ser Cys Lys Ala Ser Gly Tyr Pro Phe
        35                  40                  45

Thr Thr Ala Gly Leu Gln Trp Val Gln Lys Met Ser Gly Lys Gly Leu
        50                  55                  60

Lys Trp Ile Gly Trp Met Asn Thr Gln Ser Glu Val Pro Lys Tyr Ala
65                  70                  75                  80

Glu Glu Phe Lys Gly Arg Ile Ala Phe Ser Leu Glu Thr Ala Ala Ser
                85                  90                  95

Thr Ala Tyr Leu Gln Ile Asn Asn Leu Lys Thr Glu Asp Thr Ala Thr
            100                 105                 110

Tyr Phe Cys Ala Lys Ser Val Tyr Phe Asn Trp Arg Tyr Phe Asp Val
            115                 120                 125

Trp Gly Ala Gly Thr Thr Val Thr Val Ser Ser Ala Lys Thr Thr Pro
        130                 135                 140

Pro Pro Val Tyr Pro Leu Ala
145                 150

<210> SEQ ID NO 8
<211> LENGTH: 151
<212> TYPE: PRT
<213> ORGANISM: Artificial Sequence
<220> FEATURE:
<223> OTHER INFORMATION: Synthetic

<400> SEQUENCE: 8

Met Asp Trp Val Trp Thr Leu Pro Phe Leu Met Ala Ala Ala Gln Ser
1               5                   10                  15

Ile Gln Ala Gln Ile Gln Leu Val Gln Ser Gly Pro Glu Leu Arg Lys
            20                  25                  30

Pro Gly Glu Thr Val Arg Ile Ser Cys Lys Ala Ser Gly Tyr Pro Phe
        35                  40                  45

Thr Thr Ala Gly Leu Gln Trp Val Gln Lys Met Ser Gly Lys Gly Leu
        50                  55                  60

Lys Trp Ile Gly Trp Met Asn Thr Gln Ser Glu Val Pro Lys Tyr Ala
65                  70                  75                  80

Glu Glu Phe Lys Gly Arg Ile Ala Phe Ser Leu Glu Thr Ala Ala Ser
                85                  90                  95

Thr Ala Tyr Leu Gln Ile Asn Asn Leu Lys Thr Glu Asp Thr Ala Thr
            100                 105                 110

Tyr Phe Cys Ala Lys Ser Val Tyr Phe Asn Trp Arg Tyr Phe Asp Val
            115                 120                 125

Trp Gly Ala Gly Thr Thr Val Thr Val Ser Ser Ala Lys Thr Thr Pro
        130                 135                 140

Pro Ser Val Tyr Pro Leu Ala
145                 150

<210> SEQ ID NO 9
<211> LENGTH: 151
<212> TYPE: PRT
<213> ORGANISM: Artificial Sequence
<220> FEATURE:
<223> OTHER INFORMATION: Synthetic

<400> SEQUENCE: 9

Met Asp Trp Leu Trp Asn Leu Pro Phe Leu Met Ala Ala Ala Gln Ser
1               5                   10                  15

Ile Gln Ala Gln Ile Gln Leu Val Gln Ser Gly Pro Glu Leu Arg Lys
            20                  25                  30

Pro Gly Glu Thr Val Arg Ile Ser Cys Lys Ala Ser Gly Tyr Pro Phe

```
                35                  40                  45
Thr Thr Ala Gly Leu Gln Trp Val Gln Lys Met Ser Gly Lys Gly Leu
 50                  55                  60

Lys Trp Ile Gly Trp Met Asn Thr Gln Ser Glu Val Pro Lys Tyr Ala
 65                  70                  75                  80

Glu Glu Phe Lys Gly Arg Ile Ala Phe Ser Leu Glu Thr Ala Ala Ser
                 85                  90                  95

Thr Ala Tyr Leu Gln Ile Asn Asn Leu Lys Thr Glu Asp Thr Ala Thr
            100                 105                 110

Tyr Phe Cys Ala Lys Ser Val Tyr Phe Asn Trp Arg Tyr Phe Asp Val
            115                 120                 125

Trp Gly Ala Gly Thr Thr Val Thr Val Ser Ser Ala Lys Thr Thr Pro
130                 135                 140

Pro Pro Val Tyr Pro Leu Ala
145                 150

<210> SEQ ID NO 10
<211> LENGTH: 162
<212> TYPE: PRT
<213> ORGANISM: Artificial Sequence
<220> FEATURE:
<223> OTHER INFORMATION: Synthetic

<400> SEQUENCE: 10

Met Arg Ala Pro Ala Gln Phe Leu Gly Leu Leu Leu Leu Trp Thr Ser
 1               5                  10                  15

Ala Ser Arg Cys Asp Ile Val Met Thr Gln Ser Pro Ala Thr Leu Ser
             20                  25                  30

Val Thr Pro Gly Asp Arg Val Ser Leu Ser Cys Arg Ala Ser Gln Ser
             35                  40                  45

Ile Ser Asp Tyr Leu Ser Trp Tyr Gln Gln Arg Ser His Glu Ser Pro
 50                  55                  60

Arg Leu Ile Ile Lys Tyr Ala Ser Gln Ser Ile Ser Gly Ile Pro Ser
 65                  70                  75                  80

Arg Phe Ser Gly Ser Gly Ser Gly Ser Asp Phe Thr Leu Ser Ile Asn
                 85                  90                  95

Ser Val Glu Pro Glu Asp Val Gly Val Tyr Tyr Cys Gln His Gly His
            100                 105                 110

Ser Phe Pro Leu Thr Phe Gly Ser Gly Thr Lys Leu Glu Leu Lys Arg
            115                 120                 125

Ala Asp Ala Ala Pro Thr Val Ser Ile Phe Pro Pro Ser Ser Glu Gln
            130                 135                 140

Leu Thr Ser Gly Gly Ala Ser Val Val Cys Phe Leu Asn Asn Phe Tyr
145                 150                 155                 160

Pro Lys

<210> SEQ ID NO 11
<211> LENGTH: 162
<212> TYPE: PRT
<213> ORGANISM: Artificial Sequence
<220> FEATURE:
<223> OTHER INFORMATION: Synthetic

<400> SEQUENCE: 11

Met Arg Ala Pro Ala Gln Phe Leu Gly Leu Leu Leu Phe Trp Thr Ser
 1               5                  10                  15

Ala Ser Arg Cys Asp Ile Val Met Thr Gln Ser Pro Ala Thr Leu Ser
```

```
                20                  25                  30
Val Thr Pro Gly Asp Arg Val Ser Leu Ser Cys Arg Ala Ser Gln Ser
             35                  40                  45

Ile Ser Asp Tyr Leu Ser Trp Tyr Gln Gln Arg Ser His Glu Ser Pro
 50                  55                  60

Arg Leu Ile Ile Lys Tyr Ala Ser Gln Ser Ile Ser Gly Ile Pro Ser
 65                  70                  75                  80

Arg Phe Ser Gly Ser Gly Ser Gly Ser Asp Phe Thr Leu Asn Ile Asn
                 85                  90                  95

Ser Val Glu Pro Glu Asp Val Gly Val Tyr Tyr Cys Gln His Gly His
                100                 105                 110

Ser Phe Pro Leu Thr Phe Gly Ser Gly Thr Lys Leu Glu Leu Lys Arg
            115                 120                 125

Ala Asp Ala Ala Pro Thr Val Ser Ile Phe Pro Ser Ser Glu Gln
            130                 135                 140

Leu Thr Ser Gly Gly Ala Ser Val Val Cys Phe Leu Asn Asn Phe Tyr
145                 150                 155                 160

Pro Lys

<210> SEQ ID NO 12
<211> LENGTH: 162
<212> TYPE: PRT
<213> ORGANISM: Artificial Sequence
<220> FEATURE:
<223> OTHER INFORMATION: Synthetic

<400> SEQUENCE: 12

Met Arg Ser Pro Ala Gln Phe Leu Gly Leu Leu Phe Trp Thr Ser
1                5                  10                  15

Ala Ser Arg Cys Asp Ile Val Met Thr Gln Ser Pro Ala Thr Leu Ser
                 20                  25                  30

Val Thr Pro Gly Asp Arg Val Ser Leu Ser Cys Arg Ala Ser Gln Ser
             35                  40                  45

Ile Ser Asp Tyr Leu Ser Trp Tyr Gln Gln Arg Ser His Glu Ser Pro
 50                  55                  60

Arg Leu Ile Ile Lys Tyr Ala Ser Gln Ser Ile Ser Gly Ile Pro Ser
 65                  70                  75                  80

Arg Phe Ser Gly Ser Gly Ser Gly Ser Asp Phe Thr Leu Ser Ile Asn
                 85                  90                  95

Ser Val Glu Pro Glu Asp Val Gly Val Tyr Tyr Cys Gln His Gly His
                100                 105                 110

Ser Phe Pro Leu Thr Phe Gly Ser Gly Thr Lys Leu Glu Leu Lys Arg
            115                 120                 125

Ala Asp Ala Ala Pro Thr Val Ser Ile Phe Pro Ser Ser Glu Gln
            130                 135                 140

Leu Thr Ser Gly Gly Ala Ser Val Val Cys Phe Leu Asn Asn Phe Tyr
145                 150                 155                 160

Pro Lys

<210> SEQ ID NO 13
<211> LENGTH: 162
<212> TYPE: PRT
<213> ORGANISM: Artificial Sequence
<220> FEATURE:
<223> OTHER INFORMATION: Synthetic

<400> SEQUENCE: 13
```

Met Arg Ser Pro Ala Gln Phe Leu Gly Leu Leu Phe Trp Thr Ser
1               5                   10                  15

Ala Ser Arg Cys Asp Ile Val Met Thr Gln Ser Pro Ala Thr Leu Ser
                20                  25                  30

Val Thr Pro Gly Asp Arg Val Ser Leu Ser Cys Arg Ala Ser Gln Ser
            35                  40                  45

Ile Ser Asp Tyr Leu Ser Trp Tyr Gln Gln Arg Ser His Glu Ser Pro
    50                  55                  60

Arg Leu Ile Ile Lys Tyr Ala Ser Gln Ser Ile Ser Gly Ile Pro Ser
65                  70                  75                  80

Arg Phe Ser Gly Ser Gly Ser Gly Ser Asp Phe Thr Leu Ser Ile Asn
                85                  90                  95

Ser Val Glu Pro Glu Asp Val Gly Val Tyr Tyr Cys Gln His Gly His
                100                 105                 110

Ser Phe Pro Leu Thr Phe Gly Ser Gly Thr Lys Leu Glu Leu Lys Arg
            115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Arg

<210> SEQ ID NO 14
<211> LENGTH: 162
<212> TYPE: PRT
<213> ORGANISM: Artificial Sequence
<220> FEATURE:
<223> OTHER INFORMATION: Synthetic

<400> SEQUENCE: 14

Met Val Ser Ser Ala Gln Phe Leu Gly Leu Leu Phe Trp Thr Ser
1               5                   10                  15

Ala Ser Arg Cys Asp Ile Val Met Thr Gln Ser Pro Ala Thr Leu Ser
                20                  25                  30

Val Thr Pro Gly Asp Arg Val Ser Leu Ser Cys Arg Ala Ser Gln Ser
            35                  40                  45

Ile Ser Asp Tyr Leu Ser Trp Tyr Gln Gln Arg Ser His Glu Ser Pro
    50                  55                  60

Arg Leu Ile Ile Lys Tyr Ala Ser Gln Ser Ile Ser Gly Ile Pro Ser
65                  70                  75                  80

Arg Phe Ser Gly Ser Gly Ser Gly Ser Asp Phe Thr Leu Ser Ile Asn
                85                  90                  95

Ser Val Glu Pro Glu Asp Val Gly Val Tyr Tyr Cys Gln His Gly His
                100                 105                 110

Ser Phe Pro Leu Thr Phe Gly Ser Gly Thr Lys Leu Glu Leu Lys Arg
            115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys

<210> SEQ ID NO 15
<211> LENGTH: 162
<212> TYPE: PRT

<213> ORGANISM: Artificial Sequence
<220> FEATURE:
<223> OTHER INFORMATION: Synthetic

<400> SEQUENCE: 15

```
Met Val Ser Thr Ala Gln Phe Leu Gly Leu Leu Leu Phe Trp Thr Ser
1               5                   10                  15

Ala Ser Arg Cys Asp Ile Val Met Thr Gln Ser Pro Ala Thr Leu Ser
            20                  25                  30

Val Thr Pro Gly Asp Arg Val Ser Leu Ser Cys Arg Ala Ser Gln Ser
        35                  40                  45

Ile Ser Asp Tyr Leu Ser Trp Tyr Gln Gln Arg Ser His Glu Ser Pro
    50                  55                  60

Arg Leu Ile Ile Lys Tyr Ala Ser Gln Ser Ile Ser Gly Ile Pro Ser
65                  70                  75                  80

Arg Phe Ser Gly Ser Gly Ser Gly Ser Asp Phe Thr Leu Ser Ile Asn
                85                  90                  95

Ser Val Glu Pro Glu Asp Val Gly Val Tyr Tyr Cys Gln His Gly His
                100                 105                 110

Ser Phe Pro Leu Thr Phe Gly Ser Gly Thr Lys Leu Glu Leu Lys Arg
            115                 120                 125

Ala Asp Ala Ala Pro Thr Val Ser Ile Phe Pro Pro Ser Ser Glu Gln
        130                 135                 140

Leu Thr Ser Gly Gly Ala Ser Val Val Cys Phe Leu Asn Asn Phe Tyr
145                 150                 155                 160

Pro Arg
```

<210> SEQ ID NO 16
<211> LENGTH: 453
<212> TYPE: DNA
<213> ORGANISM: Artificial Sequence
<220> FEATURE:
<223> OTHER INFORMATION: Synthetic

<400> SEQUENCE: 16

```
atggaatgga gctgtgtcat gctctttctc atggcagcag ctcaaagtat ccaagcacag    60
atccagttgg tgcagtctgg acctgagctg aggaagcctg agagacagt caggatctcc    120
tgcaaggcct ctgggtatcc cttcacaact gctggattgc agtgggtaca gaagatgtca    180
ggaaagggtt tgaaatggat tggctggatg aacacccagt ctgaagtgcc aaaatatgca    240
gaagagttca aggacggat tgccttctct ttggaaaccg ctgccagtac tgcatattta    300
cagataaaca acctcaaaac tgaggacacg gcaacgtatt tctgtgcgaa atcggtctat    360
tttaactgga gatatttcga tgtctggggt gcagggacca cggtcaccgt ctcctcagcc    420
aaaacgacac ccccacccgt ttatccactg gcc                                  453
```

<210> SEQ ID NO 17
<211> LENGTH: 453
<212> TYPE: DNA
<213> ORGANISM: Artificial Sequence
<220> FEATURE:
<223> OTHER INFORMATION: Synthetic

<400> SEQUENCE: 17

```
atgggatgga gctgggtcat gctctttctc atggcagcag ctcaaagtat ccaagcacag    60
atccagttgg tgcagtctgg acctgagctg aggaagcctg agagacagt caggatctcc    120
tgcaaggctt ctgggtatcc cttcacaact gctggactgc agtgggtaca gaagatgtca    180
```

```
ggaaagggtt tgaaatggat tggctggatg aacacccagt ctgaagtgcc aaaatatgca      240
gaagagttca agggacggat tgccttctct ttggaaaccg ctgccagtac tgcatattta      300
cagataaaca acctcaaaac tgaggacacg gcaacgtatt tctgtgcgaa atcggtctat      360
tttaactgga gatatttcga tgtctggggt gcagggacca cggtcaccgt ctcctcagcc      420
aaaacgacac ccccacccgt ttatcccttg gcc                                   453
```

<210> SEQ ID NO 18
<211> LENGTH: 453
<212> TYPE: DNA
<213> ORGANISM: Artificial Sequence
<220> FEATURE:
<223> OTHER INFORMATION: Synthetic

<400> SEQUENCE: 18

```
atggaatgca gctgtgtaat gctctttctc atggcagcag ctcaaagtat ccaagcacag      60
atccagttgg tgcagtctgg acctgagctg aggaagcctg gagagacagt caggatctcc     120
cgcaaggctt ctgggtatcc cttcacaact gctggattgc agtgggtaca gaagatgtca     180
ggaaagggtt tgaaatggat tggctggatg aacacccagt ctgaagtgcc aaaatatgca     240
gaagagttca agggacggat tgccttctct ttggaaaccg ctgccagtac tgcatattta     300
cagataaaca acctcaaaac tgaggacacg gcaacgtatt tctgtgcgaa atcggtctat     360
tttaactgga gatatttcga tgtctggggt gcagggacca cggtcaccgt ctcctcagcc     420
aaaacgacac cccatccgt cttccccctg gca                                    453
```

<210> SEQ ID NO 19
<211> LENGTH: 453
<212> TYPE: DNA
<213> ORGANISM: Artificial Sequence
<220> FEATURE:
<223> OTHER INFORMATION: Synthetic

<400> SEQUENCE: 19

```
atgggttggg tgtggaactt gctattcctc atggcagcag ctcaaagtat ccaagcacag      60
atccagctgg tgcagtctgg acctgagctg aggaagcctg gagagacagt caggatctcc     120
tgcaaggctt ctgggtatcc cttcacaact gctggattgc agtgggtaca gaagatgtca     180
ggaaagggtt tgaaatggat tggctggatg aacacccagt ctgaagtgcc aaaatatgca     240
gaagagttca agggacggat tgccttctct ttggaaaccg ctgccagtac tgcatattta     300
cagataaaca acctcaaaac tgaggacacg gcaacgtatt tctgtgcgaa atcggtctat     360
tttaactgga gatatttcga tgtctggggt gcagggacca cggtcaccgt ctcctcagcc     420
aaaacgacac ccccacccgt ctatccactg gtc                                   453
```

<210> SEQ ID NO 20
<211> LENGTH: 453
<212> TYPE: DNA
<213> ORGANISM: Artificial Sequence
<220> FEATURE:
<223> OTHER INFORMATION: Synthetic

<400> SEQUENCE: 20

```
atggattggg tgtggaccct gccattcctc atggcagcag ctcaaagtat ccaagcacag      60
atccagttgg tgcagtctgg acctgagctg aggaagcctg gagagacagt caggatctcc     120
tgcaaggctt ctgggtatcc cttcacaact gctggattgc agtgggtaca gaagatgtca     180
```

```
ggaaagggtt tgaaatggat tggctggatg aacacccagt ctgaagtgcc aaaatatgca        240
gaagagttca aggacggat  tgccttctct ttggaaaccg ctgccagtac tgcatattta        300
cagataaaca acctcaaaac tgaggacacg gcaacgtatt tctgtgcgaa atcggtctat        360
tttaactgga gatatttcga tgtctggggt gcagggacca cggtcaccgt ctcctcagcc        420
aaaacgacac ccccatctgt ctatccactg gcc                                    453

<210> SEQ ID NO 21
<211> LENGTH: 453
<212> TYPE: DNA
<213> ORGANISM: Artificial Sequence
<220> FEATURE:
<223> OTHER INFORMATION: Synthetic

<400> SEQUENCE: 21
atgggttggg tgtggaactt gccattcctc atggcagcag ctcaaagtat ccaagcacag         60
atccagttgg tgcagtctgg acctgagctg aggaagcctg agagacagt caggatctcc        120 tgcaaggctt ctgggtatcc cttcacaact gctggattgc agtgggtaca gaagatgtca        180
ggaaagggtt tgaaatggat tggctggatg aacacccagt ctgaagtacc aaaatatgca        240
gaagagttca agggacggat tgccttctct ttggaaaccg ctgccagcac tgcatattta        300
cagataaaca acctcaaaac tgaggacacg gcaacgtatt tctgtgcgaa atcggtctat        360
tttaactgga gatatttcga tgtctggggt gcagggacca cggtcaccgt ctcctcagcc        420
aaaacgacac ccccacccgt ctatccattg gcc                                    453

<210> SEQ ID NO 22
<211> LENGTH: 453
<212> TYPE: DNA
<213> ORGANISM: Artificial Sequence
<220> FEATURE:
<223> OTHER INFORMATION: Synthetic

<400> SEQUENCE: 22
atggattggc tgtggaactt gccattcctc atggcagcag ctcaaagtat ccaagcacag         60
atccagttgg tgcagtctgg acctgagctg aggaagcctg agagacagt caggatctcc        120 tgcaaggctt ctgggtatcc cttcacaact gctggattgc agtgggtaca gaagatgtca        180
ggaaagggtt tgaaatggat tggctggatg aacacccagt ctgaagtgcc aaaatatgca        240
gaagagttca agggacggat tgccttctct ttggaaaccg ctgccagtac tgcatattta        300
cagataaaca acctcaaaac tgaggacacg gcaacgtatt tctgtgcgaa atcggtctat        360
tttaactgga gatatttcga tgtctggggt gcagggacca cggtcaccgt ctcctcagcc        420
aaaacgacac ccccacccgt ctatccactg gcc                                    453

<210> SEQ ID NO 23
<211> LENGTH: 453
<212> TYPE: DNA
<213> ORGANISM: Artificial Sequence
<220> FEATURE:
<223> OTHER INFORMATION: Synthetic

<400> SEQUENCE: 23
atgggttggg tgtggacctt gccattcctc atggcagcag ctcaaagtat ccaagcacag         60
atccagttgg tgcagtctgg acctgagctg aggaagcctg agagacagt caggatctcc        120 tgcaaggctt ctgggtatcc cttcacaact gctggattgc agtgggtaca gaagatgtca        180
ggaaagggtt tgaaatggat tggctggatg aacacccagt ctgaagtgcc aaaatatgca        240
```

| | |
|---|---|
| gaagagttca agggacggat tgccttctct ttggaaaccg ctgccagtac tgcatattta | 300 |
| cagataaaca acctcaaaac tgaggacacg gcgacgtatt tctgtgcgaa atcggtctat | 360 |
| tttaactgga gatatttcga tgtctggggt gcagggacca cggtcaccgt ctcctcagcc | 420 |
| aaaacgacac ccccacccgt ctatcccctg gtc | 453 |

<210> SEQ ID NO 24
<211> LENGTH: 488
<212> TYPE: DNA
<213> ORGANISM: Artificial Sequence
<220> FEATURE:
<223> OTHER INFORMATION: Synthetic

<400> SEQUENCE: 24

| | |
|---|---|
| atgagggccc ctgctcagtt tcttgggctt ttgcttctct ggacttcagc ctccagatgt | 60 |
| gacattgtga tgactcagtc tccagccacc ctgtctgtga ctccaggaga tagagtctct | 120 |
| ctttcctgca gggccagcca gagtattagc gactacttat cctggtatca acaaagatct | 180 |
| catgagtctc caaggcttat catcaaatat gcttcccaat ccatctctgg gatcccctcc | 240 |
| aggttcagtg gcagtggatc agggtcagac ttcactctca gtatcaacag tgtggaacct | 300 |
| gaagatgttg gagtgtatta ctgtcaacat ggtcacagct ttccgctcac gttcggttct | 360 |
| gggaccaagc tggagctgaa acgggctgat gctgcaccaa ctgtatccat cttcccacca | 420 |
| tccagtgagc agttaacatc tggaggtgcc tcagtcgtgt gcttcttgaa caacttctac | 480 |
| cccaaaga | 488 |

<210> SEQ ID NO 25
<211> LENGTH: 486
<212> TYPE: DNA
<213> ORGANISM: Artificial Sequence
<220> FEATURE:
<223> OTHER INFORMATION: Synthetic

<400> SEQUENCE: 25

| | |
|---|---|
| atgaggtccc ctgctcagtt ccttgggctt ttgcttttct ggacttcagc ctccagatgt | 60 |
| gacattgtga tgactcagtc tccagccacc ctgtctgtga ctccaggaga tagagtctct | 120 |
| ctttcctgca gggccagcca gagtattagc gactacttat cctggtatca acaaagatct | 180 |
| catgagtctc caaggcttat catcaaatat gcttcccaat ccatctctgg gatcccctcc | 240 |
| aggttcagtg gcagtggatc agggtcagac ttcactctca gtatcaacag tgtggaacct | 300 |
| gaagatgttg gagtgtatta ctgtcaacat ggtcacagct ttccgctcac gttcggttct | 360 |
| gggaccaagc tggagctgaa acgggctgat gctgcaccaa ctgtatccat cttcccacca | 420 |
| tccagtgagc agttaacatc tggaggtgcc tcagtcgtgt gcttcttgaa caacttctac | 480 |
| cccaaa | 486 |

<210> SEQ ID NO 26
<211> LENGTH: 488
<212> TYPE: DNA
<213> ORGANISM: Artificial Sequence
<220> FEATURE:
<223> OTHER INFORMATION: Synthetic

<400> SEQUENCE: 26

| | |
|---|---|
| atgaggtccc cagctcagtt tctggggctt ttgcttttct ggacttcagc ctccagatgt | 60 |
| gacattgtga tgactcagtc tccagccacc ctgtctgtga ctccaggaga tagagtctct | 120 |

-continued

| | | |
|---|---|---|
| ctttcctgca gggccagcca gagtattagc gactacttat cctggtatca acaaagatct | 180 | |
| catgagtctc caaggcttat catcaaatat gcttcccaat ccatctctgg gatcccctcc | 240 | |
| aggttcagtg gcagtggatc agggtcagac ttcactctca gtatcaacag tgtggaacct | 300 | |
| gaagatgttg gagtgtatta ctgtcaacat ggtcacagct ttccgctcac gttcggttct | 360 | |
| gggaccaagc tggagctgaa acgggctgat gctgcaccaa ctgtatccat cttcccacca | 420 | |
| tccagtgagc agttaacatc tggaggtgcc tcagtcgtgt gcttcttgaa caacttctac | 480 | |
| cccagaga | 488 | |

<210> SEQ ID NO 27
<211> LENGTH: 488
<212> TYPE: DNA
<213> ORGANISM: Artificial Sequence
<220> FEATURE:
<223> OTHER INFORMATION: Synthetic

<400> SEQUENCE: 27

| | | |
|---|---|---|
| atgagggccc ctgctcagct cctggggctt ttgcttttct ggacttcagc ctccagatgt | 60 | |
| gacattgtga tgactcagtc tccagccacc ctgtctgtga ctccaggaga tagagtctct | 120 | |
| ctttcctgca gggccagcca gagtattagc gactacttat cctggtatca acaaagatct | 180 | |
| catgagtctc caaggcttat catcaaatat gcttcccaat ccatctctgg gatcccctcc | 240 | |
| aggttcagtg gcagtggatc agggtcagac ttcactctca atatcaacag tgtggaacct | 300 | |
| gaagatgttg gagtgtatta ctgtcaacat ggtcacagct ttccgctcac gttcggttct | 360 | |
| gggaccaagc tggagctgaa acgggctgat gctgcaccaa ctgtatccat cttcccacca | 420 | |
| tccagtgagc agttaacatc tggaggtgcc tcagtcgtgt gcttcttgaa caacttctat | 480 | |
| cccaaaga | 488 | |

<210> SEQ ID NO 28
<211> LENGTH: 486
<212> TYPE: DNA
<213> ORGANISM: Artificial Sequence
<220> FEATURE:
<223> OTHER INFORMATION: Synthetic]

<400> SEQUENCE: 28

| | | |
|---|---|---|
| atggtatcct cagctcagtt ccttggactt ttgcttttct ggacttcagc ctccagatgt | 60 | |
| gacattgtga tgactcagtc tccagccacc ctgtctgtga ctccaggaga tagagtctct | 120 | |
| ctttcctgca gggccagcca gagtattagc gactacttat cctggtatca acaaagatct | 180 | |
| catgagtctc caaggcttat catcaaatat gcttcccaat ccatctctgg gatcccctcc | 240 | |
| aggttcagtg gcagtggatc agggtcagac ttcactctca gtatcaacag tgtggaacct | 300 | |
| gaagatgttg gagtgtatta ctgtcaacat ggtcacagct ttccgctcac gttcggttct | 360 | |
| gggaccaagc tggagctgaa acgggctgat gctgcaccaa ctgtatccat cttcccacca | 420 | |
| tccagtgagc agttaacatc tggaggtgcc tcagtcgtgt gcttcttgaa caacttctac | 480 | |
| cccaaa | 486 | |

<210> SEQ ID NO 29
<211> LENGTH: 488
<212> TYPE: DNA
<213> ORGANISM: Artificial Sequence
<220> FEATURE:
<223> OTHER INFORMATION: Synthetic

<400> SEQUENCE: 29

```
atggtgtcca cagctcagtt ccttggactt ttgcttttct ggacttcagc ctccagatgt    60
gacattgtga tgactcagtc tccagccacc ctgtctgtga ctccaggaga tagagtctct   120
ctttcctgca gggccagcca gagtattagc gactacttat cctggtatca acaaagatct   180
catgagtctc caaggcttat catcaaatat gcttcccaat ccatctctgg atcccctcc   240 aggttcagtg gcagtggatc agggtcagac ttcactctca gtatcaacag tgtggaacct   300
gaagatgttg gagtgtatta ctgtcaacat ggtcacagct ttccgctcac gttcggttct   360
gggaccaagc tggagctgaa acgggctgat gctgcaccaa ctgtatccat cttcccacca   420
tccagtgagc agttaacatc tggaggtgcc tcagtcgtgt gcttcttgaa caacttctac   480
cccagaga                                                            488

<210> SEQ ID NO 30
<211> LENGTH: 24
<212> TYPE: PRT
<213> ORGANISM: Artificial Sequence
<220> FEATURE:
<223> OTHER INFORMATION: Synthetic

<400> SEQUENCE: 30

Glu Asp Tyr Pro Pro Gln Lys Gly Cys Ile Pro Leu Pro Arg Gly Gln
1               5                   10                  15

Thr Glu Lys Ala Asp His Val Asp
            20

<210> SEQ ID NO 31
<211> LENGTH: 19
<212> TYPE: PRT
<213> ORGANISM: Artificial Sequence
<220> FEATURE:
<223> OTHER INFORMATION: Synthetic

<400> SEQUENCE: 31

Gln Lys Gly Cys Ile Pro Leu Pro Arg Gly Gln Thr Glu Lys Ala Asp
1               5                   10                  15

His Val Asp

<210> SEQ ID NO 32
<211> LENGTH: 15
<212> TYPE: PRT
<213> ORGANISM: Artificial Sequence
<220> FEATURE:
<223> OTHER INFORMATION: Synthetic

<400> SEQUENCE: 32

Gln Lys Gly Cys Ile Pro Leu Pro Arg Gly Gln Thr Glu Lys Ala
1               5                   10                  15

<210> SEQ ID NO 33
<211> LENGTH: 106
<212> TYPE: PRT
<213> ORGANISM: Artificial Sequence
<220> FEATURE:
<223> OTHER INFORMATION: Synthetic

<400> SEQUENCE: 33

Met Asn Phe Gly Leu Ser Leu Val Phe Leu Val Leu Val Leu Lys Gly
1               5                   10                  15

Ala Gln Cys Glu Val Gln Leu Val Glu Ser Gly Gly Gly Leu Val Lys
            20                  25                  30
```

```
Pro Gly Gly Ser Leu Lys Leu Ser Cys Ala Ala Ser Gly Phe Thr Phe
         35                  40                  45

Ser Asp Tyr Tyr Met Tyr Trp Val Arg Gln Thr Pro Glu Lys Arg Leu
 50                  55                  60

Glu Trp Val Ala Thr Ile Ser Asp Gly Gly Tyr Thr Tyr Tyr Pro
 65                  70                  75                  80

Asp Ser Val Lys Gly Arg Phe Thr Ile Ser Arg Asp Asn Ala Lys Asn
                 85                  90                  95

Asn Leu Tyr Leu Gln Met Asn Ser Leu Lys
                100                 105
```

<210> SEQ ID NO 34
<211> LENGTH: 147
<212> TYPE: PRT
<213> ORGANISM: Artificial Sequence
<220> FEATURE:
<223> OTHER INFORMATION: Synthetic

<400> SEQUENCE: 34

```
Phe Leu Val Leu Val Leu Lys Gly Val Gln Cys Glu Val Gln Leu Val
 1               5                  10                  15

Glu Ser Gly Gly Gly Leu Val Lys Pro Gly Gly Ser Leu Lys Leu Ser
                 20                  25                  30

Cys Ala Ala Ser Gly Phe Thr Phe Ser Asp Tyr Tyr Met Tyr Trp Val
             35                  40                  45

Arg Gln Thr Pro Glu Lys Arg Leu Glu Trp Val Ala Thr Ile Ser Asp
 50                  55                  60

Gly Gly Tyr Thr Tyr Tyr Pro Asp Ser Val Lys Gly Arg Phe Thr
 65                  70                  75                  80

Ile Ser Arg Asp Asn Ala Lys Asn Asn Leu Tyr Leu Gln Met Asn Ser
                 85                  90                  95

Leu Lys Ser Glu Asp Thr Ala Met Tyr Tyr Cys Ala Arg Gly Trp Val
                100                 105                 110

Ser Thr Met Val Lys Leu Leu Ser Ser Phe Pro Tyr Trp Gly Gln Gly
             115                 120                 125

Thr Leu Val Thr Val Ser Ala Ala Lys Thr Thr Pro Pro Ser Val Tyr
             130                 135                 140

Pro Leu Ala
145
```

<210> SEQ ID NO 35
<211> LENGTH: 155
<212> TYPE: PRT
<213> ORGANISM: Artificial Sequence
<220> FEATURE:
<223> OTHER INFORMATION: Synthetic

<400> SEQUENCE: 35

```
Met Asp Phe Gly Leu Ser Arg Val Phe Leu Val Leu Val Leu Lys Gly
 1               5                  10                  15

Val Gln Cys Glu Val Gln Leu Val Glu Ser Gly Gly Gly Leu Val Lys
                 20                  25                  30

Pro Gly Gly Ser Leu Lys Leu Ser Cys Ala Ala Ser Gly Phe Thr Phe
             35                  40                  45

Ser Asp Tyr Tyr Met Tyr Trp Val Arg Gln Thr Pro Glu Lys Arg Leu
 50                  55                  60

Glu Trp Val Ala Thr Ile Ser Asp Gly Gly Tyr Thr Tyr Tyr Pro
 65                  70                  75                  80
```

Asp Ser Val Lys Gly Arg Phe Thr Ile Ser Arg Asp Asn Ala Lys Asn
            85                  90                  95

Asn Leu Tyr Leu Gln Met Asn Ser Leu Lys Ser Glu Asp Thr Ala Met
            100                 105                 110

Tyr Tyr Cys Ala Arg Gly Trp Val Ser Thr Met Val Lys Leu Leu Ser
            115                 120                 125

Ser Phe Pro Tyr Trp Gly Gln Gly Thr Leu Val Thr Val Ser Ala Ala
            130                 135                 140

Lys Thr Thr Pro Pro Ser Val Tyr Pro Leu Ala
145                 150                 155

<210> SEQ ID NO 36
<211> LENGTH: 155
<212> TYPE: PRT
<213> ORGANISM: Artificial Sequence
<220> FEATURE:
<223> OTHER INFORMATION: Synthetic

<400> SEQUENCE: 36

Met Asp Phe Gly Leu Ser Trp Val Phe Leu Val Leu Val Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
            35                  40                  45

Ser Asp Tyr Tyr Met Tyr Trp Val Arg Gln Thr Pro Glu Lys Arg Leu
        50                  55                  60

Glu Trp Val Ala Thr Ile Ser Asp Gly Gly Thr Tyr Thr Tyr Tyr Pro
65                  70                  75                  80

Asp Ser Val Lys Gly Arg Phe Thr Ile Ser Arg Asp Asn Ala Lys Asn
            85                  90                  95

Asn Leu Tyr Leu Gln Met Asn Ser Leu Lys Ser Glu Asp Thr Ala Met
            100                 105                 110

Tyr Tyr Cys Ala Arg Gly Trp Val Ser Thr Met Val Lys Leu Leu Ser
            115                 120                 125

Ser Phe Pro Tyr Trp Gly Gln Gly Thr Leu Val Thr Val Ser Ala Ala
            130                 135                 140

Lys Thr Thr Pro Pro Ser Val Tyr Pro Leu Ala
145                 150                 155

<210> SEQ ID NO 37
<211> LENGTH: 149
<212> TYPE: PRT
<213> ORGANISM: Artificial Sequence
<220> FEATURE:
<223> OTHER INFORMATION: Synthetic

<400> SEQUENCE: 37

Met Ala Trp Ile Ser Leu Ile Phe Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
            35                  40                  45

Thr Thr Ser Asn Tyr Ala Asn Trp Val Gln Glu Lys Pro Asp His Leu
        50                  55                  60

Phe Thr Gly Leu Val Gly Gly Thr Asn Asn Arg Ala Pro Gly Val Pro

```
                65                  70                  75                  80
Ala Arg Phe Ser Gly Ser Leu Ile Gly Asp Lys Ala Ala Leu Thr Ile
                    85                  90                  95

Thr Gly Ala Gln Thr Glu Asp Glu Ala Ile Tyr Phe Cys Ala Leu Trp
                100                 105                 110

Tyr Ser Asn Tyr Trp Val Phe Gly Gly Thr Lys Leu Thr Val Leu
                115                 120                 125

Gly Gln Pro Lys Ser Ser Pro Ser Val Thr Leu Phe Pro Pro Ser Thr
            130                 135                 140

Glu Glu Leu Ser Leu
145

<210> SEQ ID NO 38
<211> LENGTH: 149
<212> TYPE: PRT
<213> ORGANISM: Artificial Sequence
<220> FEATURE:
<223> OTHER INFORMATION: Synthetic

<400> SEQUENCE: 38

Met Ala Trp Ile Ser Leu Ile Phe Ser Leu Leu Ala Leu Ser Ser Gly
1               5                   10                  15

Ala Ile Ser Gln Ala Val Val Thr Gln Glu Ser Ala Leu Thr Thr Ser
                20                  25                  30

Pro Gly Glu Thr Val Thr Leu Thr Cys Arg Ser Ser Thr Gly Ala Val
            35                  40                  45

Thr Thr Ser Asn Tyr Ala Asn Trp Val Gln Glu Lys Pro Asp His Leu
        50                  55                  60

Phe Thr Gly Leu Ile Gly Gly Thr Ser Asn Arg Ala Pro Gly Val Pro
65                  70                  75                  80

Ala Arg Phe Ser Gly Ser Leu Ile Gly Asp Lys Ala Ala Leu Thr Ile
                    85                  90                  95

Thr Gly Ala Gln Thr Glu Asp Glu Ala Ile Tyr Phe Cys Ala Leu Trp
                100                 105                 110

Tyr Ser Asn Tyr Trp Val Phe Gly Gly Thr Lys Leu Thr Val Leu
                115                 120                 125

Gly Gln Pro Lys Ser Ser Pro Ser Val Thr Leu Tyr Pro Pro Ser Thr
            130                 135                 140

Lys Glu Leu Ser Leu
145

<210> SEQ ID NO 39
<211> LENGTH: 149
<212> TYPE: PRT
<213> ORGANISM: Artificial Sequence
<220> FEATURE:
<223> OTHER INFORMATION: Synthetic

<400> SEQUENCE: 39

Met Ala Trp Thr Ser Leu Leu Leu Ser Leu Leu Ala Leu Ser Ser Gly
1               5                   10                  15

Ala Ile Ser Gln Ala Val Val Thr Gln Glu Ser Ala Leu Thr Thr Ser
                20                  25                  30

Pro Gly Glu Thr Val Thr Leu Thr Cys Arg Ser Ser Thr Gly Ala Val
            35                  40                  45

Thr Thr Ser Asn Tyr Ala Asn Trp Val Gln Glu Lys Pro Asp His Leu
        50                  55                  60
```

```
Phe Thr Gly Leu Ile Gly Gly Thr Asn Asn Arg Ala Pro Gly Val Pro
 65                  70                  75                  80

Ala Arg Phe Ser Gly Ser Leu Ile Gly Asp Lys Ala Ala Leu Thr Ile
                 85                  90                  95

Thr Gly Ala Gln Thr Glu Asp Glu Ala Ile Tyr Phe Cys Ala Leu Trp
            100                 105                 110

Tyr Ser Asn Tyr Trp Val Phe Gly Gly Gly Thr Lys Leu Thr Val Leu
            115                 120                 125

Gly Gln Pro Lys Ser Ser Pro Ser Val Thr Leu Cys Pro Pro Ser Ser
        130                 135                 140

Glu Lys Leu Ser Leu
145

<210> SEQ ID NO 40
<211> LENGTH: 149
<212> TYPE: PRT
<213> ORGANISM: Artificial Sequence
<220> FEATURE:
<223> OTHER INFORMATION: Synthetic

<400> SEQUENCE: 40

Met Ala Trp Thr Ser Leu Leu Phe Ser Leu Leu Ala Leu Ser Ser Gly
 1               5                  10                  15

Ala Ile Ser Gln Ala Val Val Thr Gln Glu Ser Ala Leu Thr Thr Ser
                 20                  25                  30

Pro Gly Glu Thr Val Thr Leu Thr Cys Arg Ser Ser Thr Gly Ala Val
             35                  40                  45

Thr Thr Ser Asn Tyr Ala Asn Trp Val Gln Glu Lys Pro Asp His Leu
         50                  55                  60

Phe Thr Gly Leu Ile Gly Gly Thr Asn Asn Arg Ala Pro Gly Ala Pro
 65                  70                  75                  80

Ala Arg Phe Ser Gly Ser Leu Ile Gly Asp Lys Ala Ala Leu Thr Ile
                 85                  90                  95

Thr Gly Ala Gln Thr Glu Asp Glu Ala Ile Tyr Phe Cys Ala Leu Trp
            100                 105                 110

Tyr Ser Asn Tyr Trp Val Phe Gly Gly Gly Thr Lys Leu Thr Val Leu
            115                 120                 125

Gly Gln Pro Lys Ser Ser Pro Ser Val Thr Leu Cys Pro Pro Ser Thr
        130                 135                 140

Glu Lys Leu Ser Leu
145

<210> SEQ ID NO 41
<211> LENGTH: 149
<212> TYPE: PRT
<213> ORGANISM: Artificial Sequence
<220> FEATURE:
<223> OTHER INFORMATION: Synthetic

<400> SEQUENCE: 41

Met Ala Trp Ile Pro Leu Leu Phe Ser Leu Leu Ala Leu Ser Ser Gly
 1               5                  10                  15

Ala Ile Ser Gln Ala Val Val Thr Gln Glu Ser Ala Leu Thr Thr Ser
                 20                  25                  30

Pro Gly Glu Thr Val Thr Leu Thr Cys Arg Ser Ser Thr Gly Ala Val
             35                  40                  45

Thr Thr Ser Asn Tyr Ala Asn Trp Val Gln Glu Lys Pro Asp His Leu
         50                  55                  60
```

```
Phe Thr Gly Leu Ile Gly Gly Thr Asn Asn Arg Ala Pro Gly Val Pro
 65                  70                  75                  80

Ala Arg Phe Ser Gly Ser Leu Ile Gly Asp Lys Ala Ala Leu Thr Ile
                 85                  90                  95

Ile Gly Ala Gln Thr Glu Asp Glu Ala Ile Tyr Phe Cys Ala Leu Trp
            100                 105                 110

Tyr Ser Asn Tyr Trp Val Phe Gly Gly Thr Lys Leu Thr Val Leu
            115                 120                 125

Gly Gln Pro Lys Ser Ser Pro Ser Val Thr Leu Phe Pro Pro Ser Leu
            130                 135                 140

Glu Lys Leu Ser Leu
145

<210> SEQ ID NO 42
<211> LENGTH: 149
<212> TYPE: PRT
<213> ORGANISM: Artificial Sequence
<220> FEATURE:
<223> OTHER INFORMATION: Synthetic

<400> SEQUENCE: 42

Met Ala Trp Ile Ser Leu Leu Leu Ser Leu Leu Ala Leu Ser Ser Gly
 1               5                  10                  15

Ala Ile Ser Gln Ala Val Val Thr Gln Glu Ser Ala Leu Thr Thr Ser
             20                  25                  30

Pro Gly Glu Thr Val Thr Leu Thr Cys Arg Ser Ser Thr Gly Ala Val
             35                  40                  45

Thr Thr Ser Asn Tyr Ala Asn Trp Val Gln Glu Lys Pro Asp His Leu
 50                  55                  60

Phe Thr Gly Leu Ile Gly Gly Thr Asn Asn Arg Ala Pro Gly Val Pro
 65                  70                  75                  80

Ala Arg Phe Ser Gly Ser Leu Ile Gly Asp Lys Ala Ala Leu Thr Ile
                 85                  90                  95

Thr Gly Ala Gln Thr Glu Asp Glu Ala Ile Tyr Phe Cys Ala Leu Trp
            100                 105                 110

Tyr Ser Asn Tyr Trp Val Phe Gly Gly Thr Lys Leu Thr Val Leu
            115                 120                 125

Gly Gln Pro Lys Ser Ser Pro Ser Val Thr Leu Phe Pro Pro Ser Thr
            130                 135                 140

Glu Glu Leu Ser Leu
145

<210> SEQ ID NO 43
<211> LENGTH: 149
<212> TYPE: PRT
<213> ORGANISM: Artificial Sequence
<220> FEATURE:
<223> OTHER INFORMATION: Synthetic

<400> SEQUENCE: 43

Met Ala Trp Ile Ser Leu Leu Phe Ser Leu Leu Ala Leu Ser Ser Gly
 1               5                  10                  15

Ala Ile Ser Gln Ala Val Val Thr Gln Glu Ser Ala Leu Thr Thr Ser
             20                  25                  30

Pro Gly Glu Thr Val Thr Leu Thr Cys Arg Ser Ser Thr Gly Ala Val
             35                  40                  45

Thr Thr Ser Asn Tyr Ala Asn Trp Val Gln Glu Lys Pro Asp His Leu
```

```
                    50                  55                  60
Phe Thr Gly Leu Ile Gly Gly Thr Asn Asn Arg Ala Pro Gly Val Pro
 65                  70                  75                  80

Ala Arg Phe Ser Gly Ser Leu Ile Gly Asp Lys Ala Ala Leu Thr Ile
                     85                  90                  95

Thr Gly Ala Gln Thr Glu Asp Glu Ala Ile Tyr Phe Cys Ala Leu Trp
            100                 105                 110

Tyr Ser Asn Tyr Trp Val Phe Gly Gly Gly Thr Lys Leu Thr Val Leu
        115                 120                 125

Gly Gln Pro Lys Ser Ser Pro Ser Val Thr Leu Phe Pro Pro Ser Thr
    130                 135                 140

Glu Lys Leu Ser Leu
145

<210> SEQ ID NO 44
<211> LENGTH: 318
<212> TYPE: DNA
<213> ORGANISM: Artificial Sequence
<220> FEATURE:
<223> OTHER INFORMATION: Synthetic

<400> SEQUENCE: 44
atgaacttcg ggttgagctt ggttttcctt gtccttgttt taaaaggtgc ccagtgtgaa      60
gtgcagctgg tggagtctgg gggaggctta gtgaagcctg agggtccct gaaactctcc      120 tgtgcagcct ctggattcac tttcagtgac tattacatgt attgggttcg ccagactccg     180
gaaaagaggc tggagtgggt cgcaaccatt agtgatggtg gtacttacac ctactatcca     240
gacagtgtga agggccgatt caccatctcc agagacaatg ccaagaacaa cctttacctg    300
caaatgaaca gtctgaag                                                    318

<210> SEQ ID NO 45
<211> LENGTH: 465
<212> TYPE: DNA
<213> ORGANISM: Artificial Sequence
<220> FEATURE:
<223> OTHER INFORMATION: Synthetic

<400> SEQUENCE: 45
atggacttcg ggttgagctg ggttttcctt gtccttgttt taaaaggtgt ccagtgtgaa     60
gtgcagctgg tggagtctgg gggaggctta gtgaagcctg agggtccct gaaactctcc     120 tgtgcagcct ctggattcac tttcagtgac tattacatgt attgggttcg ccagactccg    180
gaaaagaggc tggagtgggt cgcaaccatt agtgatggtg gtacttacac ctactatcca    240
gacagtgtga agggccgatt caccatctcc agagacaatg ccaagaacaa cctttacctg   300
caaatgaaca gtctgaagtc tgaggacaca gccatgtatt actgtgcaag aggatgggtt    360
tctactatgg ttaaacttct ttcctccttt ccttactggg gccaagggac tctggtcact    420
gtctctgcag ccaaaacgac acccccatct gtctatccac tggcc                    465

<210> SEQ ID NO 46
<211> LENGTH: 465
<212> TYPE: DNA
<213> ORGANISM: Artificial Sequence
<220> FEATURE:
<223> OTHER INFORMATION: Synthetic

<400> SEQUENCE: 46
atggacttcg ggctgagcag ggttttcctt gtccttgttt taaaaggtgt ccagtgtgaa     60
```

-continued

```
gtgcagctgg tggagtctgg gggaggctta gtgaagcctg agggtccct gaaactctcc    120 tgtgcagcct ctggattcac tttcagtgac tattacatgt attgggttcg ccagactccg    180
gaaaagaggc tggagtgggt cgcaaccatt agtgatggtg gtacttacac ctactatcca    240
gacagtgtga aggggcgatt caccatctcc agagacaatg ccaagaacaa cctttacctg    300
caaatgaaca gtctgaagtc tgaggacaca gccatgtatt actgtgcaag aggatgggtt    360
tctactatgg ttaaacttct ttcctccttt ccttactggg gccaagggac tctggtcact    420
gtctctgcag ccaaaacgac accccatct gtctatccac tggcc                    465

<210> SEQ ID NO 47
<211> LENGTH: 465
<212> TYPE: DNA
<213> ORGANISM: Artificial Sequence
<220> FEATURE:
<223> OTHER INFORMATION: Synthetic

<400> SEQUENCE: 47
atggacttcg ggctgagctg ggttttcctt gtccttgttt taaaggtgt ccagtgtgaa     60 gtgcagctgg tggagtctgg gggaggctta gtgaagcctg agggtccct gaaactctcc    120 tgtgcagcct ctggattcac tttcagtgac tattacatgt attgggttcg ccagactccg    180
gaaaagaggc tggagtgggt cgcaaccatt agtgatggtg gtacttacac ctactatcca    240
gacagtgtga aggggcgatt caccatctcc agagacaatg ccaagaacaa cctttacctg    300
caaatgaaca gtctgaagtc tgaggacaca gccatgtatt actgtgcaag aggatgggtt    360
tctactatgg ttaaacttct ttcctccttt ccttactggg gccaagggac tctggtcact    420
gtctctgcag ccaaaacgac accccatct gtctatccac tggcc                    465

<210> SEQ ID NO 48
<211> LENGTH: 443
<212> TYPE: DNA
<213> ORGANISM: Artificial Sequence
<220> FEATURE:
<223> OTHER INFORMATION: Synthetic

<400> SEQUENCE: 48
ttttccttgt ccttgtttta aaggtgtcc agtgtgaagt gcagctggtg gagtctgggg      60
gaggcttagt gaagcctgga gggtccctga actctcctg tgcagcctct ggattcactt    120
tcagtgacta ttacatgtat tgggttcgcc agactccgga aaagaggctg gagtgggtcg    180
caaccattag tgatggtggt acttacacct actatccaga cagtgtgaag gggcgattca    240
ccatctccag agacaatgcc aagaacaacc tttacctgca aatgaacagt ctgaagtctg    300
aggacacagc catgtattac tgtgcaagag gatgggtttc tactatggtt aaacttcttt    360
cctcctttcc ttactggggc caagggactc tggtcactgt ctctgcagcc aaaacgacac    420
ccccatctgt ctatccactg gcc                                            443

<210> SEQ ID NO 49
<211> LENGTH: 465
<212> TYPE: DNA
<213> ORGANISM: Artificial Sequence
<220> FEATURE:
<223> OTHER INFORMATION: Synthetic

<400> SEQUENCE: 49
atggacttcg ggctgagctg ggttttcctt gtccttgttt taaaggtgt ccagtgtgaa     60
```

| | |
|---|---|
| gtgcagctgg tggagtctgg gggaggctta gtgaagcctg agggtccct gaaactctcc | 120 |
| tgtgcagcct ctggattcac tttcagtgac tattacatgt attgggttcg ccagactccg | 180 |
| gaaaagaggc tggagtgggt cgcaaccatt agtgatggtg gtacttacac ctactatcca | 240 |
| gacagtgtga aggggcgatt caccatctcc agagacaatg ccaagaacaa cctttacctg | 300 |
| caaatgaaca gtctgaagtc tgaggacaca gccatgtatt actgtgcaag aggatgggtt | 360 |
| tctactatgg ttaaacttct ttcctccttt ccttactggg gccaaggggac tctggtcact | 420 |
| gtctctgcag ccaaaacgac accccatct gtctatccac tggcc | 465 |

<210> SEQ ID NO 50
<211> LENGTH: 449
<212> TYPE: DNA
<213> ORGANISM: Artificial Sequence
<220> FEATURE:
<223> OTHER INFORMATION: Synthetic

<400> SEQUENCE: 50

| | |
|---|---|
| atggcctgga tttctcttat attctctctc ctggctctca gctcaggggc catttcccag | 60 |
| gctgttgtga ctcaggaatc tgcactcacc acatcacctg gtgaaacagt cacactcact | 120 |
| tgtcgctcaa gtactggggc tgttacaact agtaactatg ccaactgggt ccaagaaaaa | 180 |
| ccagatcatt tattcactgg tctagtaggt ggtaccaaca accgagctcc aggtgttcct | 240 |
| gccagattct caggctccct gattggagac aaggctgccc tcaccatcac aggggcacag | 300 |
| actgaggatg aggcaatata tttctgtgct ctatggtaca gcaattattg ggtgttcggt | 360 |
| ggaggaacca aactgactgt cctaggccag cccaagtctt cgccatcagt caccctgttc | 420 |
| ccacccctcca ctgaagagct aagcttggg | 449 |

<210> SEQ ID NO 51
<211> LENGTH: 449
<212> TYPE: DNA
<213> ORGANISM: Artificial Sequence
<220> FEATURE:
<223> OTHER INFORMATION: Synthetic

<400> SEQUENCE: 51

| | |
|---|---|
| atggcctgga cttcactctt actctctctc ctggctctca gctcaggggc catttcccag | 60 |
| gctgttgtga ctcaggaatc tgcactcacc acatcacctg gtgaaacagt cacactcact | 120 |
| tgtcgctcaa gtactggggc tgttacaact agtaactatg ccaactgggt ccaagaaaaa | 180 |
| ccagatcatt tattcactgg tctaataggt ggtaccaaca accgagctcc aggtgttcct | 240 |
| gccagattct caggctccct gattggagac aaggctgccc tcaccatcac aggggcacag | 300 |
| actgaggatg aggcaatata tttctgtgct ctatggtaca gcaattattg ggtgttcggt | 360 |
| ggaggaacca aactgactgt cctaggccag cccaagtctt cgccatcagt caccctgtgc | 420 |
| ccgccctcct cagagaagct aagcttggg | 449 |

<210> SEQ ID NO 52
<211> LENGTH: 449
<212> TYPE: DNA
<213> ORGANISM: Artificial Sequence
<220> FEATURE:
<223> OTHER INFORMATION: Synthetic

<400> SEQUENCE: 52

| | |
|---|---|
| atggcctgga ttcctctttt attctctctc ctggctctca gctcaggggc catttcccag | 60 |
| gctgttgtga ctcaggaatc tgcactcacc acatcacctg gtgaaacagt cacactcact | 120 |

```
tgtcgctcaa gtactggggc tgttacaact agtaactatg ccaactgggt ccaagaaaaa      180
ccagatcatt tattcactgg tctaataggt ggtaccaaca accgagctcc aggtgttcct      240
gccagattct caggctccct gattggagac aaggctgccc tcaccatcat aggggcacag      300
actgaggatg aggcaatata tttctgtgct ctatggtaca gcaattattg ggtgttcggt      360
ggaggaacca aactgactgt cctaggccag cccaagtctt cgccatcagt caccctgttc      420
ccgccctcct tagaaaagct tagcttggg                                        449
```

<210> SEQ ID NO 53
<211> LENGTH: 449
<212> TYPE: DNA
<213> ORGANISM: Artificial Sequence
<220> FEATURE:
<223> OTHER INFORMATION: Synthetic

<400> SEQUENCE: 53

```
atggcctgga tttcactttt actctctctc ctggctctca gctcagggc catttcccag        60 gctgttgtga ctcaggaatc tgcactcacc acatcacctg gtgaaacagt cacactcact      120
tgtcgctcaa gtactggggc tgttacaact agtaactatg ccaactgggt ccaagaaaaa      180
ccagatcatt tattcactgg tctaataggt ggtaccaaca accgagctcc aggtgttcct      240
gccagattct caggctccct gattggagac aaggctgccc tcaccatcac aggggcacag      300
actgaggatg aggcaatata tttctgtgct ctatggtaca gcaattattg ggtgttcggt      360
ggaggaacca aactgactgt cctaggccag cccaagtctt cgccatcagt caccctgttt      420
ccaccctcca cagaagagct aagcttggg                                        449
```

<210> SEQ ID NO 54
<211> LENGTH: 449
<212> TYPE: DNA
<213> ORGANISM: Artificial Sequence
<220> FEATURE:
<223> OTHER INFORMATION: Synthetic

<400> SEQUENCE: 54

```
atggcctgga tttcacttat cttctctctc ctggctctca gctcagggc catttcccag        60 gctgttgtga ctcaggaatc tgcactcacc acatcacctg gtgaaacagt cacactcact      120
tgtcgctcaa gtactggggc tgttacaact agtaactatg ccaactgggt ccaagaaaaa      180
ccagatcatt tattcactgg tctaataggt ggtaccagca accgagctcc aggtgttcct      240
gccagattct caggctccct gattggagac aaggctgccc tcaccatcac aggggcacag      300
actgaggatg aggcaatata tttctgtgct ctatggtaca gcaattattg ggtgttcggt      360
ggaggaacca aactgactgt cctaggccag cccaagtctt cgccatcagt caccctgtac      420
ccgccctcta caaaggagct tagcttggg                                        449
```

<210> SEQ ID NO 55
<211> LENGTH: 449
<212> TYPE: DNA
<213> ORGANISM: Artificial Sequence
<220> FEATURE:
<223> OTHER INFORMATION: Synthetic

<400> SEQUENCE: 55

```
atggcctgga cttctctctt attctctctc ctggctctca gctcagggc catttcccag        60 gctgttgtga ctcaggaatc tgcactcacc acatcacctg gtgaaacagt cacactcact      120
```

```
tgtcgctcaa gtactggggc tgttacaact agtaactatg ccaactgggt ccaagaaaaa        180
ccagatcatt tattcactgg tctaataggt ggtaccaaca accgagctcc aggtgctcct        240
gccagattct caggctccct gattggagac aaggctgccc tcaccatcac aggggcacag        300
actgaggatg aggcaatata tttctgtgct ctatggtaca gcaattattg ggtgttcggt        360
ggaggaacca aactgactgt cctaggccag cccaagtctt cgccatcagt caccctgtgc        420
ccgccctcta cagaaaagct aagcttggg                                         449
```

<210> SEQ ID NO 56
<211> LENGTH: 708
<212> TYPE: DNA
<213> ORGANISM: Artificial Sequence
<220> FEATURE:
<223> OTHER INFORMATION: Synthetic

<400> SEQUENCE: 56

```
atggtcagct ctgctcaatt tctcggactc cttcttctgt gctttcaagg aacacgctgc         60
gatattgtga tgacccagtc ccccgccacc ctgtccgtga ctccgggcga ccgggtgtcc        120
ctgtcgtgcc gggcatcaca gagcatctcc gactacctgt cgtggtacca gcagagatca        180
cacgagagcc ctcgcctgat catcaaatac gccagccagt caatctccgg catcccctcg        240
cggttctccg gtccggttc cggctccgac ttcacactgt ccattaactc cgtggaacct        300
gaggacgtgg gagtgtacta ctgtcaacac ggccattcgt tcccgctgac tttcgggtcg        360
ggaaccaagc tggaattgaa gagggcggac gcggccccta ccgtgtcaat ttcccaccg         420 agctccgaac agctcaccag cggcggtgcc tcggtcgtgt gcttcctcaa caacttctat        480
ccaaaagaca ttaacgtcaa gtggaagatc gatggatcgg agagacagaa cggagtgctg        540
aacagctgga ctgatcagga ctccaaggat tcgacctact ccatgagctc cactctgacc        600
ctgaccaagg acgaatacga gcggcacaat tcctacactt gcgaagccac ccacaagacc        660
tcaacgtccc ccatcgtgaa gtccttcaac cgcaacgagt gttgataa                    708
```

<210> SEQ ID NO 57
<211> LENGTH: 234
<212> TYPE: PRT
<213> ORGANISM: Artificial Sequence
<220> FEATURE:
<223> OTHER INFORMATION: Synthetic

<400> SEQUENCE: 57

```
Met Val Ser Ser Ala Gln Phe Leu Gly Leu Leu Leu Leu Cys Phe Gln
1               5                   10                  15

Gly Thr Arg Cys Asp Ile Val Met Thr Gln Ser Pro Ala Thr Leu Ser
            20                  25                  30

Val Thr Pro Gly Asp Arg Val Ser Leu Ser Cys Arg Ala Ser Gln Ser
        35                  40                  45

Ile Ser Asp Tyr Leu Ser Trp Tyr Gln Gln Arg Ser His Glu Ser Pro
    50                  55                  60

Arg Leu Ile Ile Lys Tyr Ala Ser Gln Ser Ile Ser Gly Ile Pro Ser
65                  70                  75                  80

Arg Phe Ser Gly Ser Gly Ser Gly Ser Asp Phe Thr Leu Ser Ile Asn
                85                  90                  95

Ser Val Glu Pro Glu Asp Val Gly Val Tyr Tyr Cys Gln His Gly His
            100                 105                 110

Ser Phe Pro Leu Thr Phe Gly Ser Gly Thr Lys Leu Glu Leu Lys Arg
        115                 120                 125
```

Ala Asp Ala Ala Pro Thr Val Ser Ile Phe Pro Ser Ser Glu Gln
     130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 58
<211> LENGTH: 2201
<212> TYPE: DNA
<213> ORGANISM: Artificial Sequence
<220> FEATURE:
<223> OTHER INFORMATION: Synthetic

<400> SEQUENCE: 58

| | |
|---|---:|
| atgggctgga ccctcgtgtt cctgttcctg ctgagcgtga cggcgggcgt gcactcccaa | 60 |
| atccagcttg tgcagtccgg acccgagctc aggaagccgg gcgaaactgt gcgcatcagc | 120 |
| tgcaaggctt cagggtaccc tttcaccacc gccgggctgc aatgggtgca gaagatgtcc | 180 |
| gggaagggtc tgaagtggat cggatggatg aacacccagt ccgaagtgcc taaatacgcc | 240 |
| gaagaattca agggccgcat tgcgttcagc ctggagacag ccgcctcgac cgcgtacctt | 300 |
| cagatcaaca atctcaagac tgaggacact gccacctact tctgtgccaa gagcgtgtac | 360 |
| ttcaactgga gatacttcga cgtgtgggc gccggaacca ccgtgaccgt gtccagcgcc | 420 |
| aagactaccg ccccgagcgt gtaccctctg gcgccagtgt gcggcgacac gactggcagc | 480 |
| tcggtgacct gggctgcct cgtgaagggt tacttccccg agcccgtgac tctgacttgg | 540 |
| aactcgggct cactgtcgtc cggagtgcat accttcccgg ctgtgctgca aagcgacctc | 600 |
| tatacccttgt catcgtccgt gactgtgacc tcctccacct ggccgtccca gagcatcacc | 660 |
| tgtaatgtcg cccacccctgc ttcatcgact aaggtcgaca gaagatcga gcccagagga | 720 |
| cctaccatca gccctgccc gccctgcaaa tgcccggccc caaacttgct gggagggcct | 780 |
| tccgtgttca tcttccctcc gaaaatcaag gacgtgctga tgatctccct gagcccaatt | 840 |
| gtcacttgcg tggtggtgga tgtgtccgaa gatgacccag atgtgcagat tcatggttc | 900 |
| gtgaacaacg tcgaagtcca taccgcacag acccagaccc accgcgagga ttacaactcg | 960 |
| acgctgcgcg tcgtcagcgc cctgccgatt cagcaccagg attggatgag cggaaaggaa | 1020 |
| ttcaagtgca aagtcaacaa caaggacctt ccggcgccga tcgaacggac catctcgaag | 1080 |
| cctaagggat cagtgcgggc gcctcaggtc tacgtgctcc cgcctccgga gaggaaatg | 1140 |
| accaagaaac aagtcaccct gacttgcatg gtcaccgact tcatgcctga ggacatctat | 1200 |
| gtggagtgga ctaacaacgg aaagactgaa ctgaactaca aaacaccga accagtgctg | 1260 |
| gactctgacg gctcctactt catgtactcg aagctgcggg tggagaagaa aaactgggtg | 1320 |
| gaacgaaact cctactcgtg ttccgtggtg cacgagggtc tgcacaacca ccataccacc | 1380 |
| aagtccttct cccggacccc cggaaaggga tccgccgggg gatccggagg ggactccgaa | 1440 |

-continued

```
gtgcaactgg tggagtcggg tggcggactc gtgaagcccg gggggtcatt gaagctttcc   1500
tgtgctgcct ccggtttcac tttctccgac tattacatgt actgggtcag acagaccccg   1560
gagaagcggc tcgaatgggt ggccaccatt tcggacggtg aacctacac ttactaccct    1620 gactccgtca agggccggtt tactatctcc cgcgacaacg cgaagaacaa tctgtacctc   1680
caaatgaact ccctgaagtc cgaggacacc gccatgtact attgcgcaag gggatgggtc   1740
agcactatgg tcaagctgct gtcatccttc ccttactggg gacagggaac ccttgtgact   1800
gtgtcagccg gtggcggggg gtcgggcggc ggcggttccg gtggaggggg atcccaggcc   1860
gtcgtgaccc aagagtcggc tctgactact tcacccggag aaaccgtgac cctgacatgc   1920
cgctcctcca ctggcgcagt gaccacgagc aattacgcca actgggtgca ggaaaagccc   1980
gatcacctgt tcactggact cattggggga accaacaacc gggcgccggg cgtgcccgct   2040
cggtttagcg gctccctgat tggagacaag gccgccctga ctatcaccgg agcccagacc   2100
gaagatgaag ccatctactt ttgcgcactc tggtactcta actactgggt gtttggcggc   2160
ggaaccaagc tgactgtgct cggacagccg aagtgataaa a                       2201
```

<210> SEQ ID NO 59
<211> LENGTH: 731
<212> TYPE: PRT
<213> ORGANISM: Artificial Sequence
<220> FEATURE:
<223> OTHER INFORMATION: Synthetic

<400> SEQUENCE: 59

```
Met Gly Trp Thr Leu Val Phe Leu Phe Leu Leu Ser Val Thr Ala Gly
1               5                   10                  15

Val His Ser Gln Ile Gln Leu Val Gln Ser Gly Pro Glu Leu Arg Lys
            20                  25                  30

Pro Gly Glu Thr Val Arg Ile Ser Cys Lys Ala Ser Gly Tyr Pro Phe
        35                  40                  45

Thr Thr Ala Gly Leu Gln Trp Val Gln Lys Met Ser Gly Lys Gly Leu
    50                  55                  60

Lys Trp Ile Gly Trp Met Asn Thr Gln Ser Glu Val Pro Lys Tyr Ala
65                  70                  75                  80

Glu Glu Phe Lys Gly Arg Ile Ala Phe Ser Leu Glu Thr Ala Ala Ser
                85                  90                  95

Thr Ala Tyr Leu Gln Ile Asn Asn Leu Lys Thr Glu Asp Thr Ala Thr
            100                 105                 110

Tyr Phe Cys Ala Lys Ser Val Tyr Phe Asn Trp Arg Tyr Phe Asp Val
        115                 120                 125

Trp Gly Ala Gly Thr Thr Val Thr Val Ser Ser Ala Lys Thr Thr Ala
    130                 135                 140

Pro Ser Val Tyr Pro Leu Ala Pro Val Cys Gly Asp Thr Thr Gly Ser
145                 150                 155                 160

Ser Val Thr Leu Gly Cys Leu Val Lys Gly Tyr Phe Pro Glu Pro Val
                165                 170                 175

Thr Leu Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205

Val Thr Ser Ser Thr Trp Pro Ser Gln Ser Ile Thr Cys Asn Val Ala
    210                 215                 220
```

-continued

```
His Pro Ala Ser Ser Thr Lys Val Asp Lys Lys Ile Glu Pro Arg Gly
225                 230                 235                 240

Pro Thr Ile Lys Pro Cys Pro Pro Cys Lys Cys Pro Ala Pro Asn Leu
            245                 250                 255

Leu Gly Gly Pro Ser Val Phe Ile Phe Pro Pro Lys Ile Lys Asp Val
            260                 265                 270

Leu Met Ile Ser Leu Ser Pro Ile Val Thr Cys Val Val Val Asp Val
            275                 280                 285

Ser Glu Asp Asp Pro Asp Val Gln Ile Ser Trp Phe Val Asn Asn Val
            290                 295                 300

Glu Val His Thr Ala Gln Thr Gln Thr His Arg Glu Asp Tyr Asn Ser
305                 310                 315                 320

Thr Leu Arg Val Val Ser Ala Leu Pro Ile Gln His Gln Asp Trp Met
                325                 330                 335

Ser Gly Lys Glu Phe Lys Cys Lys Val Asn Asn Lys Asp Leu Pro Ala
            340                 345                 350

Pro Ile Glu Arg Thr Ile Ser Lys Pro Lys Gly Ser Val Arg Ala Pro
            355                 360                 365

Gln Val Tyr Val Leu Pro Pro Pro Glu Glu Glu Met Thr Lys Lys Gln
            370                 375                 380

Val Thr Leu Thr Cys Met Val Thr Asp Phe Met Pro Glu Asp Ile Tyr
385                 390                 395                 400

Val Glu Trp Thr Asn Asn Gly Lys Thr Glu Leu Asn Tyr Lys Asn Thr
                405                 410                 415

Glu Pro Val Leu Asp Ser Asp Gly Ser Tyr Phe Met Tyr Ser Lys Leu
            420                 425                 430

Arg Val Glu Lys Lys Asn Trp Val Glu Arg Asn Ser Tyr Ser Cys Ser
            435                 440                 445

Val Val His Glu Gly Leu His Asn His His Thr Thr Lys Ser Phe Ser
450                 455                 460

Arg Thr Pro Gly Lys Gly Ser Ala Gly Ser Gly Gly Asp Ser Glu
465                 470                 475                 480

Val Gln Leu Val Glu Ser Gly Gly Gly Leu Val Lys Pro Gly Gly Ser
            485                 490                 495

Leu Lys Leu Ser Cys Ala Ala Ser Gly Phe Thr Phe Ser Asp Tyr Tyr
            500                 505                 510

Met Tyr Trp Val Arg Gln Thr Pro Glu Lys Arg Leu Glu Trp Val Ala
            515                 520                 525

Thr Ile Ser Asp Gly Gly Thr Tyr Thr Tyr Tyr Pro Asp Ser Val Lys
            530                 535                 540

Gly Arg Phe Thr Ile Ser Arg Asp Asn Ala Lys Asn Asn Leu Tyr Leu
545                 550                 555                 560

Gln Met Asn Ser Leu Lys Ser Glu Asp Thr Ala Met Tyr Tyr Cys Ala
                565                 570                 575

Arg Gly Trp Val Ser Thr Met Val Lys Leu Leu Ser Ser Phe Pro Tyr
            580                 585                 590

Trp Gly Gln Gly Thr Leu Val Thr Val Ser Ala Gly Gly Gly Gly Ser
            595                 600                 605

Gly Gly Gly Gly Ser Gly Gly Gly Ser Gln Ala Val Val Thr Gln
            610                 615                 620

Glu Ser Ala Leu Thr Thr Ser Pro Gly Glu Thr Val Thr Leu Thr Cys
625                 630                 635                 640

Arg Ser Ser Thr Gly Ala Val Thr Thr Ser Asn Tyr Ala Asn Trp Val
```

```
                         645                 650                 655
Gln Glu Lys Pro Asp His Leu Phe Thr Gly Leu Ile Gly Gly Thr Asn
            660                 665                 670

Asn Arg Ala Pro Gly Val Pro Ala Arg Phe Ser Gly Ser Leu Ile Gly
        675                 680                 685

Asp Lys Ala Ala Leu Thr Ile Thr Gly Ala Gln Thr Glu Asp Glu Ala
    690                 695                 700

Ile Tyr Phe Cys Ala Leu Trp Tyr Ser Asn Tyr Trp Val Phe Gly Gly
705                 710                 715                 720

Gly Thr Lys Leu Thr Val Leu Gly Gln Pro Lys
                725                 730
```

<210> SEQ ID NO 60
<211> LENGTH: 8
<212> TYPE: PRT
<213> ORGANISM: Artificial Sequence
<220> FEATURE:
<223> OTHER INFORMATION: Synthetic

<400> SEQUENCE: 60

```
Gly Tyr Pro Phe Thr Thr Ala Gly
1               5
```

<210> SEQ ID NO 61
<211> LENGTH: 8
<212> TYPE: PRT
<213> ORGANISM: Artificial Sequence
<220> FEATURE:
<223> OTHER INFORMATION: Synthetic

<400> SEQUENCE: 61

```
Met Asn Thr Gln Ser Glu Val Pro
1               5
```

<210> SEQ ID NO 62
<211> LENGTH: 13
<212> TYPE: PRT
<213> ORGANISM: Artificial Sequence
<220> FEATURE:
<223> OTHER INFORMATION: Synthetic

<400> SEQUENCE: 62

```
Ala Lys Ser Val Tyr Phe Asn Trp Arg Tyr Phe Asp Val
1               5                   10
```

<210> SEQ ID NO 63
<211> LENGTH: 6
<212> TYPE: PRT
<213> ORGANISM: Artificial Sequence
<220> FEATURE:
<223> OTHER INFORMATION: Synthetic

<400> SEQUENCE: 63

```
Gln Ser Ile Ser Asp Tyr
1               5
```

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

```
Gln His Gly His Ser Phe Pro Leu Thr
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic

<400> SEQUENCE: 65

Gly Phe Thr Phe Ser Asp Tyr Tyr
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic

<400> SEQUENCE: 66

Ile Ser Asp Gly Gly Thr Tyr Thr
1               5

<210> SEQ ID NO 67
<211> LENGTH: 17
<212> TYPE: PRT
<213> ORGANISM: Artificial Sequence
<220> FEATURE:
<223> OTHER INFORMATION: Synthetic

<400> SEQUENCE: 67

Ala Arg Gly Trp Val Ser Thr Met Val Lys Leu Leu Ser Ser Phe Pro
1               5                   10                  15

Tyr

<210> SEQ ID NO 68
<211> LENGTH: 9
<212> TYPE: PRT
<213> ORGANISM: Artificial Sequence
<220> FEATURE:
<223> OTHER INFORMATION: Synthetic

<400> SEQUENCE: 68

Thr Gly Ala Val Thr Thr Ser Asn Tyr
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic

<400> SEQUENCE: 69

Ala Leu Trp Tyr Ser Asn Tyr Trp Val
1               5
```

The invention claimed is:

1. An NLRP3 inflammasome modulator that binds to IL-1R1 and NLRP3;

wherein the NLRP3 inflammasome modulator comprises a bispecific antibody having a first antibody moiety and a second antibody moiety, the first antibody moiety comprising three heavy chain complementary determining regions (CDRs) and three light chain CDRs, wherein the heavy chain CDRs of the first antibody moiety comprise GYPFTTAG (SEQ ID NO: 60), MNTOSEVP (SEQ ID NO: 61), and AKSVYFNWRYFDV (SEQ ID NO: 62), wherein the light chain CDRs of the first antibody A moiety comprise QSISDY (SEQ ID NO: 63), YAS, and QHGH-SFPLT (SEQ ID NO: 64); and the second antibody moiety comprising three heavy chain complementary determining regions (CDRs) and three light chain CDRs, wherein the heavy chain CDRs of the second antibody moiety comprise GFTFSDYY (SEQ ID NO: 65), ISDGGTYT (SEQ ID NO: 66), and ARGWVSTMVKLLSSFPY (SEQ ID NO: 67), wherein the light chain CDRs of the second antibody moiety comprise TGAVTTSNY (SEQ ID NO: 68), GTN, and ALWYSNYWV (SEQ ID NO: 69).

2. The NLRP3 inflammasome modulator of claim 1, wherein the the first and/or second antibody moiety of the bispecific antibody is selected from the group consisting of: a polyclonal antibody, a monoclonal antibody, a humanized antibody, a chimeric antibody, a combination thereof, and fragments of each thereof.

3. The NLRP3 inflammasome modulator of claim 1, wherein the first and/or second antibody moiety is a monoclonal antibody.

4. The NLRP3 inflammasome modulator of claim 1, wherein the bispecific antibody is a recombinant humanized bispecific antibody or antibody fragment that binds to both of IL-1R1 and NLRP3.

5. The NLRP3 inflammasome modulator of claim 1, wherein the first and/or second antibody moiety of the bispecific antibody comprises an antibody fragment, wherein the antibody fragment is one or more of Fab, Fv, Fab', (Fab')2, scFv, bis-scFv, minibody, Fab2, and Fab3.

6. The NLRP3 inflammasome modulator of claim 1, wherein the bispecific antibody comprises the amino acid sequence: MVSSAQFLGLLLLCFQGTRCDIVMTQSPATLSVTPGDRVSLSCRASQSISDYLSWYQQRS HESPRLIIKYASQSISGIPSRFSGSGSGSDFTLSINSVEPEDVGVYYCQHGHSFPLTFGSGTK LELKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC(SEQ ID NO: 57).

7. The NLRP3 inflammasome modulator of claim 1, wherein the bispecific antibody comprises the amino acid sequence:

(SEQ ID NO: 59)
MGWTLVFLFLLSVTAGVHSQIQLVQSGPELRKPGETVRISCKASGYPFT

TAGLQWVQKMSGKGLKWIGWMNTQSEVPKYAEEFKGRIAFSLETMSTAY

-continued

LQINNLKTEDTTYFCAKSVYFNWRYFDVWGAGTTVTVSSAKTTAPSVYP

LAPVCGDTTGSSVTLGCLVKGYFPEPVTLTWNSGSLSSGVHTFPAVLQS

DLYTLSSSVTVTSSTWPSQSITCNVAHPASSTKVDKKIEPRGPTIKPCP

PCKCPAPNLLGGPSVFIFPPKIKDVLMISLSPIVTCVVVDVSEDDPDVQ

ISWFVNNVEVHTAQTQTHREDYNSTLRVVSALPIQHQDWMSGKEFKCKV

NNKDLPAPIERTISKPKGSVRAPQVYVLPPPEEEMTKKQVTLTCMVTDF

MPEDIYVEWTNNGKTELNYKNTEPVLDSDGSYFMYSKLRVEKKNWVERN

SYSCSVVHEGLHNHHTTKSFSRTPGKGSAGGSGGDSEVQLVESGGGLVK

PGGSLKLSCAASGFTFSDYYMYWVRQTPEKRLEWVATISDGGTYTYYPD

SVKGRFTISRDNAKNNLYLQMNSLKSEDTAMYYCARGWVSTMVKLLSSF

PYWGQGTLVTVSAGGGGSGGGGSGGGGSQAVVTQESALTTSPGETVTLT

CRSSTGAVTTSNYANWVQEKPDHLFTGLIGGTNNRAPGVPARFSGSLIG

DKAALTITGAQTEDEAIYFCALWYSNYWVFGGGTKLTVLGQPK.

8. A method for treatment of an inflammation-related disorder, the method comprising:
administering a therapeutically effective amount of the NLRP3 inflammasome modulator of claim 1 that suppresses activation and/or signaling of the NLRP3 inflammasome to a subject in need of such treatment.

9. The method of claim 8, wherein the NLRP3 inflammasome modulator is formulated as a medicament.

10. The method of claim 8, wherein the inflammation-related disorder comprises one or more of: Atherosclerosis; Age-Related Macular degeneration, Dry Eye Syndrome, Glaucoma, Sjogren's syndrome; Diabetes; Inflammatory eye disease; Depression; Alzheimer's Disease; Parkinson's Disease; Inflammatory Bowel Disease; Rheumatoid Arthritis; Ageing; Dermatological conditions; and Cancer.

11. The method of claim 8, wherein the bispecific antibody comprises the amino acid sequence of SEQ ID NO: 57.

12. The method of claim 8, wherein the bispecific antibody comprises the amino acid sequence of SEQ ID NO: 59.

13. A method to reduce or treat at least one symptom of an inflammation-related disorder in a subject comprising selectively inhibiting and/or reducing activation of the inflammasome pathway by administering to the subject an effective amount of the NLRP3 inflammasome modulator of claim 1.

* * * * *